US012727807B2

(12) United States Patent
Bai et al.

(10) Patent No.: US 12,727,807 B2
(45) Date of Patent: Sep. 8, 2026

(54) APPARATUSES, METHODS, AND SYSTEMS FOR RECONFIGURABLE THREE-DIMENSIONAL MESOSTRUCTURES

(71) Applicant: The University of North Carolina at Chapel Hill, Chapel Hill, NC (US)

(72) Inventors: Wubin Bai, Chapel Hill, NC (US); Lin Zhang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 19/122,211

(22) PCT Filed: Oct. 18, 2023

(86) PCT No.: PCT/US2023/077203
§ 371 (c)(1),
(2) Date: Apr. 17, 2025

(87) PCT Pub. No.: WO2024/086654
PCT Pub. Date: Apr. 25, 2024

(65) Prior Publication Data
US 2026/0108194 A1 Apr. 23, 2026

Related U.S. Application Data

(60) Provisional application No. 63/380,355, filed on Oct. 20, 2022.

(51) Int. Cl.
*A61B 5/287* (2021.01)
*A61B 5/00* (2006.01)
(Continued)

(52) U.S. Cl.
CPC ............ *A61B 5/287* (2021.01); *A61B 5/6852* (2013.01); *B29C 53/36* (2013.01); *B29C 61/10* (2013.01);
(Continued)

(58) Field of Classification Search
CPC ....... A61B 5/287; A61B 5/291; A61B 5/6852; B22F 12/41; B29C 61/10; B29C 61/36
See application file for complete search history.

(56) References Cited

U.S. PATENT DOCUMENTS 8,728,067 B2 * 5/2014 Prakash ................. A61B 18/18 606/41
10,538,028 B2 1/2020 Rogers et al.
(Continued)

FOREIGN PATENT DOCUMENTS

CN 115171554 A 10/2022

OTHER PUBLICATIONS

Abdullah et al., "Kirigami-Inspired Self-Assembly of 3D Structures," Adv. Funct. Mater., 30:1909888, (2020).
(Continued)

*Primary Examiner* — Eun Hwa Kim
(74) *Attorney, Agent, or Firm* — Alston & Bird LLP

(57) ABSTRACT

Methods, apparatuses, and systems for fabricating reconfigurable three-dimensional mesostructures and microelectronic systems are provided. An example method for fabricating an example three-dimensional mesostructure includes providing a folding host in an unfolded state, wherein the folding host defines a trench portion between a first bonding site portion and a second bonding site portion of the folding host; bonding a precursor to the first bonding site portion and the second bonding site portion so that the precursor is suspended across the trench portion of the folding host; shaping the precursor to the three-dimensional mesostructure by transforming the folding host from the unfolded state to a folded state; and disengaging the three-dimensional mesostructure from the folding host.

20 Claims, 45 Drawing Sheets

(51) Int. Cl.
*B29C 53/36* (2006.01)
*B29C 61/10* (2006.01)
*B82Y 15/00* (2011.01)

(52) U.S. Cl.
CPC . *A61B 2562/0261* (2013.01); *A61B 2562/028* (2013.01); *A61B 2562/125* (2013.01); *A61B 2562/164* (2013.01); *B82Y 15/00* (2013.01)

(56) References Cited

U.S. PATENT DOCUMENTS

| | | | |
|---|---|---|---|
| 2005/0280647 A1 | 12/2005 | Wang et al. |
| 2015/0134042 A1 | 5/2015 | Ollivier |
| 2016/0158545 A1 | 6/2016 | Khairkhahan et al. |
| 2021/0053329 A1 | 2/2021 | Sun et al. |

OTHER PUBLICATIONS

Alcantara et al., "Mechanically interlocked 3D multi-material micromachines," Nature Communications, 11:5957, (2020).
Anacleto et al., "Design and Characterization of 3-D Self-Folded Microantennas for Implantable Microdevices," IEEE Transactions on Antennas and Propagation, (68(3):2031-2039, (2020).
Bai et al., "Geometrically reconfigurable 3D mesostructures and electromagnetic devices through a rational bottom-up design strategy," Sci Adv. 6:eabb7417, (2020).
Bracaglia et al., "3D Printing for the Design and Fabrication of Polymer-Based Gradient Scaffolds," Acta Biomater., 56:3-13, (2017).
Castle et al., "Additive lattice kirigami," Sci. Adv., 2:e1601258, (2016).
Chen et al., "Kirigami/origami: unfolding the new regime of advanced 3D microfabrication/nanofabrication with "folding"," Light: Science & Applications, 9:75, (2020).
Deng et al., "Deterministic Self-Morphing of Soft-Stiff Hybridized Polymeric Films for Acoustic Metamaterials," ACS Appl. Mater. Interfaces, 12:13378-1338, (2020).
Desbiolles et al., "Ion beam etching redeposition for 3D multimaterial nanostructure manufacturing," Microsystems & Nanoengineering, 5:11, (2019).
Dudte et al., "Programming Curvature using Origami Tessellations," Nature Materials, 15:583-588, (2016).
Fan et al., "Inverse Design Strategies for 3D Surfaces Formed by Mechanically Guided Assembly," Adv. Mater., 32:1908424, (2020).
Fu et al., "Mechanically-guided deterministic assembly of 3D mesostructures assisted by residual stresses," Small, 13(24), (2017).
Fu et al., "Morphable 3D Mesostructures and Microelectronic Devices by Multistable Buckling Mechanics," Nat Mater., 17:268-276, (2018).
Geng et al., "Ultrafast multi-focus 3-D nano-fabrication based on two-photon polymerization," Nature Communications, 10:2179, (2019).
Guerin et al., "Formation of 2D and 3D multi-tori mesostructures via crystallization-driven self-assembly," Sci. Adv., 6:eaaz7301, (2020).
Guo et al., "Controlled mechanical assembly of complex 3D mesostructures and strain sensors by tensile buckling," NPJ Flexible Electronics, 2:14, (2018).
Helou et al., "Digital logic gates in soft, conductive mechanical metamaterials," Nature Communications, 12:1633, (2021).
Huang et al., "Assembly and Self-Assembly of Nanomembrane Materials—From 2D to 3D," Small, 14:1703665, (2018).
Huddy et al., "Transforming 3D-printed mesostructures into multimodal sensors with nanoscale conductive metal oxides," Cell Reports Physical Science, 3:100786, (2022).
Humood et al., Fabrication and Deformation of 3D Multilayered Kirigami Microstructures, Small, 14:1703852, (2018).
Kim et al., "Shape morphing smart 3D actuator materials for micro soft robot," Materials Today, 41:243-269, (2020).
Kwak et al., "Wireless sensors for continuous, multimodal measurements at the skin interface with lower limb prostheses," Sci Transl Med., 12(574), (2020).
Lee et al., Two-dimensional materials in functional three-dimensional architectures with applications in photodetection and imaging, Nature Communications, 9:1417, (2018).
Li et al., "Reconfigurable Three-Dimensional Mesotructures of Spatially Programmed Liquid Crystal Elastomers and Their Ferromagnetic Composites," Advanced Function Materials, 31:2100338, (2021).
Li et al., "Remotely Controlled, Reversible, On-Demand Assembly and Reconfiguration of 3D Mesostructures via Liquid Crystal Elastomer Platforms," ACS Applied Materials & Interfaces, 13(7) 8929-8939, (2021).
Lilly et al., "Higher-Order Properties of Analytic Wavelets," IEEE Transactions on Signal Processing, 57(1):146-160, (2009).
Ling et al., "Bioinspired elastomer composites with programmed mechanical and electrical anisotropies," Nature Communications, 13:524, (2022).
Liu et al., "Postbuckling analyses of frame mesostructures consisting of straight ribbons for mechanically guided three-dimensional assembly," Proc. R. Soc. A, 475:20190012, (2019).
Luan et al., "Complex 3D microfluidic architectures formed by mechanically guided compressive buckling," Sci. Adv., 7:eabj3686, (2021).
Luan et al., "Design and Fabrication of Heterogeneous, Deformable Substrates for the Mechanically Guided 3D Assembly," ACS Appl. Mater. Interfaces, 11:3482-3492, (2019).
Mitra et al., "Miniaturization of Meander Line Slot Antenna," 2015 IEEE-APS Topical Conference on Antennas and Propagation in Wireless Communications (APWC), Turin, Italy, pp. 1255-1257, (2015).
Ning et al., "Assembly of Advanced Materials into 3D Functional Structures by Methods Inspired by Origami and Kirigami: A Review," Adv. Mater. Interfaces, 5:1800284, (2018).
Ning et al., "Mechanically active materials in three-dimensional mesostructures," Sci Adv., 4:eaat8313, (2018).
Park et al., "Remotely Triggered Assembly of 3D Mesostructures Through Shape-Memory Effects," Adv. Mater., 31:1905715, (2019).
Park et al., "Three-dimensional, multifunctional neural interfaces for cortical spheroids and engineered assembloids," Sci. Adv., 7:eabf9153, (2021).
Park et al., "Wireless, skin-interfaced sensors for compression therapy," Sci Adv, 6:eabe1655, (2020).
Placone et al., "Recent advances in extrusion-based 3D printing for biomedical applications," Adv Healthc Mater., 7:e1701161, (2018).
Puschmann et al., "Diagnosis and Treatment of Common Forms of Tremor," Semin Neurol., 31:65-77, (2011).
Sharma et al., "Approach to a tremor patient," Ann Indian Acad Neurol, 19:433-43, (2016).
Shusteff et al., "One-step volumetric additive manufacturing of complex polymer structures," Sci. Adv., 3:eaao5496, (2017).
Skoric et al., "Layer-by-Layer Growth of Complex-Shaped Three-Dimensional Nanostructures with Focused Electron Beams," Nano Lett., 20:184-191, (2020).
Visser, H., "Analytical equations for the analysis of folded dipole array antenna," Proceedings of the 38th European Microwave Conference, Amsterdam, Netherlands, pp. 706-709, (2008).
Wang et al., "Freestanding 3D Mesostructures, Functional Devices, and Shape-Programmable Systems Based on Mechanically Induced Assembly with Shape Memory Polymers," Adv. Mater., 31:1805615, (2019).
Won et al., "Multimodal Sensing with a Three-Dimensional Piezoresistive Structure," ACS Nano, 13:10972-10979, (2019).
Xue et al., "Kirigami pattern design of mechanically driven formation of complex 3D structures through topology optimization," Extreme Mechanics Letters, 15:139-144, (2017).
Yan et al., "Controlled mechanical buckling for origami-inspired construction of 3D microstructures in advanced materials," Adv Funct Mater., 26(16):2629-2639, (2016).
Yan et al., "Deterministic assembly of 3D mesostructures in advanced materials via compressive buckling: A short review of recent progress," Extreme Mechanics Letters, 11:96-104, (2017).

(56) References Cited

OTHER PUBLICATIONS

Yan et al., "Mechanical assembly of complex, 3D mesostructures from releasable multilayers of advanced materials," Sci. Adv., 2:e1601014, (2016).
Zhang et al., "A mechanically driven form of Kirigami as a route to 3D mesostructures in micro/nanomembranes," PNAS, 112(38):11757-11764, (2015).
Zhang et al., "Printing, folding and assembly methods for forming 3D mesostructures in advanced materials," Nature Reviews, 2:17019, (2017).
Zhang et al., "Rapidly deployable and morphable 3D mesostructures with applications in multimodal biomedical devices," PNAS, 118(11):e2026t414118, (2021).
Zhao et al., Mechanically Guided Hierarchical Assembly of 3D Mesostructures, Adv. Mater., 34:2109416, (2022).
Zheng et al., "Continuous Monitoring of Essential Tremor Using a Portable System Based on Smartwatch," Frontiers in Neurology, 8(96), (2017).
WIPO Application No. PCT/US2023/077203, PCT International Search Report and Written Opinion of the International Searching Authority mailed Feb. 13, 2024.

* cited by examiner

4100

Start — 4101

Form An Epicardial Bioelectronic Precursor — 4103

Bind The Epicardial Bioelectronic Precursor To A Folding Host In An Unfolded State — 4105

Shape The Epicardial Bioelectronic Precursor To The Three-Dimensional Epicardial Bioelectronic Probe By Transforming The Folding Host From The Unfolded State To A Folded State — 4107

Encapsulate The Three-Dimensional Epicardial Bioelectronic Probe In A Catheter — 4109

End — 4111

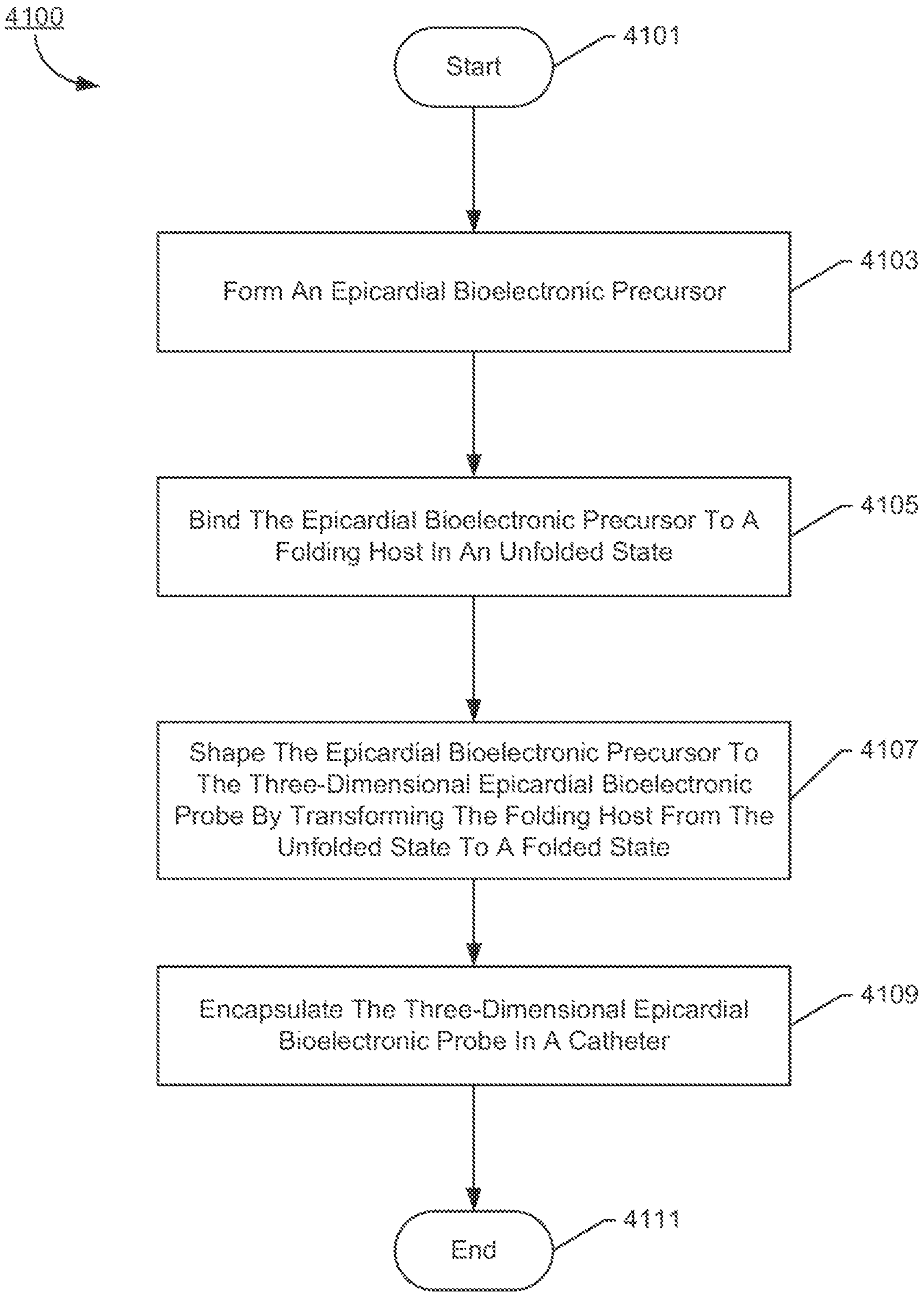

FIG. 41

APPARATUSES, METHODS, AND SYSTEMS FOR RECONFIGURABLE THREE-DIMENSIONAL MESOSTRUCTURES

CROSS-REFERENCE TO RELATED APPLICATIONS

This application claims the priority to and the benefit of PCT/US2023/077203, filed Oct. 18, 2023, which claims priority to and benefit of U.S. Provisional Patent Application No. 63/380,355, filed Oct. 20, 2022, the entire content of which are incorporated by reference in their entirety.

FIELD OF THE INVENTION

Embodiments of the present disclosure relate generally to methods, apparatuses, and systems for fabricating reconfigurable three-dimensional structures such as, but not limited to, mesostructures systems. For example, various embodiments of the present disclosure provide example methods for fabricating reconfigurable and freestanding three-dimensional mesostructures that include, but are not limited to, example three-dimensional epicardial bioelectronic probes and example three-dimensional epicardial bioelectronic probe systems.

BACKGROUND

The fabrication of three-dimensional structures is an important step in manufacturing mesosystems and microsystems. However, many methods of fabricating three-dimensional structures are plagued with technical challenges and difficulties. For example, many methods cannot be implemented to fabricate three-dimensional structures that comprise materials such as, but not limited to, semiconductor materials. As another example, many methods cannot fabricate three-dimensional structures that are reconfigurable and freestanding.

BRIEF SUMMARY

Various embodiments described herein are related to fabricating reconfigurable three-dimensional mesostructures and microelectronic systems.

In accordance with various embodiments of the present discourse, a method for fabricating a three-dimensional mesostructure is provided. In some embodiments, the example comprises: providing a folding host in an unfolded state, wherein the folding host defines a trench portion between a first bonding site portion and a second bonding site portion of the folding host; bonding a precursor to the first bonding site portion and the second bonding site portion so that the precursor is suspended across the trench portion of the folding host; shaping the precursor to the three-dimensional mesostructure by transforming the folding host from the unfolded state to a folded state; and disengaging the three-dimensional mesostructure from the folding host.

In some embodiments, providing the folding host further comprises: fabricating a glass substrate with a bilayer comprising polydimethylsiloxane (PDMS) and poly lactic-co-glycolic acid (PLGA); laser cutting a hollow portion on the bilayer to form the trench portion; and removing the bilayer from the glass substrate to form the folding host.

In some embodiments, fabricating the glass substrate with the bilayer comprises: spin casting a PDMS layer on the glass substrate; and spin casting a PLGA layer on the PDMS layer.

In some embodiments, the precursor comprises monocrystalline silicon.

In some embodiments, bonding the precursor further comprises: forming the precursor on a device layer of a silicon-on-insulator (SOI) substrate; retrieving the precursor from the SOI substrate by a polydimethylsiloxane (PDMS) stamp; and transferring the precursor onto the folding host.

In some embodiments, the precursor comprises precursor material. In some embodiments, the precursor material comprises at least one of copper or gold.

In some embodiments, bonding the precursor further comprises: form a precursor layer by depositing the precursor material on a sacrificial layer of a silicon wafer substrate; forming the precursor on the precursor layer; retrieving the precursor by a polydimethylsiloxane (PDMS) stamp; and transferring the precursor onto the folding host.

In some embodiments, the precursor comprises a first precursor end and a second precursor end that is opposite to the first precursor end. In some embodiments, the first precursor end is bound to the first bonding site portion of the folding host. In some embodiments, the second precursor end is bound to the second bonding site portion of the folding host.

In some embodiments, the precursor comprises precursor material. In some embodiments, prior to bonding the precursor to the first bonding site portion and the second bonding site portion, the method further comprises: determining a ratio between a precursor length and a precursor thickness associated with the precursor based at least in part on a material failure threshold associated with the precursor material.

In some embodiments, transforming the folding host from the unfolded state to the folded state comprises: exerting folding motions on the first bonding site portion and the second bonding site portion along a trench axis of the trench portion.

In accordance with various embodiments of the present disclosure, a method for fabricating a three-dimensional epicardial bioelectronic probe is provided. In some embodiments, the method comprises forming an epicardial bioelectronic precursor, wherein the epicardial bioelectronic precursor comprises a first precursor end portion and a second precursor end portion, wherein at least one strain sensor is positioned between the first precursor end portion and the second precursor end portion; bonding the epicardial bioelectronic precursor to a folding host in an unfolded state, wherein the folding host defines a trench portion between a first bonding site portion and a second bonding site portion of the folding host; shaping the epicardial bioelectronic precursor to the three-dimensional epicardial bioelectronic probe by transforming the folding host from the unfolded state to a folded state; and encapsulating the three-dimensional epicardial bioelectronic probe in a catheter.

In some embodiments, the epicardial bioelectronic precursor comprises a polyester layer, a gold layer disposed on top of the polyester layer, and a parylene layer disposed on top of the gold layer In some embodiments, a polyester layer thickness associated with the polyester layer is 10 μm. In some embodiments, a gold layer thickness associated with the gold layer is 50 nm. In some embodiments, a parylene layer thickness associated with the parylene layer is 2 μm.

In some embodiments, the at least one strain sensor comprises at least one gold wire forming a strain sensitive pattern on the gold layer.

In some embodiments, a wire width associated with the at least one gold wire is 110 μm. In some embodiments, a gap width associated with the strain sensitive pattern is 30 μm.

In some embodiments, the epicardial bioelectronic precursor comprises a first strain sensor that is positioned on the first precursor end portion and a second strain sensor that is positioned on the second precursor end portion.

In some embodiments, the epicardial bioelectronic precursor comprises: a first strain sensor that is positioned on a first side of the epicardial bioelectronic precursor and between the first precursor end portion and the second precursor end portion; and a second strain sensor that is positioned on a second side of the epicardial bioelectronic precursor and between the first precursor end portion and the second precursor end portion.

In some embodiments, bonding the epicardial bioelectronic precursor to the folding host further comprises: bonding the first precursor end portion of the epicardial bioelectronic precursor to the first bonding site portion; and bonding the second precursor end portion of the epicardial bioelectronic precursor to the second bonding site portion.

In some embodiments, shaping the epicardial bioelectronic precursor to the three-dimensional epicardial bioelectronic probe further comprises: exerting folding motions on the first bonding site portion and the second bonding site portion along a trench axis of the trench portion.

In some embodiments, encapsulating the three-dimensional epicardial bioelectronic probe in the catheter comprises: causing the at least one strain sensor to retract within the catheter.

In accordance with various embodiments of the present disclosure, a three-dimensional epicardial bioelectronic probe system is provided. In some embodiments, the three-dimensional epicardial bioelectronic probe system comprises a catheter defining a distal opening; and a three-dimensional epicardial bioelectronic probe comprising at least one cantilever portion. In some embodiments, the three-dimensional epicardial bioelectronic probe is transformable between a closed state and an open state.

In some embodiments, when the three-dimensional epicardial bioelectronic probe is in the closed state, the at least one cantilever portion is positioned in the catheter and oriented towards the distal opening of the catheter, and when the three-dimensional epicardial bioelectronic probe is in the open state, the at least one cantilever portion is positioned out of the catheter and arranged radially around the distal opening of the catheter.

In some embodiments, when the three-dimensional epicardial bioelectronic probe is in the closed state, the three-dimensional epicardial bioelectronic probe is encapsulated in the catheter.

In some embodiments, the three-dimensional epicardial bioelectronic probe comprises a probe end portion positioned in the catheter and moveable between a proximal end of the catheter and a distal end of the catheter.

In some embodiments, a movement of the probe end portion from the proximal end of the catheter to the distal end of the catheter causes the three-dimensional epicardial bioelectronic probe to transform from the closed state to the open state.

In some embodiments, when the three-dimensional epicardial bioelectronic probe is in the closed state, the at least one cantilever portion is in a parallel arrangement with the catheter.

In some embodiments, when the three-dimensional epicardial bioelectronic probe is in the open state, the at least one cantilever portion is in a non-parallel arrangement with the catheter.

In some embodiments, the at least one cantilever portion comprises a polyester layer, a gold layer disposed on top of the polyester layer, and a parylene layer disposed on top of the gold layer.

In some embodiments, a polyester layer thickness associated with the polyester layer is 10 μm. In some embodiments, a gold layer thickness associated with the gold layer is 50 nm. In some embodiments, a parylene layer thickness associated with the parylene layer is 2 μm.

In some embodiments, at least one strain sensor is on the gold layer and comprises at least one gold wire forming a strain sensitive pattern.

In some embodiments, a wire width associated with the at least one gold wire is 110 μm. In some embodiments, a gap width associated with the strain sensitive pattern is 30 μm.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1A:
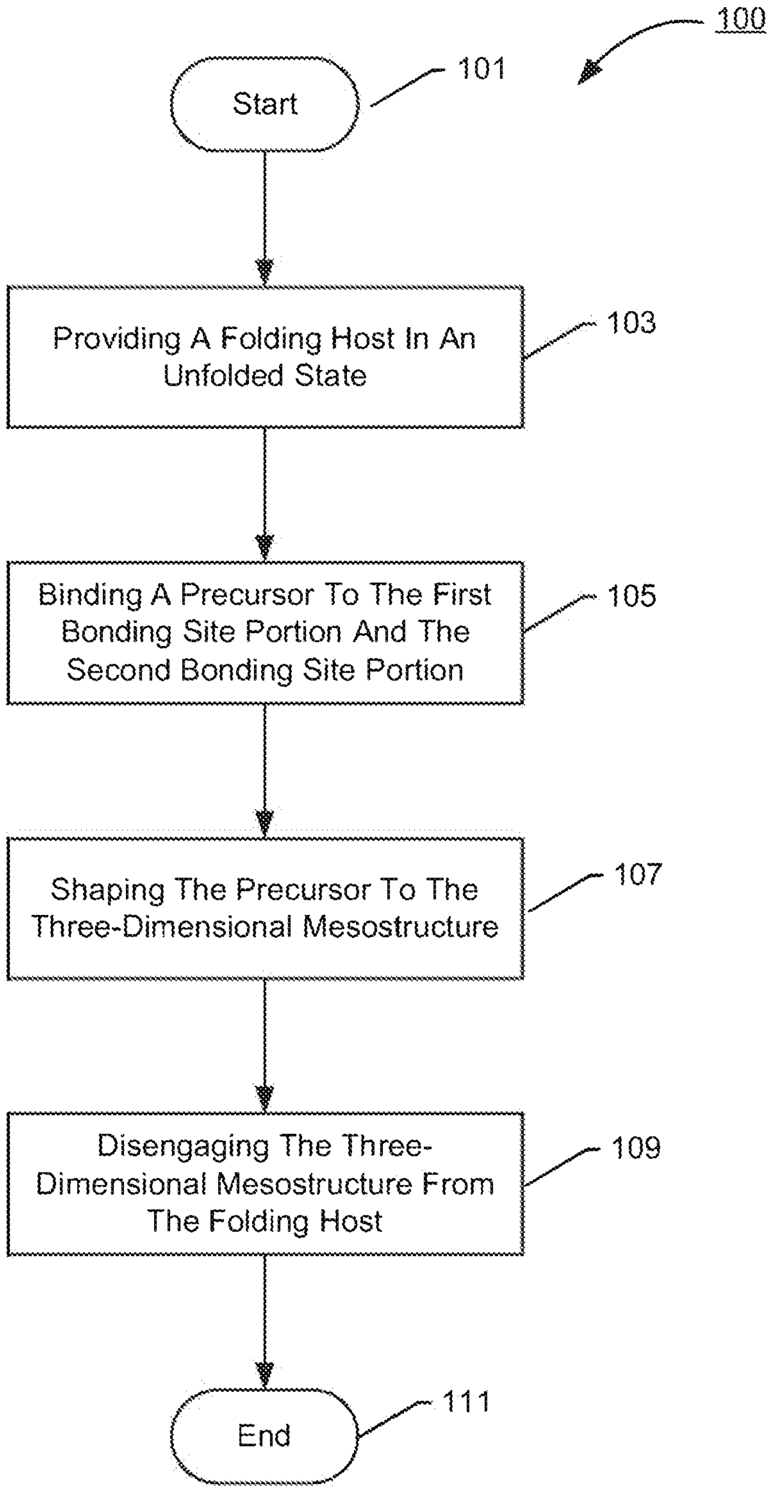
FIG. 1A provides an example flow diagram illustrating an example method of fabricating an example three-dimensional mesostructure in accordance with some embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment)

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

Overview

As described above, there are many technical challenges and difficulties associated with fabrication techniques for three-dimensional structures such as, but not limited to, Example techniques for fabricating three-dimensional micro- and nanostructures include ion-beam lithography, layer-by-layer growth, multiphoton lithography, printing-based fabrication, and holographic lithography. Such techniques offer high precision in three-dimensional structural formation, but are with limited applicability and do not enable structural morphability for certain high-performance materials such as monocrystalline silicon.

Some methods exploit concepts in self-assembly and mechanically guided assembly to address this limitation, providing capability of compatible integration into modern planar technologies and associated thin-film deposition and processing techniques that are established in the semiconductor industry. For example, some example methods provide mechanically guided assembly that enables deterministic formation of sophisticated three-dimensional architectures from two-dimensional structures by controlled compressive buckling as a result from strain release of pre-stretched elastomeric substrates. However, the reliance on the elastomeric substrates complicates formation of free-standing or minimally standing three-dimensional mesostructures and limits the structural diversity to some extent. In other words, strong reliance on a planar base or template for anchoring precludes the implementation of those approaches in a broader horizon of applications, especially in making reconfigurable medical devices interfaced with biological tissues (such as, but not limited to, medical catheters and surgical probes).

The development of schemes for realizing morphable three-dimensional mesostructures that can enrich classes of materials and designs of devices found in forms of electronics, optoelectronics, and microelectromechanical systems remains to be a central breakpoint for new device capabilities and applications. Furthermore, concepts of origami and kirigami, infiltrated in some schemes, are yet to unleash significant potentials in forming diverse morphable mesostructures in three-dimensional via releasing multi-dimensional freedoms of folding. For example, DNA and proteins fold in three dimensions to enable functions that sustain life. Emulation of such folding schemes for functional materials can unleash unprecedented potentials in advancing a wide range of technologies.

Various embodiments of the present disclosure overcome such technical challenges and difficulties.

In particular, various embodiments of the present disclosure provide a micro-folding strategy that demonstrates the capability of three-dimensional mesostructures fabrication of various materials (e.g., monocrystalline silicon, metals, and polymers) with length scale ranging from micrometer to centimeter. By predesigning the folding host and configuring the folding registration (e.g., parallel, angled, and switching), three-dimensional mesostructures in fully freestanding forms with various complex configurations have been demonstrated. In particular, any transitional structures with reversible configurations during the micro-folding assembly can be effectively obtained and maintained by controlling the folding angle. Furthermore, the transformable and free-standing microelectronic devices based on the three-dimensional-folded mesostructures including epicardial bioelectronics demonstrate the broad utility of these assembly schemes in functional systems.

Structural engineering that overcomes intrinsic limits of bulk materials pivots a cascading collection of new opportunities in biomedical devices, robotic systems, microelectronics, microelectromechanical systems (MEMS), and metamaterials. In particular, morphing mesostructures in three-dimensional not only offers multi-dimensional control to precisely tune materials function on demand, but also breaks the repulsive barriers for heterogeneous materials to coherently integrate, for a leveraged combination of properties beyond those of the individual components.

Many routes to three-dimensional microstructures and nanostructures include ion-beam lithography, layer-by-layer growth, multiphoton lithography, printing-based fabrication, and holographic lithography. While they offer high precision in three-dimensional structural formation, they are often limited in enabling structural morphability for certain high-performance materials such as monocrystalline silicon.

Recently developed methods exploited concepts in self-assembly and mechanically guided assembly to address this limitation with remarkable capability of compatible integration into modern planar technologies and associated thin-film deposition and processing techniques established in the semiconductor industry. However, strong reliance on a planar base or template for anchoring precludes the implementation of those approaches in a broader horizon of applications, especially in making reconfigurable medical devices interfaced with biological tissues (e.g. medical catheters and surgical probes). The development of schemes for realizing morphable three-dimensional mesostructures that can enrich classes of materials and designs of devices found in many forms of electronics, optoelectronics, and microelectromechanical systems remains to be a central breakpoint for new device capabilities and applications. Furthermore, concepts of origami and kirigami, while infiltrated in some schemes, are yet to unleash significant potentials in forming diverse morphable mesostructures in three-dimensional via releasing multi-dimensional freedoms of folding.

As such, various embodiments of the present disclosure provide technical improvements and advantages in the fabrication process of three-dimensional structures, enabling fabricated three-dimensional structures to be morphable and freestanding and to be implemented in a variety of applications. For example, various embodiments of the present disclosure provide strategies, systems, designs, and methods that realize deterministic origami at microscale to establish morphable three-dimensional mesostructures for a broad range of materials including monocrystalline silicon (Si) and metallic membrane as well as their hybrid integration.

Example Fabrications of Three-Dimensional Mesostructures

Referring now to FIG. 1A to FIG. 3, example diagrams and illustrations associated with fabricating example three-dimensional mesostructures in accordance with some embodiments of the present disclosure are provided. In particular, FIG. 1A to FIG. 3 present various assembly methods, systems, and strategies for constructing three-dimensional mesostructures made of, for example but not limited to, monocrystalline silicon (Si) via deterministic micro-folding.

Figure 1B:
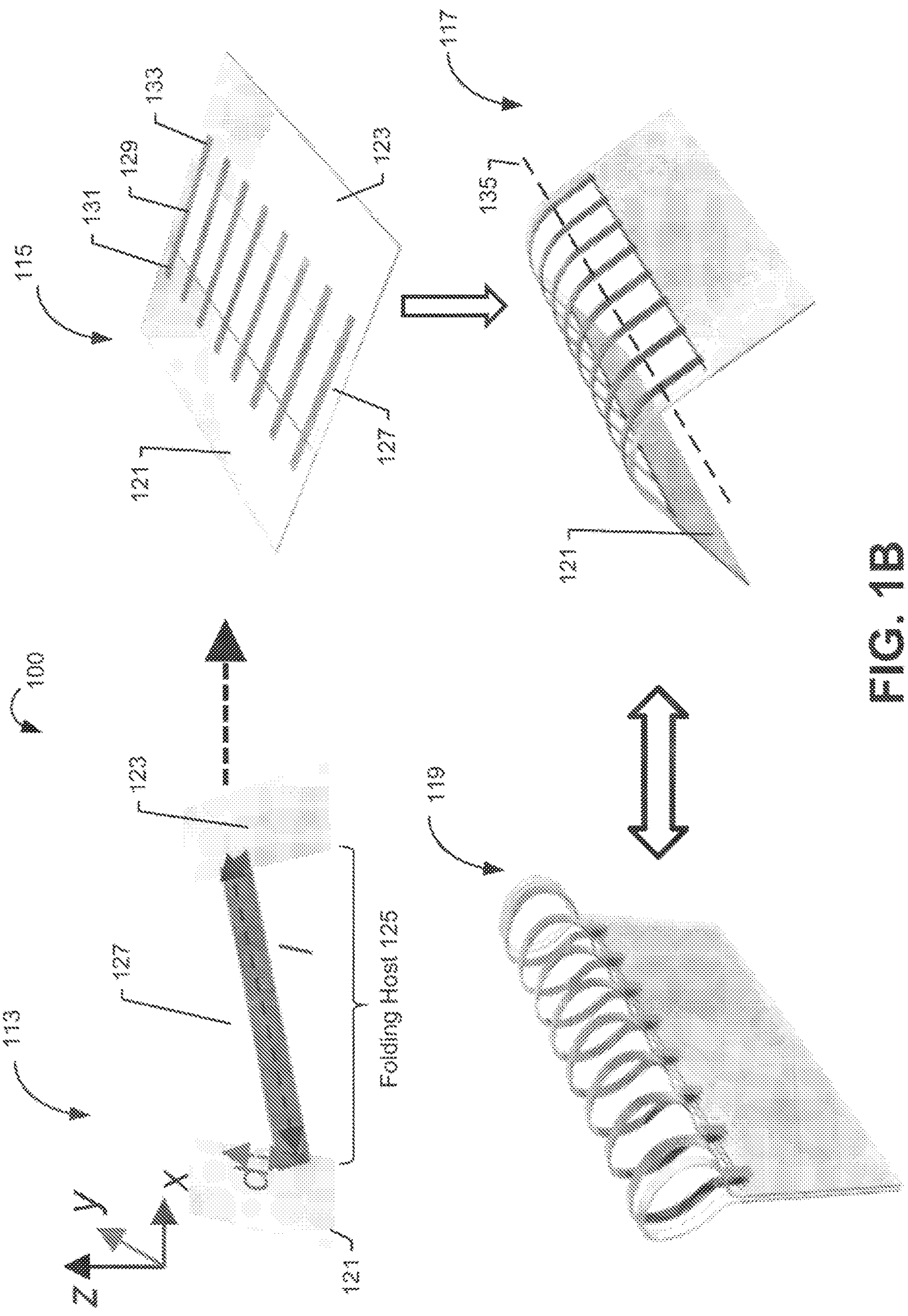
FIG. 1B provides example schematic illustrations highlighting example steps/operations associated with fabricating an example three-dimensional mesostructure in accordance with some embodiments of the present disclosure.

Referring now to FIG. 1A and FIG. 1B, an example method 100 of fabricating an example three-dimensional mesostructure in accordance with some embodiments of the present disclosure is illustrated. In particular, FIG. 1A provides an example flow diagram illustrating example steps/operations of fabricating the example three-dimensional mesostructure, and FIG. 1B provides schematic illustrations highlighting example steps/operations of fabricating the example three-dimensional mesostructure.

In the example shown in FIG. 1A, the example method 100 starts at step/operation 101. In some embodiments, subsequent to step/operation 101, the example 100 proceeds to step/operation 103. At step/operation 103, the example method 100 provides a folding host in an unfolded state.

In the present disclosure, the term “folding host” refers to a device or an apparatus that receives a precursor and transforms the precursor into a three-dimensional mesostructure. For example, an example folding hosts may comprise bonding site portions where the end portions of the precursor can be bonded to, as well as at least one trench portion that provides space for shaping the precursor.

In some embodiments, an example folding host may be fabricated through one or more spin casting processes. Example details associated with fabricating an example folding host are illustrated and described in connection with at least FIG. 2A and FIG. 2B.

Referring now to FIG. 1B, an example folding host 125 is illustrated. In some embodiments, the example folding host 125 comprises a first bonding site portion 121 and a second bonding site portion 123. In the present disclosure, the term “bonding site portion” refers to a portion of a folding host where a precursor end of a precursor can be bonded to or attached to.

In some embodiments, the first bonding site portion 121 and the second bonding site portion 123 are spaced apart from one another. In other words, the folding host 125 defines a trench portion 127 that is positioned between the first bonding site portion 121 and the second bonding site portion 123 of the folding host. In the present disclosure, the term “trench portion” refers to a space between bonding site portions where the precursor can be suspended.

In some embodiments, an example folding host may be associated with one or more states, including, but not limited to, an unfolded state. In some embodiments, when the example folding host is in an unfolded state, the first bonding site portion and the second bonding site portion are coplanar with one another. In FIG. 1B, the example illustration 113 and the example illustration 115 show the example folding host 125 in an unfolded state.

Referring back to FIG. 1A, subsequent to step/operation 103, the example 100 proceeds to step/operation 105. At step/operation 105, the example method 100 binds or bonds a precursor to the first bonding site portion and the second bonding site portion so that the precursor is suspended across the trench portion of the folding host.

In the present disclosure, the term “precursor” refers to a structure based on which a three-dimensional mesostructure can be formed. For example, an example folding host may shape an example precursor into an example three-dimensional mesostructure in accordance with some embodiments of the present disclosure.

In some embodiments, an example precursor may be a two-dimensional mesostructure. In such an example, the example precursor can be characterized based on the length l and/or the width w of the example precursor, while the thickness of the example precursor can be negligible.

In some embodiments, the precursor comprises precursor material. In some embodiments, the precursor material comprises at least one of copper or gold. In some embodiments, the precursor comprises monocrystalline silicon.

While the description above provides example materials of an example precursor, it is noted that the scope of the present disclosure is not limited to the description above. In some examples, an example precursor may comprise one or more additional and/or alternative materials.

In some embodiments, the precursor comprises a first precursor end and a second precursor end that is opposite to the first precursor end. In some embodiments, when the precursor is bound to the first bonding site portion and the second bonding site portion, the first precursor end is bound to the first bonding site portion of the folding host, and the second precursor end is bound to the second bonding site portion of the folding host. In some embodiments, when the precursor is bound to the first bonding site portion and the second bonding site portion, the precursor is suspended across the trench portion of the folding host.

Referring to the example illustration 115 of FIG. 1B, the example precursor 129 is bound to the first bonding site portion 121 and the second bonding site portion 123. In particular, the example precursor 129 comprises a first precursor end 131 and a second precursor end 133 that is opposite to the first precursor end 131. In the example shown in the example illustration 115, the example precursor 129 is suspended across the trench portion 127 of the folding host 125. As such, the example precursor 129 becomes a free-standing two-dimensional precursor.

In some embodiments, an example precursor may be bonded to an example folding host through transfer printing processes based on, for example but not limited to, the precursor materials associated with the example precursor. Additional details associated with the example precursor are described herein, including, but not limited to, those described in connection with at least FIG. 3.

Referring back to FIG. 1A, subsequent to step/operation 105, the example 100 proceeds to step/operation 107. At step/operation 107, the example method 100 shapes the precursor to the three-dimensional mesostructure by transforming the folding host from the unfolded state to a folded state.

In some embodiments, when transforming the folding host from the unfolded state to the folded state, the example method 100 further comprises exerting folding motions on the first bonding site portion and the second bonding site portion along a trench axis of the trench portion.

As described above in connection with FIG. 1B, the example illustration 113 and the example illustration 115 show the example folding host 125 in an unfolded state. The example illustration 117 of FIG. 1B shows the example folding host 125 in a partially folded state, and the example illustration 119 of FIG. 1B shows the example folding host 125 in a fully folded state.

In particular, to transform the folding host 125 from the unfolded state (as shown in the example illustration 113 and the example illustration 115) to the folded state (as shown in the example illustration 119), folding motions can be exerted on the first bonding site portion 121 and the second bonding site portion 123, so that the first bonding site portion 121 and the second bonding site portion 123 can rotate/be folded along a trench axis 135 of the trench portion 127.

As described above, when the precursor 129 is bound to the first bonding site portion 121 and the second bonding site portion 123 of the folding host 125, the precursor 129 is suspended across the trench portion 127 of the folding host 125 between the first bonding site portion 121 and the second bonding site portion 123. As such, when folding motions are exerted on the first bonding site portion 121 and the second bonding site portion 123, the precursor 129 can be shaped into a three-dimensional mesostructure.

Referring back to FIG. 1A, subsequent to step/operation 107, the example 100 proceeds to step/operation 109. At step/operation 109, the example method 100 disengages the three-dimensional mesostructure from the folding host.

In some embodiments, after the precursor is shaped into a three-dimensional mesostructure, the first precursor end can be detached from the first bonding site portion of the folding host, and the second precursor end can be detached from the second bonding site portion of the folding host, so that the three-dimensional mesostructure can be removed from the folding host. As such, the example method 100 provides an example of fabricating a freestanding three-dimensional mesostructure.

Referring back to FIG. 1A, subsequent to step/operation 109, the example 100 proceeds to step/operation 111 and ends.

As described above in connection with FIG. 1A, FIG. 1B illustrates an example micro-folding assembly of three-dimensional microstructures of monocrystalline silicon. In particular, FIG. 1B provides schematic illustrations highlighting example processes of the micro-folding assembly.

For example, the example illustration 113 and the example illustration 115 illustrate forming a hinge structure comprising a two-dimensional soft precursor and a rigid folding host (for example, comprising PLGA/PDMS hollow sheet) through a transfer printing process, additional details of which are described in connection with at least FIG. 3. As shown in the example illustration 113, the parameters/and d denote the length of the silicon ribbon and the distance between the first bonding site portion and the second bonding site portion along the y-axis, respectively, defining the primary dimensional parameters of the structural integration for the hinge structure.

As another example, the example illustration 117 illustrates partially folding the folding host to form various transitional states of three-dimensional microstructures. In some embodiments, the inclination angle θ of the folding-host sheet defines the degree of partial folding. Additional details associated with the inclination angle θ are described in connection with at least FIG. 4A.

As another example, the example illustration 119 illustrates full folding (where inclination angle θ is 90 degrees) to form the final state of three-dimensional microstructures. As shown in the example illustration 119, the three-dimensional microstructures are suspended on the edge of the folding host.

By strategically bending the folding host at various degrees of angle, various embodiments of the present disclosure translate the origami effect to the guest two-dimensional precursor into a specially engineered three-dimensional mesostructure. In some embodiments, such host-guest coevolution precisely alters structural reconfigurations through macroscopic folding registrations, angles, and directions of the host to navigate folding trajectories of the microscopic guest precursor towards a broad range of geometrically distinct mesostructures in three dimensions.

Example Fabrications of Folding Hosts

Figure 2A:
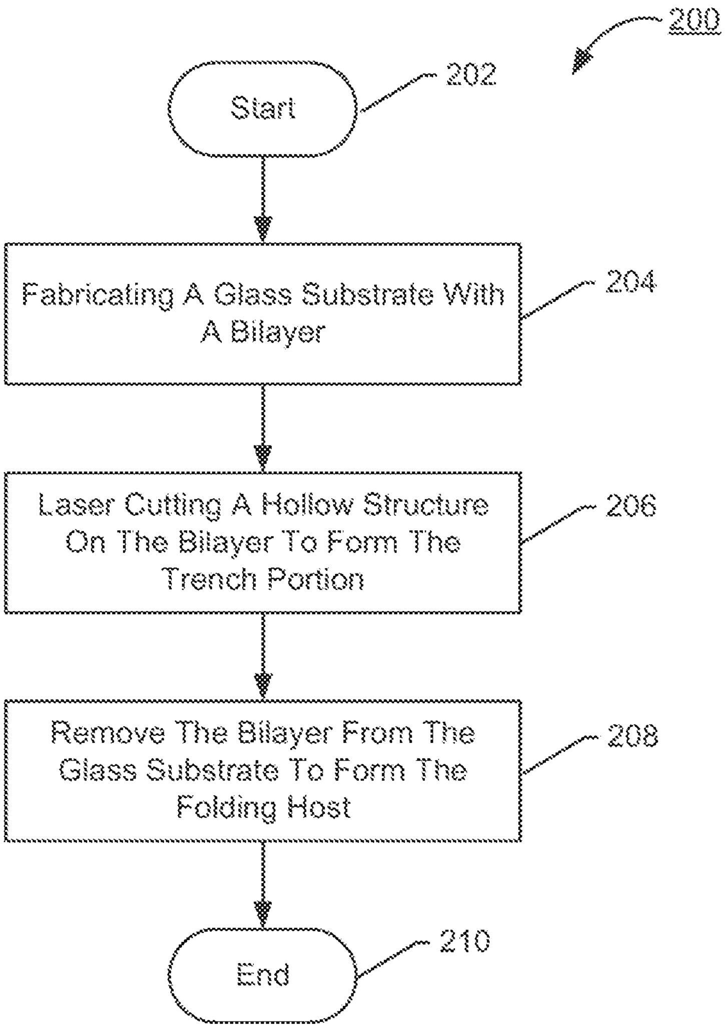
FIG. 2A provides an example flow diagram illustrating an example method of fabricating an example folding host in accordance with some embodiments of the present disclosure.
Figure 2B:
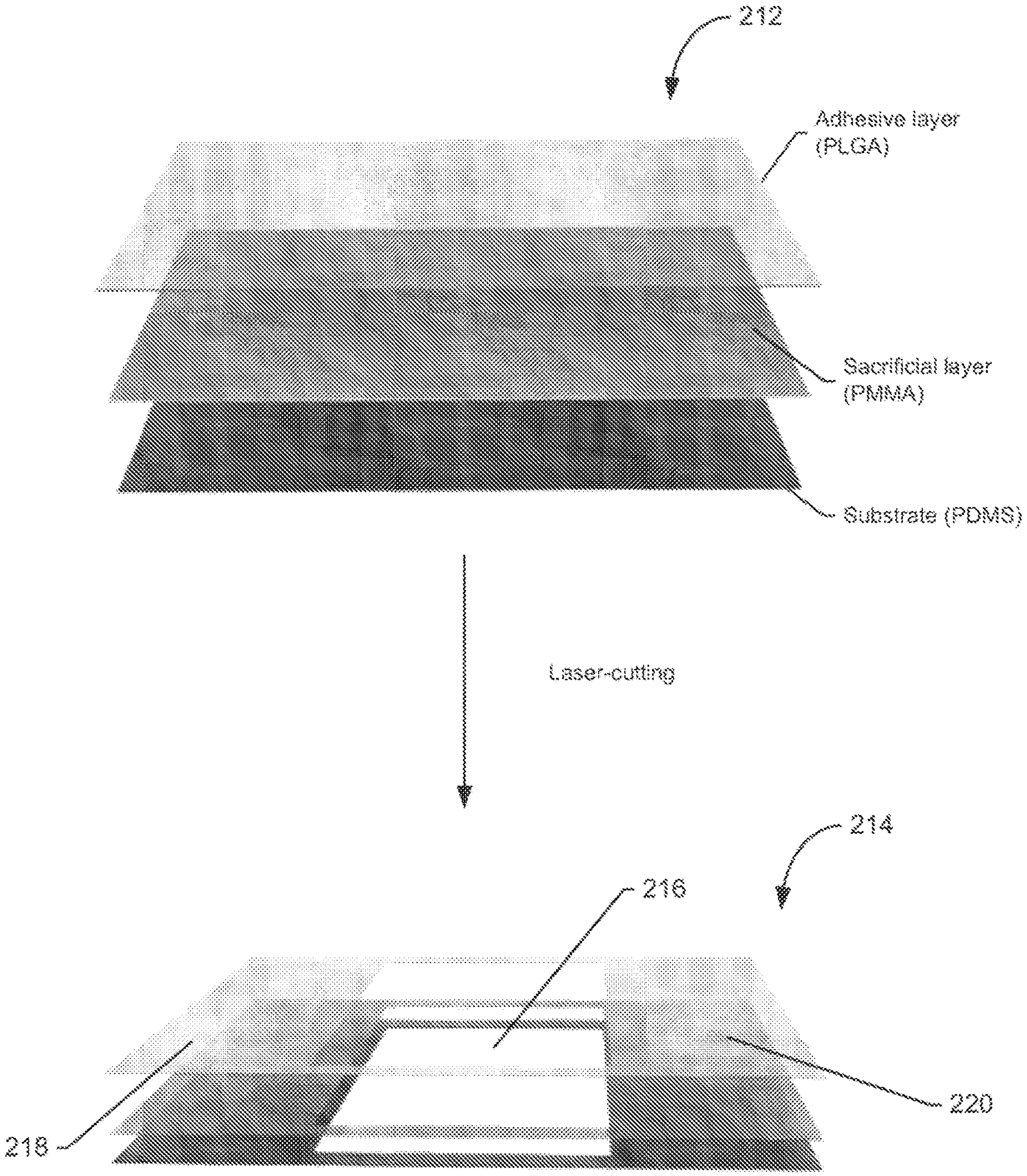
FIG. 2B provides example schematic illustrations highlighting example steps/operations associated with fabricating an example folding host in accordance with some embodiments of the present disclosure.

Referring now to FIG. 2A and FIG. 2B, an example method 200 of fabricating an example folding host in accordance with some embodiments of the present disclosure is illustrated.

In the example shown in FIG. 2A, the example method 200 starts at step/operation 202. In some embodiments, subsequent to step/operation 202, the example 200 proceeds to step/operation 204. At step/operation 204, the example method 200 comprises fabricating a glass substrate with a bilayer comprising polydimethylsiloxane (PDMS) and poly lactic-co-glycolic acid (PLGA).

In some embodiments, the glass substrate with the bilayer may be fabricated through one or more spin casting processes. In some embodiments, an example spin casting process may utilize centrifugal forces to bond one layer of material to another layer of material.

In some embodiments, when fabricating the glass substrate with the bilayer, the example method 200 comprises spin casting a PDMS layer on the glass substrate, and then spin casting a PLGA layer on the PDMS layer.

For example, the fabrication of an engineered folding host began with spin casting of a thin layer of PDMS onto a glass. In some embodiments, the PDMS comprises Sylgard 182 silicone elastomer, with a mixing ratio 1:10 and cured at 60° C. vacuum for 1 hour. In some embodiments, the PDMS layer is 5 μm in thickness. Subsequently, the fabrication of the engineered folding host includes spin casting of a second layer of PLGA onto the previously formed PDMS as an adhesive layer. In some embodiments, the PLGA layer is 1 μm in thickness.

Referring now to FIG. 2B, the example illustration 212 shows an example glass substrate with a bilayer that comprises a PDMS layer and a PLGA layer.

Referring back to FIG. 2A, subsequent to step/operation 204, the example 200 proceeds to step/operation 206. At step/operation 206, the example method 200 comprises laser cutting a hollow portion on the bilayer to form the trench portion for the folding host.

As described above, an example folding host in accordance with some embodiments of the present disclosure comprises a trench portion where a precursor can be suspended. In some embodiments, the example method 200 utilizes a laser to cut a hollow portion on the bilayer that comprises the PDMS layer and the PLGA layer. As such, the hollow portion on the bilayer that is formed through laser cutting corresponds to the trench portion for the folding host.

Referring now to FIG. 2B, the example illustration 214 shows an example hollow portion 216 on the bilayer.

Referring back to FIG. 2A, subsequent to step/operation 206, the example 200 proceeds to step/operation 208. At step/operation 208, the example method 200 comprises removing the bilayer from the glass substrate to form the folding host.

In some embodiments, the example method 200 peels the bilayer that comprises the PDMS layer and the PLGA layer away from the glass substrate to yield a thin folding host. As described above, the example method 200 utilizes laser cutting techniques to form a hollow portion. In some embodiments, when the bilayer (that comprises the PDMS layer and the PLGA layer) is peeled away from the glass substrate, the example hollow portion becomes the trench portion of the folding host.

Referring to FIG. 2B, the example illustration 214 shows an example folding host that comprises a first bonding site portion 218, a second bonding site portion 220, and a trench portion formed by the hollow portion 216 through laser cutting.

Referring back to FIG. 2A, subsequent to step/operation 208, the example 200 proceeds to step/operation 210 and ends.

Example Fabrications of Precursors

Figure 3:
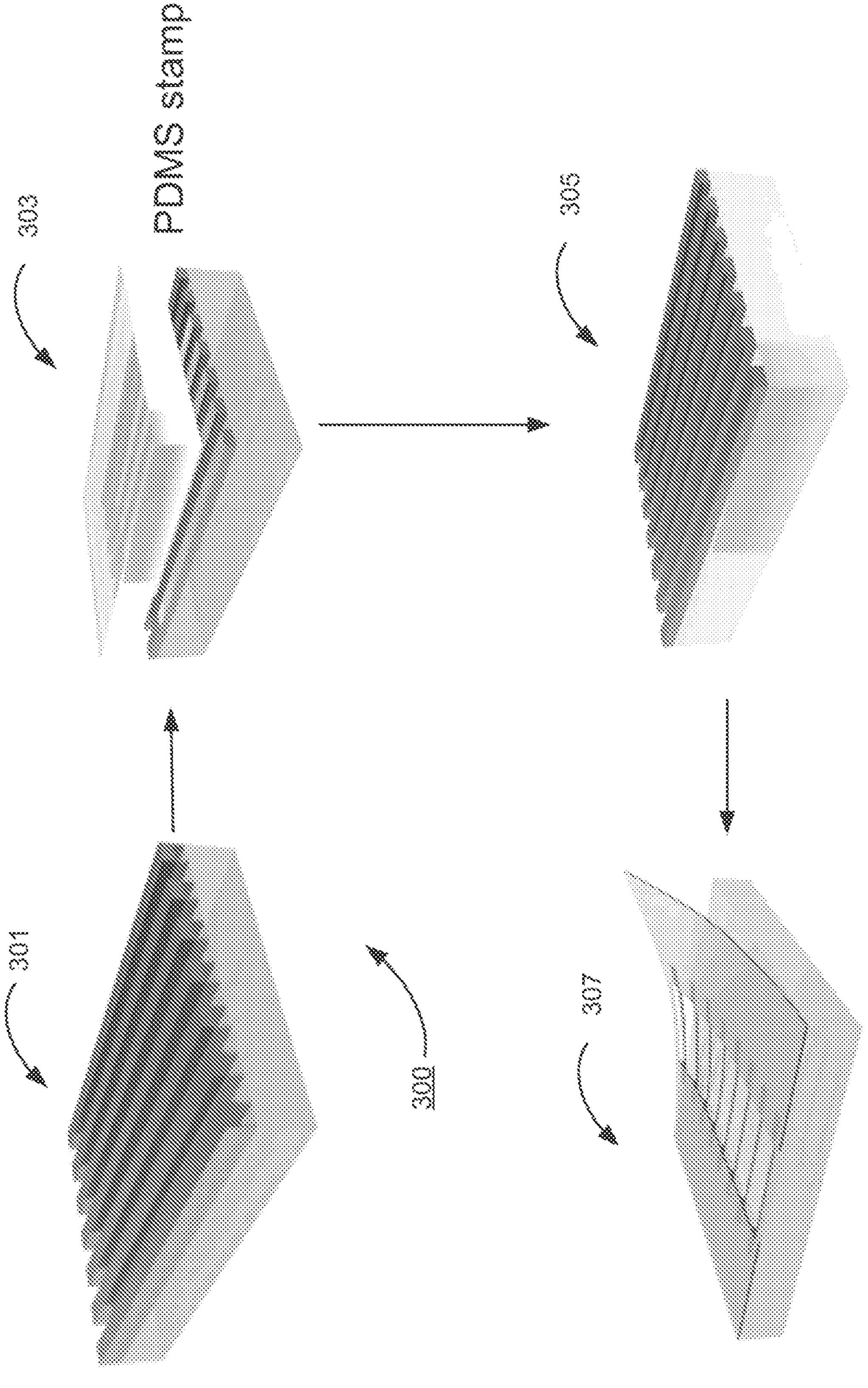
FIG. 3 provides example schematic illustrations showing example steps/operations associated with bonding an example precursor to an example folding host in accordance with some embodiments of the present disclosure.

Referring now to FIG. 3, schematic illustrations highlighting example steps/operations of preparing/fabricating precursors and bonding precursors to folding hosts in accordance with some embodiments of the present disclosure are illustrated. In particular, FIG. 3 provides an example schematic illustration of an example method 300 showing the transfer printing process to produce ribbons of monocrystalline silicon (Si) in accordance with some embodiments of the present disclosure.

In the example shown in FIG. 3, the example method of bonding a precursor to a folding host begins at the example illustration 301. As shown in the example illustration 301, the example method comprises defining silicon ribbons on silicon-on-insulator (SOI) substrate.

In some embodiments, the example method 300 begins with planar microfabrication or nanofabrication of an array of two-dimensional filamentary silicon ribbons as shown in the example illustration 301. In some embodiments, the thickness of the silicon ribbon is 200 nm. In some embodiments, the width of the silicon ribbon is 50 μm. In some embodiments, the array periodicity associated with the silicon ribbon is 250 μm.

In some embodiments, the precursor (such as, but not limited to, silicon ribbons) can be formed on a device layer of a silicon-on-insulator (SOI) substrate. For example, the silicon ribbons can be lithographically defined on the SOI substrate.

Continuing from the silicon ribbons example above, an example preparation method of defining silicon ribbons on SOI substrate may begin with patterning of two-dimensional precursors with the device layer of a SOI wafer by photolithography and reactive ion etching. In some embodiments, the thickness of device-layer silicon of the SOI wafer is 200 nm. In some embodiments, the photolithography process may implement Karl Suss MA/BA 6 aligner. In some embodiments, the reactive ion etching process may utilize RIE, SF6 plasma etching, Alcatel AMS 100 Deep Reactive Ion Etcher, and/or the like.

In some embodiments, the example preparation method of defining silicon ribbons on SOI substrate may comprise causing an immersion in buffered oxide etch (BOE) to partially undercut the buried silicon dioxide ($SiO_2$) layer from the exposed regions and slightly from under of the edges of the patterns at their periphery.

In some embodiments, the example preparation method of defining silicon ribbons on SOI substrate comprises spin casting and utilizing photolithography formed patterns of a photoresist as anchor to tether the silicon structure to the underlying substrate. In some embodiments, the photoresist may be in the form of a S1805 series photoresist with 0.5 μm in thickness. In some embodiments, the example preparation method of defining silicon ribbons on SOI substrate comprises causing an immersion in hydrofluoric acid (HF) to fully undercut the $SiO_2$ layer.

In some embodiments, a soft, thin film of PLGA with a lithographically defined trench in a precisely controlled geometry serves as a folding host that guides the microfolding assembly process. In some embodiments, the thin film of PLGA has a thickness of 10 μm In some embodiments, subsequent to the example illustration 301, the example method of bonding a precursor to a folding host proceeds to the example illustration 303. As shown in the example illustration 303, the example method comprises placing a PDMS stamp onto fully undercutted silicon ribbons as described above.

In some embodiments, subsequent to the example illustration 303, the example method of bonding a precursor to a folding host proceeds to the example illustration 305. As shown in the example illustration 305, the example method comprises retrieving silicon ribbons onto the PDMS stamp.

As provided in the example illustration 303 and the example illustration 305, the PDMS stamp can retrieve precursors from the SOI substrate.

In some embodiments, subsequent to the example illustration 305, the example method of bonding a precursor to a folding host proceeds to the example illustration 307. As shown in the example illustration 307, the example method comprises transferring precursors (such as silicon ribbons) onto the folding host by, for example, but not limited to, printing precursors (such as silicon ribbons) onto a folding host.

In some embodiments, transfer printing of the two-dimensional silicon ribbons at temperature 70° C. with aligned registration onto the folding host leads to the silicon ribbons suspended across the trench. In some embodiments, relatively weak van der Waals forces dictate interfacial interactions between the silicon precursor and the PLGA film, thus allowing undisturbed disengagement of the folding host upon completion of the microfolding process to form free-standing three-dimensional mesostructures.

In some embodiments, retrieving the two-dimensional silicon ribbons onto a slab of PDMS and then transferring them onto a pre-designed folding host allows controlled folding of the host base to a well-defined angle via a mechanical stage to complete the three-dimensional assembly process.

In various embodiments of the present disclosure, an example two-dimensional precursor may comprise one or more materials that include, but not limited to, monocrystalline silicon (Si), Si/PLGA, copper, gold, copper-coated and gold-coated polyimide (PI), and/or the like. While the description above provides example preparation methods of three-dimensional mesostructures of monocrystalline silicon, it is noted that the scope of the present disclosure is not limited to the description above. In some embodiments, additional and/or alternative preparation methods can be implemented to prepare three-dimensional mesostructures comprising other materials.

For example, an example preparation method of three-dimensional mesostructures of Si/PLGA in accordance with some embodiments of the present disclosure is provided.

In some embodiments, the example preparation method of three-dimensional mesostructures of Si/PLGA comprises defining two-dimensional patterned silicon on a SOI wafer using photolithography followed by reactive ion etching as described above.

In some embodiments, the example preparation method comprises retrieving silicon precursors onto a PDMS stamp and transferring them onto a PLGA film. In some embodiments, the PLGA film is 10 μm in thickness.

In some embodiments, the preparation of the PLGA film began with spin-coating a solution of PLGA onto a hydrophobic surface of the PDMS substrate. In some embodiments, the solution of PLGA has 5 wt % in ethyl acetate. Subsequent to spin-coating the solution of PLGA onto the hydrophobic surface of PDMS substrate, the preparation of the PLGA film is followed by slow drying the PLGA film at a predetermined temperature (such as, but not limited to, 90° C.) for a predetermined amount of time (such as, but not limited to, 10 minutes), so as to facilitate the bonding with silicon precursor during the transfer process.

In some embodiments, the PLGA film may be cured in a vacuum environment at 200° C. for 2 hours. In some embodiments, the patterns of PLGA film can be defined by laser cutting and then were transferred onto a pre-designed folding host using a PDMS stamp.

In some embodiments, a mechanical stage can be implemented to allow controlled folding of the host base to a well-defined angle to complete the three-dimensional assembly process.

Additionally, or alternatively, an example preparation method of three-dimensional mesostructures of copper, gold, copper-coated and gold-coated polyimide (PI) in accordance with some embodiments of the present disclosure is provided.

In some embodiments, the preparation method began with forming a precursor layer by depositing the precursor material (such as, but not limited to, copper or gold) on a sacrificial layer of a silicon wafer substrate.

For example, the preparation method obtains thin films of precursor material (such as, but not limited to, copper or gold) using a sputter deposition system onto a silicon wafer coated with silicon oxide as a sacrificial layer. In some embodiments, the thicknesses of copper or gold range from 200 nm to 1 μm. In some embodiments, silicon wafer coated with silicon oxide is 300 nm in thickness.

In some embodiments, the example preparation method forms the precursor on the precursor layer.

For example, the example preparation method provides photolithograph and wet etching defined patterns of the two-dimensional precursors. In some embodiments, the example preparation method comprises immersion in hydrofluoric acid (HF) for a predetermined period of time (such as, but not limited to, 4 hours) to fully undercut the sacrificial layer and allow retrieval of the two-dimensional precursors using a PDMS stamp.

In some embodiments, the example preparation method of the two-dimensional precursors of copper-coated or gold-coated PI films relied on direct deposition of copper or gold onto a thin film of PI. In some embodiments, the thin film of PI is 5 μm in thickness. Then, the example preparation method comprises transfer printing of the two-dimensional precursors onto a folding host with alignment prepared for micro-folding assembly.

In some embodiments, the example preparation method comprises retrieving the precursor by a PDMS stamp and transferring the precursor onto the folding host.

In some embodiments, the example preparation method provides a mechanical stage that allows controlled folding of the host base to a well-defined angle to complete the three-dimensional assembly process.

Example Parameters of Fabricating Three-Dimensional Mesostructures

Referring now to FIG. 4A to FIG. 32, various example images and diagrams associated with three-dimensional mesostructures in accordance with some embodiments of the present disclosure are illustrated. In particular, FIG. 4A to FIG. 32 illustrate various example parameters associated with fabricating three-dimensional mesostructures that can be controlled for optimum results.

Figure 4A:
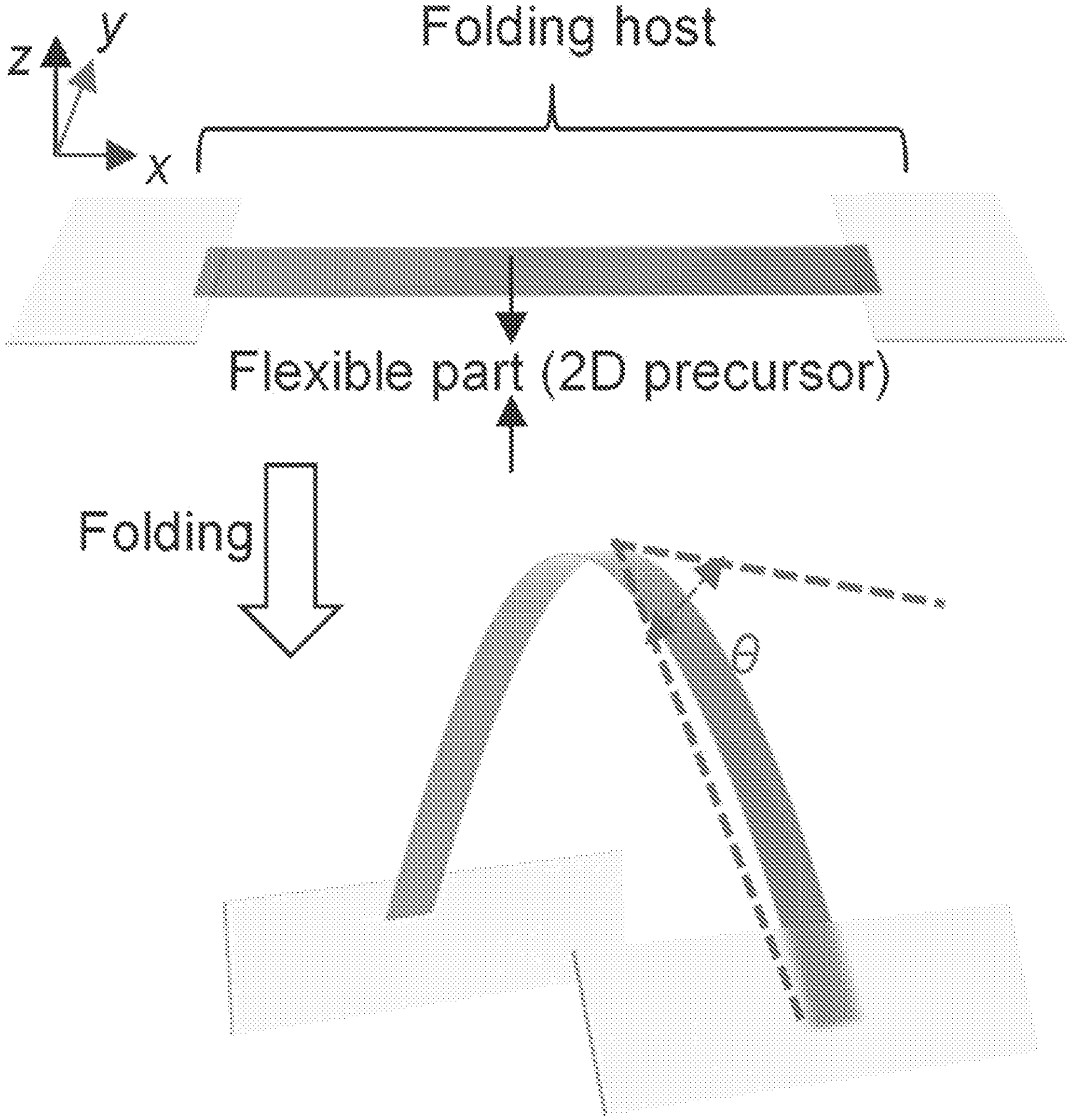
FIG. 4A provides example schematic illustrations of an example precursor bonded to an example folding host in accordance with some embodiments of the present disclosure.

It is noted that, besides the intrinsic fabrication parameters including the length l, width w and thickness t of the silicon ribbon, FIG. 1B above and FIG. 4A define two other primary dimensional parameters that affect the resultant three-dimensional configuration, namely the distance (labeled as d, along y-axis) between two bonding sites and the folding angle (the inclination angle θ) of the precursor during folding), respectively. In some embodiments, the folding host allows additional dimensional freedom of reconfiguration via the folding angle to reversibly alter the three-dimensional mesostructures (such as, but not limited to, as shown in the example illustration 117 and/or the example illustration 119 of FIG. 1B described above).

Figure 4B:
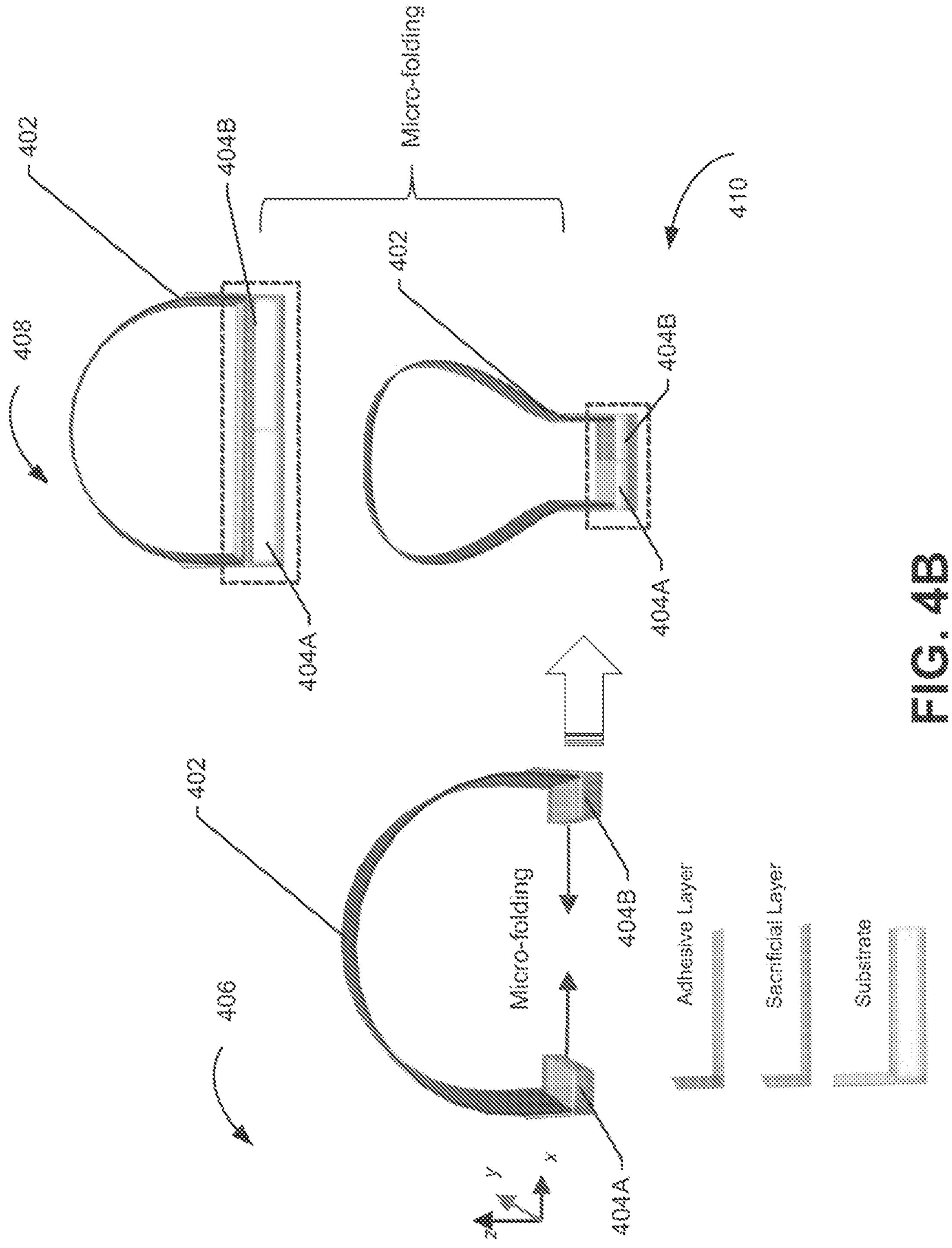
FIG. 4B illustrates an example precursor transforming from an example initial state to example partially folded states in accordance with some embodiments of the present disclosure.

FIG. 4B illustrates an example precursor 402 transforming from an example initial state 406 to the example partially folded state 408 and/or to the example partially folded state 410 in accordance with some embodiments of the present disclosure.

Similar to those described above, the example precursor 402 is attached to the first bonding site portion 404A and the second bonding site portion 404B. In some embodiments, each of the first bonding site portion 404A and the second bonding site portion 404B comprises an adhesive layer, a sacrificial layer, and a substrate.

In the example shown in FIG. 4B, the example precursor 402 is transferred to the example partially folded state 408 and/or to the example partially folded state 410 by causing the first bonding site portion 404A and the second bonding site portion 404B to be positioned on the same plane and to receive a translation motion (instead of a folding motion) so that they are moving towards one another. As shown in FIG. 4B, the length of the first bonding site portion 404A and the length of the second bonding site portion 404B can be determine or adjusted to produce different inclination angles θ of the partially folded example precursor 402.

Figures 4C, 4D:
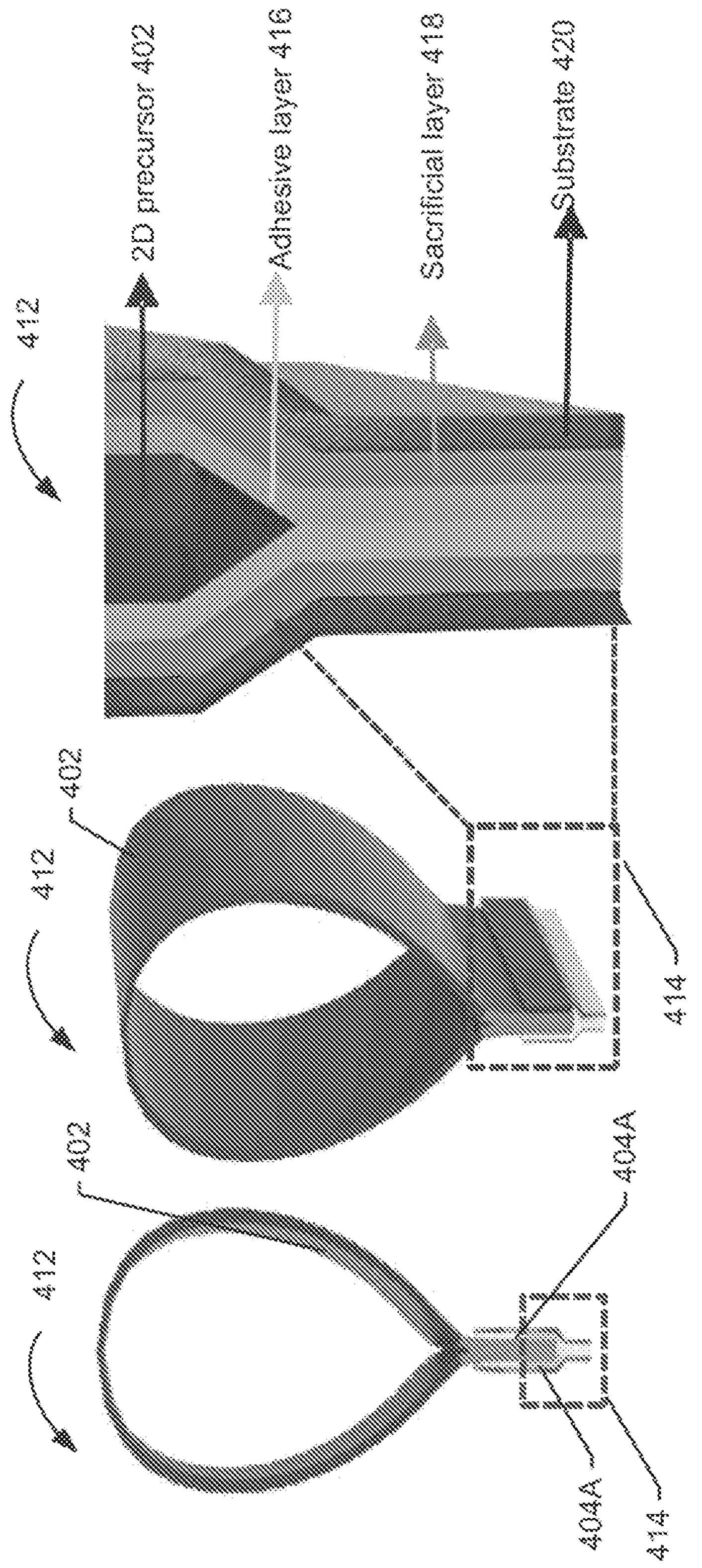
FIG. 4C illustrates an example precursor in an example fully folded state in accordance with some embodiments of the present disclosure.
FIG. 4D illustrates an example zoomed view of an example precursor in an example fully folded state in accordance with some embodiments of the present disclosure.

Referring now FIG. 4C and FIG. 4D, the example precursor 402 in an example fully folded state 412 in accordance with some embodiments of the present disclosure is illustrated. In the example shown FIG. 4C, the example precursor 402 is transferred to the example fully folded state 412 by exerting a rotating, folding motion to the first bonding site portion 404A and the second bonding site portion 404B. FIG. 4D further illustrates an example zoomed portion 414 as shown in FIG. 4C. In the example fully folded state 412 shown in FIG. 4D, the example zoomed portion 414 comprises the two-dimensional precursor 402 positioned in the central portion, which is covered by the adhesive layer 416. The adhesive layer 416 is covered by the sacrificial layer 418. The sacrificial layer 418 is covered by the substrate 420

FIG. 5, FIG. 6A, FIG. 6B, FIG. 6C, FIG. 7A, FIG. 7B, FIG. 7C, FIG. 8A, FIG. 8B, and FIG. 8C illustrate example SEM images of suspended three-dimensional silicon hoops at a fully folded state (θ=90°) transformed from two-dimensional filamentary silicon ribbons. In particular, the silicon ribbons have a ribbon width w of 50 μm, a thickness t of 200 nm, a length l of 1500 μm, and a folding parameter d of 0 μm.

FIG. 5 to FIG. 8C illustrate various technical advantages and benefits of the present disclosure. In particular, the resultant three-dimensional silicon structures as shown in FIG. 5 to FIG. 8C are suspended from an edge, which differ qualitatively from in-plane buckling patterns using a pre-strained elastic substrate and are challenging to construct using three-dimensional printing technology.

Figure 5:
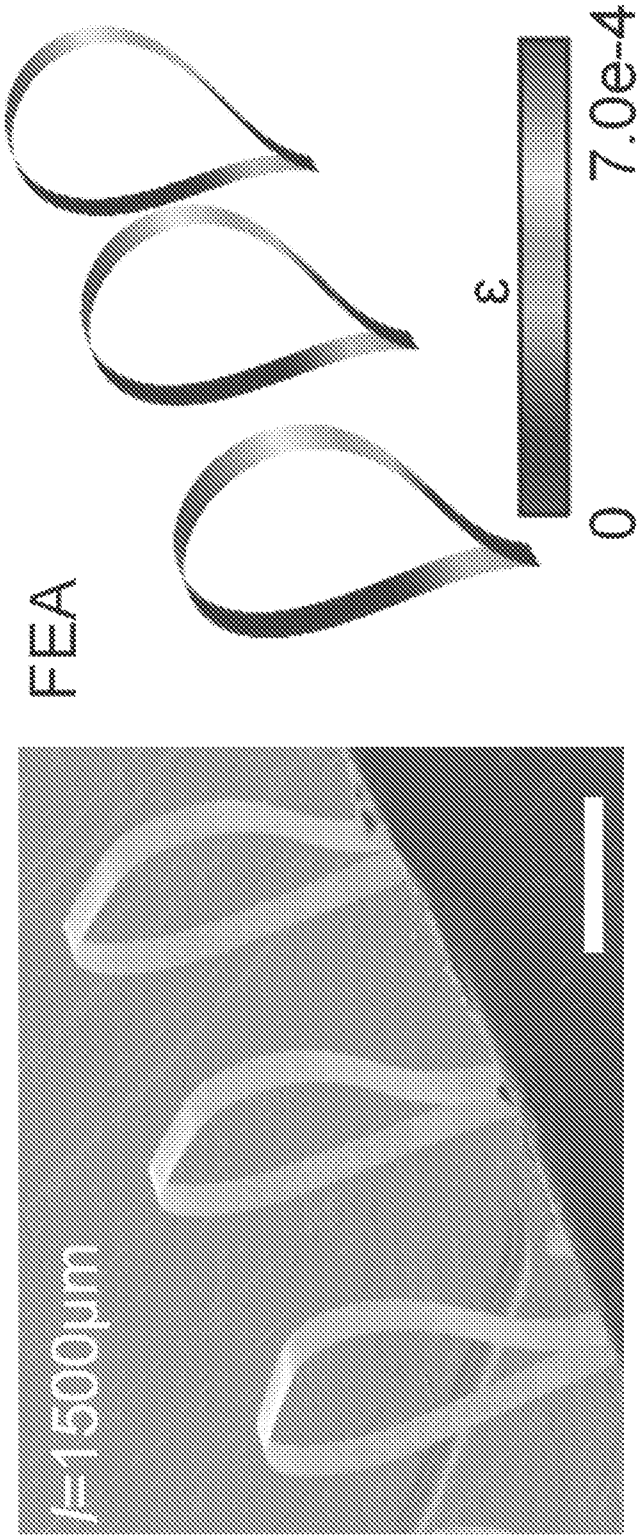
FIG. 5 provides an example scanning electron microscope (SEM) image and corresponding example finite-element analysis (FEA) results of an example three-dimensional mesostructure in accordance with some embodiments of the present disclosure.
Figure 6A:
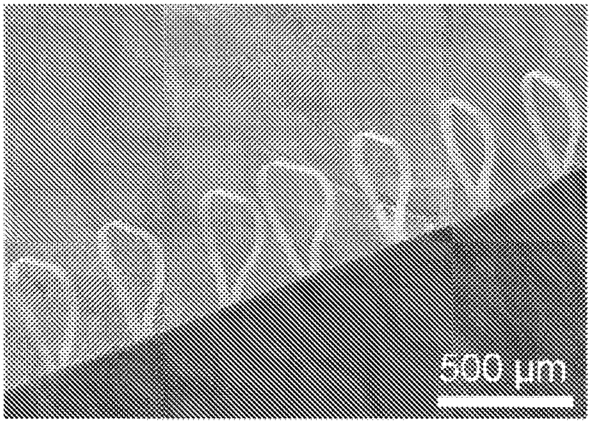
FIG. 6A, FIG. 6B, and FIG. 6C provide SEM images of example side views of example three-dimensional mesostructures that are achieved by deterministic microfolding in accordance with some embodiments of the present disclosure.
Figure 6B:
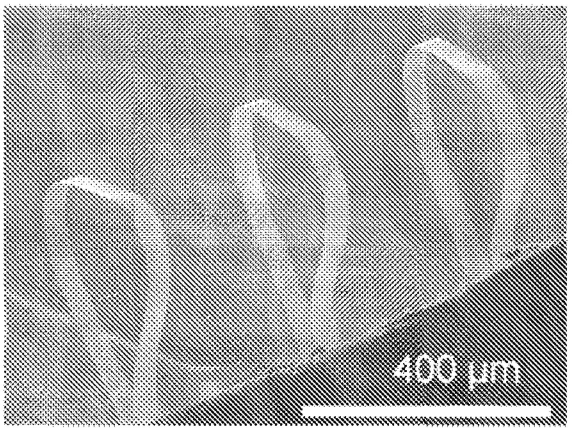
Figure 6C:
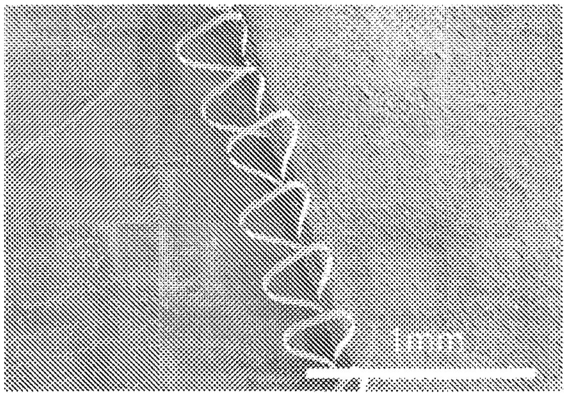
Figure 7A:
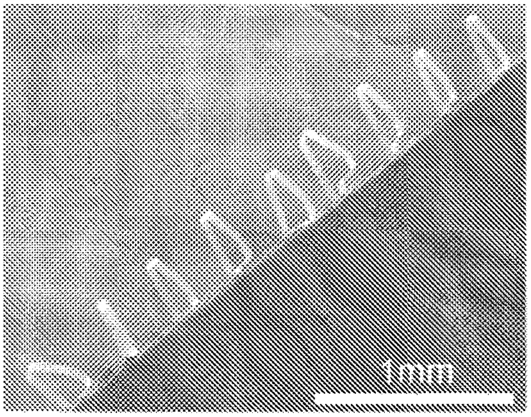
FIG. 7A, FIG. 7B, and FIG. 7C provide SEM images of example top views of example three-dimensional mesostructures that are achieved by deterministic microfolding in accordance with some embodiments of the present disclosure.
Figure 7B:
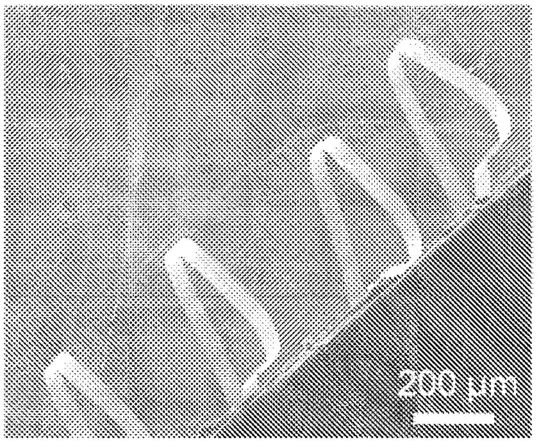
Figure 7C:
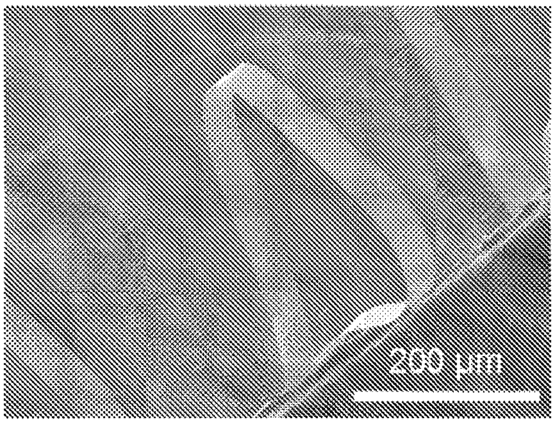
Figure 8A:
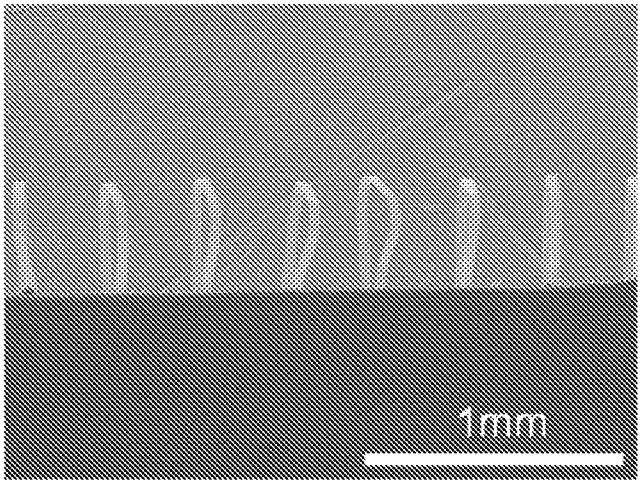
FIG. 8A, FIG. 8B, and FIG. 8C provide SEM images of example front views of example three-dimensional mesostructures that are achieved by deterministic microfolding in accordance with some embodiments of the present disclosure.
Figure 8B:
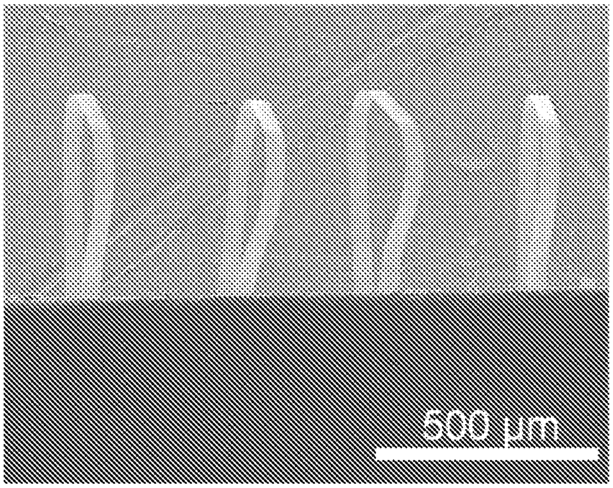
Figure 8C:
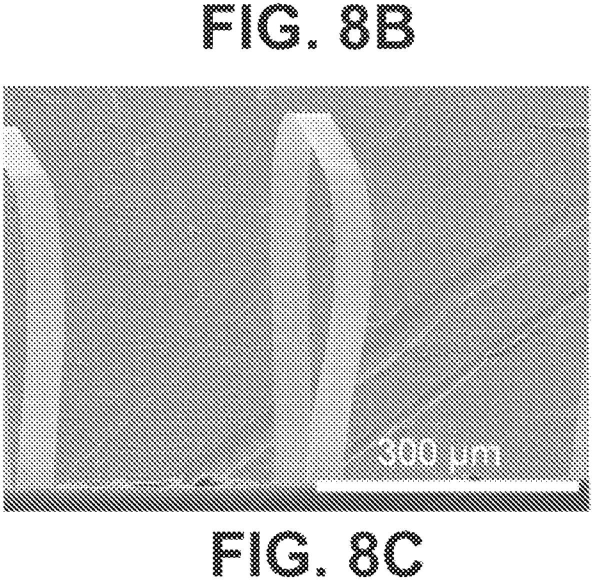

Based on the finite element analysis as shown in FIG. 5, the deformation and the corresponding strain distribution of the three-dimensional silicon structures formed via the deterministic folding process in accordance with some embodiments of the present disclosure can be predicted through, for example but not limited to, an example static finite element analysis.

In an example static finite element analysis in accordance with some embodiments of the present disclosure, three-dimensional finite element analyses (FEA) in commercial software ABAQUS can be utilized to predict the microfolding process of two-dimensional precursors with different patterns, dimensions and materials, so as to guide the microstructural designs for the deterministic microfolding strategy and to establish the scaling law for predicting strain level in the meso-structures.

In some embodiments, four-node shell elements (S4R) with second-order precision and enhanced hourglass control can be used to simulate the thin meso-structures. In some embodiments, convergence tests of the mesh size can be performed to ensure accuracy. In some embodiments, the elastic modulus (E) and Poisson's ratio (n) used in the simulations were as follows:

$$E_{Si} = 179 \text{ } G\text{Pa and } v_{Si} = 0.28 \text{ for Si,}$$

-continued $$E_{Cu} = 119 \text{ } G\text{Pa and } v_{Cu} = 0.33 \text{ for Cu, and}$$

$$E_{Au} = 79.5 \text{ } G\text{Pa and } v_{Au} \text{ for Au.}$$

Various drawings of the present disclosure (including, but not limited to, at least FIG. 5, FIG. 10, FIG. 11, FIG. 16, FIG. 18, FIG. 24, FIG. 26, and FIG. 27) demonstrate an excellent agreement between experiments and FEA simulations.

Figure 9:
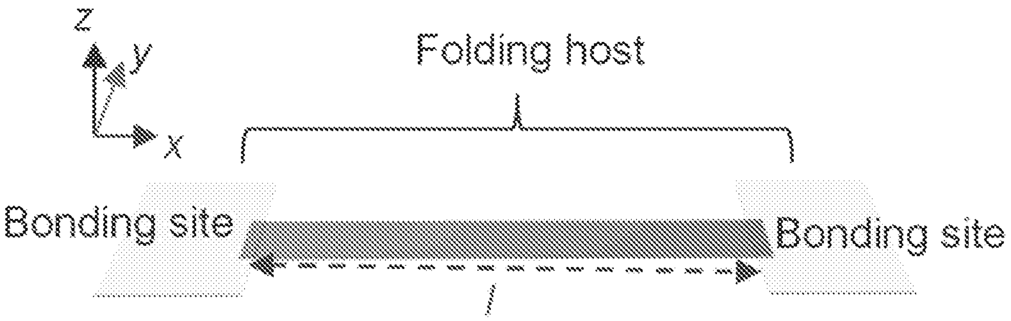
FIG. 9 provides an example schematic illustration indicating an example definition of a fabrication parameter/for fabricating an example three-dimensional mesostructure in accordance with some embodiments of the present disclosure.
Figure 10:
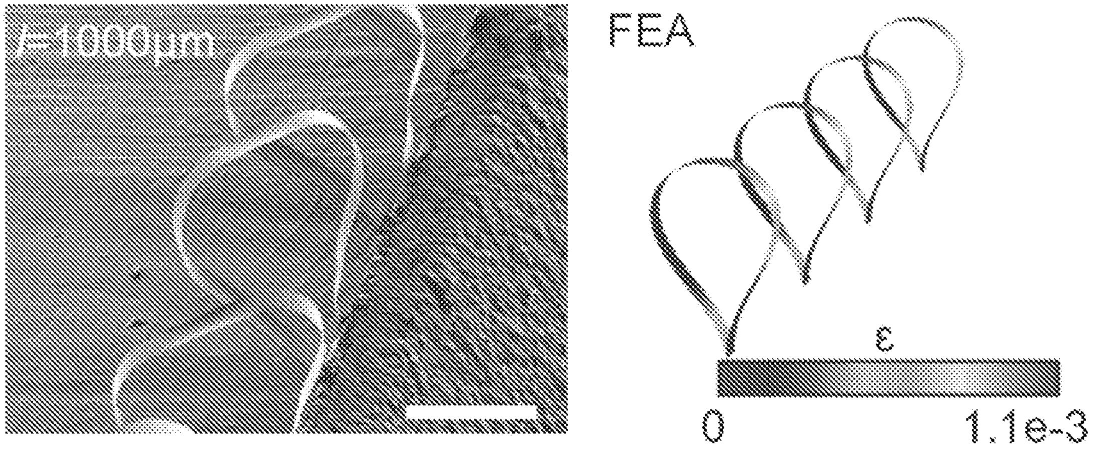
FIG. 10 provides an example SEM image and corresponding example FEA results of the example three-dimensional mesostructures in accordance with some embodiments of the present disclosure.
Figure 11:
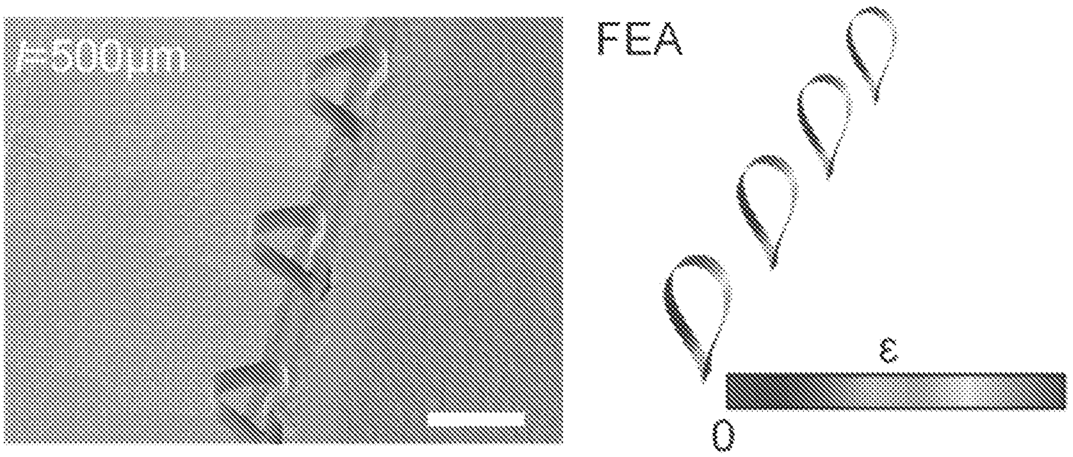
FIG. 11 provides an example SEM image and corresponding example FEA results of the example three-dimensional mesostructures in accordance with some embodiments of the present disclosure.
Figure 12A:
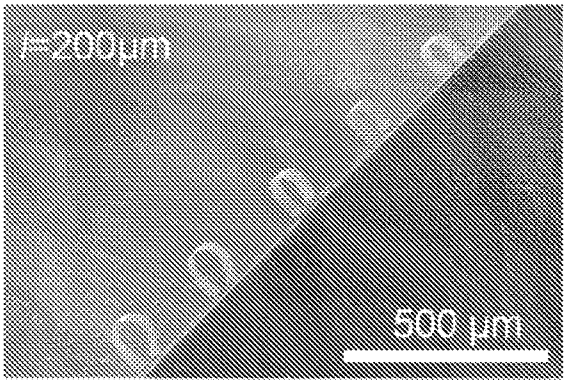
FIG. 12A provides an example SEM image of example three-dimensional mesostructures in accordance with some embodiments of the present disclosure, FIG. 12B provides an example SEM image of an example three-dimensional mesostructure in accordance with some embodiments of the present disclosure.
Figure 12B:
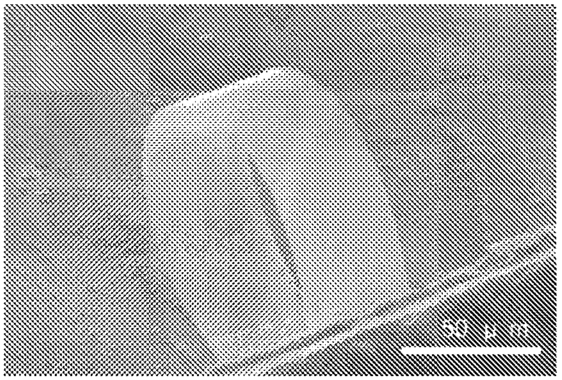
FIG. 12C provides an example SEM image of example three-dimensional mesostructures in accordance with some embodiments of the present disclosure.
FIG. 12D provides an example SEM image of an example three-dimensional mesostructure in accordance with some embodiments of the present disclosure.
Figure 12C:
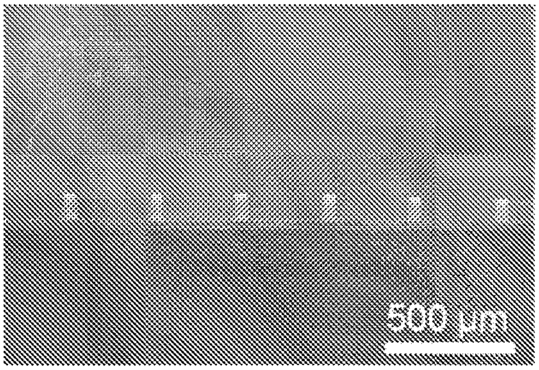
Figure 12D:
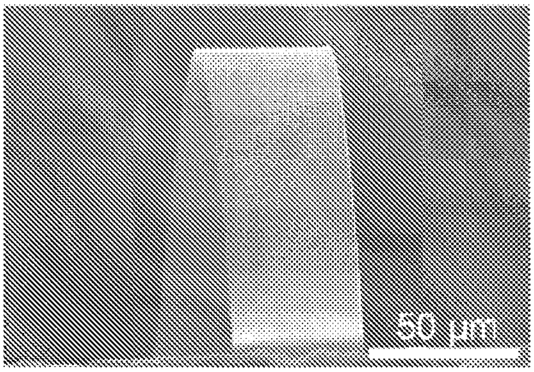
Figure 13A:
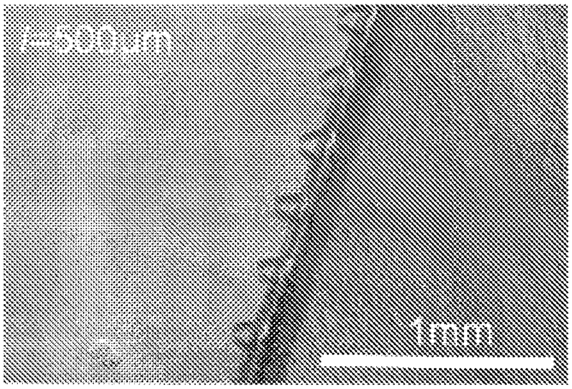
FIG. 13A provides an example SEM image of example three-dimensional mesostructures in accordance with some embodiments of the present disclosure.
Figure 13B:
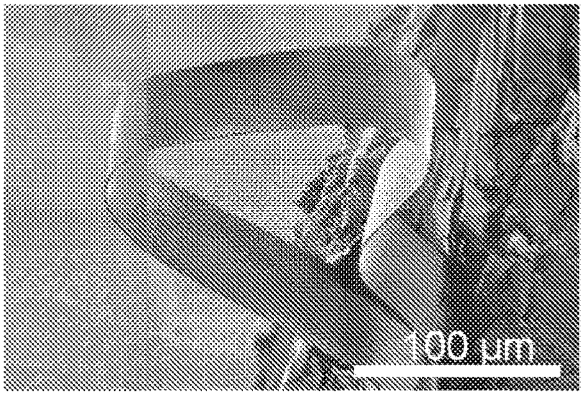
FIG. 13B provides an example SEM image of an example three-dimensional mesostructure in accordance with some embodiments of the present disclosure.

FIG. 9 illustrates the length parameter of the precursor l that can enable controllable modulation of curvatures of the resultant three-dimensional silicon hoops, as shown in FIG. 5, FIG. 10, and FIG. 11.

In some embodiments, aligning two-dimensional silicon ribbons vertically to the trench edge of a folding host enables precise control of curvatures of the resultant three-dimensional Si hoops through varying the length l of the precursor. For example, FIG. 5 illustrates an example where the length l of the precursor is 1500 μm. FIG. 10 illustrates an example where the length l of the precursor is 1000 μm. FIG. 11 illustrates an example where the length l of the precursor is 500 μm.

Figure 14A:
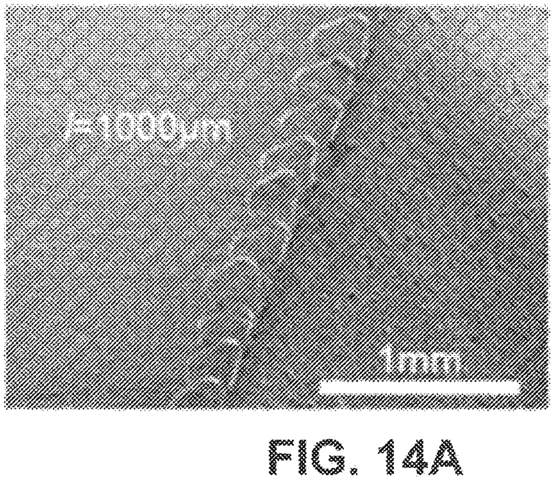
FIG. 14A provides an example SEM image of example three-dimensional mesostructures in accordance with some embodiments of the present disclosure.
Figure 14B:
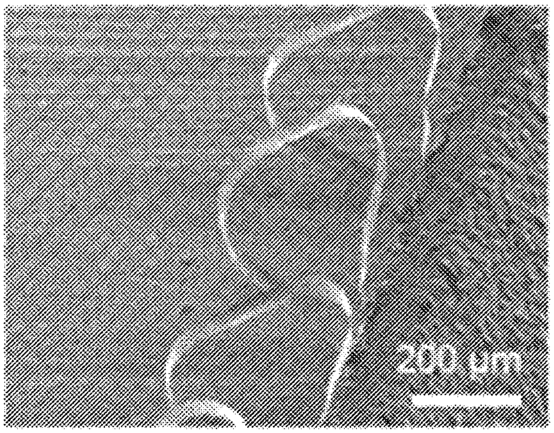
FIG. 14B provides an example SEM image of example three-dimensional mesostructures in accordance with some embodiments of the present disclosure.
Figure 14C:
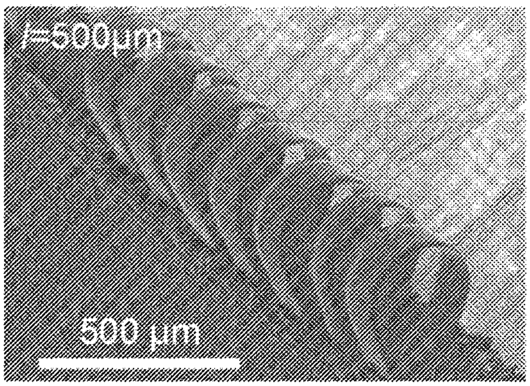
FIG. 14C provides an example SEM image of example three-dimensional mesostructures in accordance with some embodiments of the present disclosure.
Figure 14D:
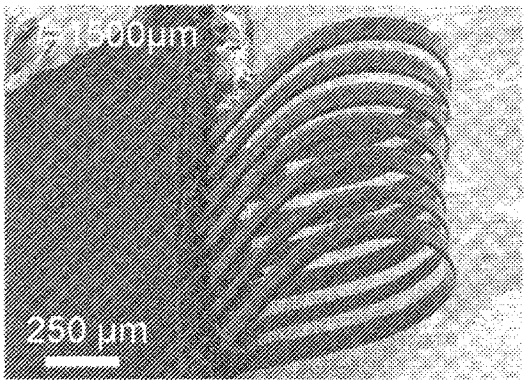
FIG. 14D provides an example SEM image of example three-dimensional mesostructures in accordance with some embodiments of the present disclosure.

FIG. 12A, FIG. 12B, FIG. 12C, and FIG. 12D illustrate various example three-dimensional mesostructures where the length l of the precursor is 200 μm. In some embodiments, increasing the length parameter l from 200 μm to 1500 μm while fixing d to 0 μm can effectively increase the radius of curvature of the three-dimensional hoops approximately from 30 μm to 240 μm, as shown in FIG. 5 and FIG. 10 to FIG. 14B. FIG. 14C to FIG. 14D illustrate various example three-dimensional mesostructures where the length l of the precursor is 500 μm and 1500 μm, respectively.

Figure 15:
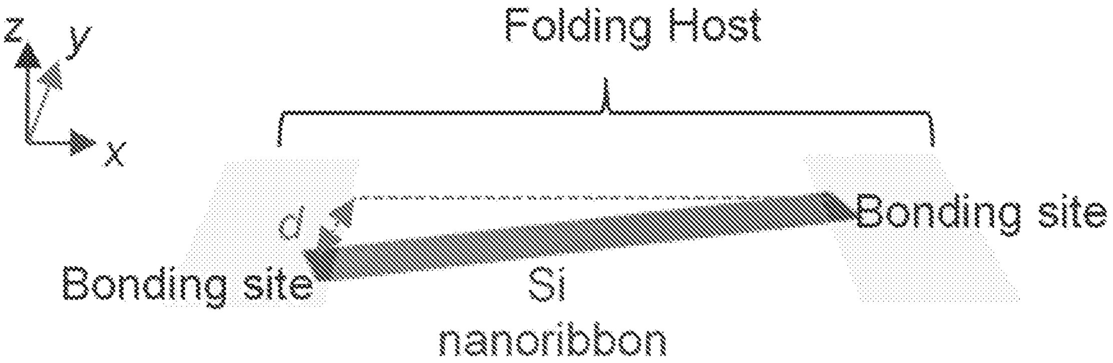
FIG. 15 provides an example schematic illustration indicating an example definition of a fabrication parameter d for fabricating an example three-dimensional mesostructure in accordance with some embodiments of the present disclosure.

FIG. 15 illustrates the dimensional parameter d that determines the degree of twisting of the three-dimensional silicon hoops.

Figure 16:
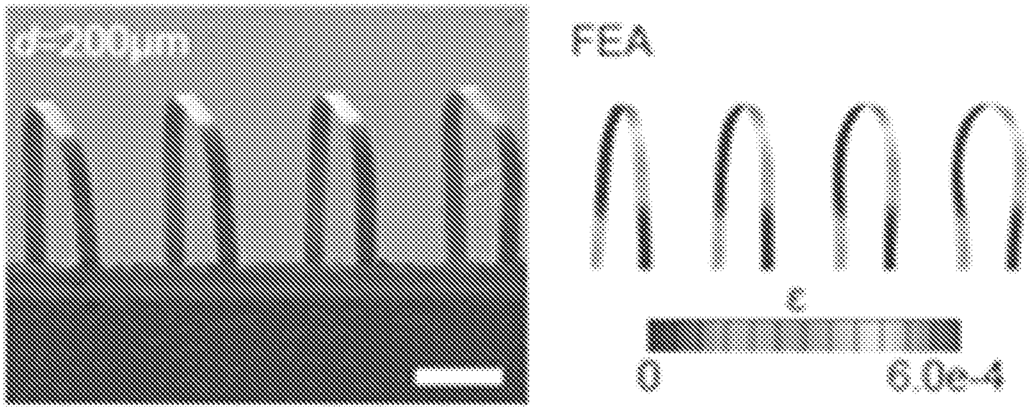
FIG. 16 provides an example SEM image and corresponding example FEA results of example three-dimensional mesostructures in accordance with some embodiments of the present disclosure.
Figure 17A:
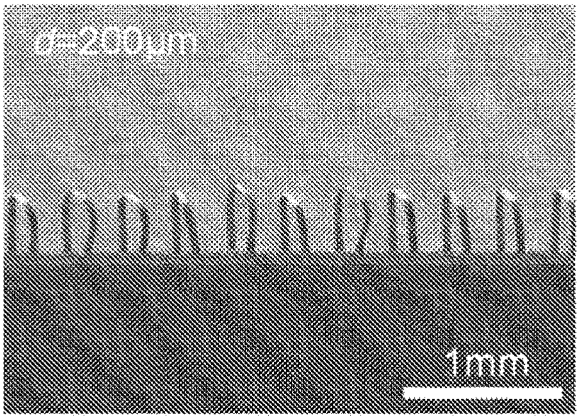
FIG. 17A provides an example SEM image of example three-dimensional mesostructures in accordance with some embodiments of the present disclosure.
Figure 17B:
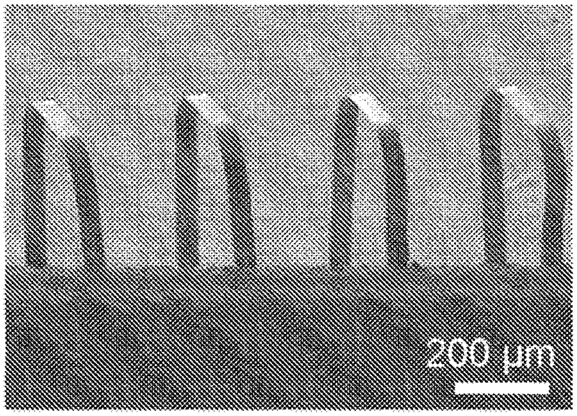
FIG. 17B provides an example SEM image of example three-dimensional mesostructures in accordance with some embodiments of the present disclosure.
Figure 18:
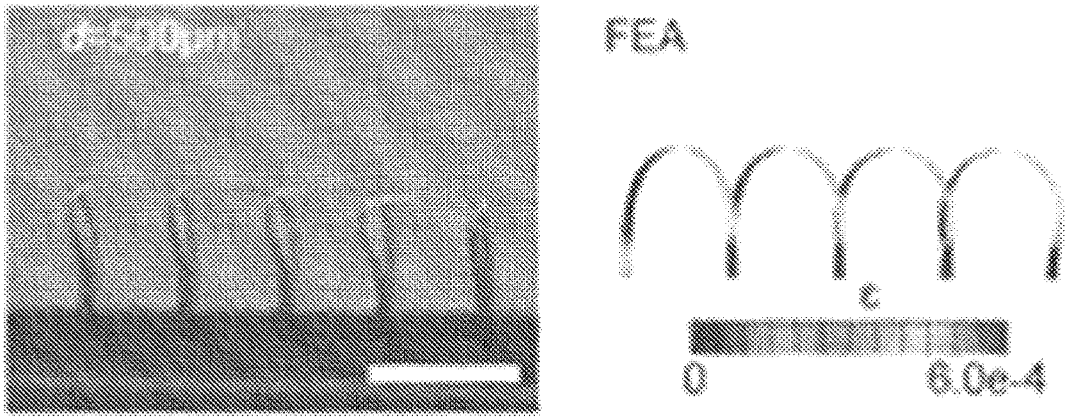
FIG. 18 provides an example SEM image and corresponding example FEA results of example three-dimensional mesostructures in accordance with some embodiments of the present disclosure.
Figure 19A:
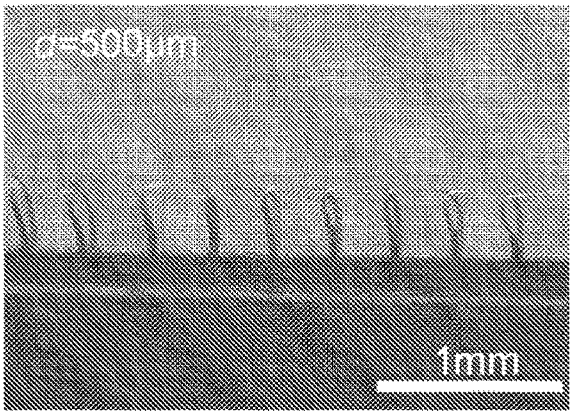
FIG. 19A provides an example SEM image of example three-dimensional mesostructures in accordance with some embodiments of the present disclosure, FIG. 19B provides an example SEM image of example three-dimensional mesostructures in accordance with some embodiments of the present disclosure.
Figure 19B:
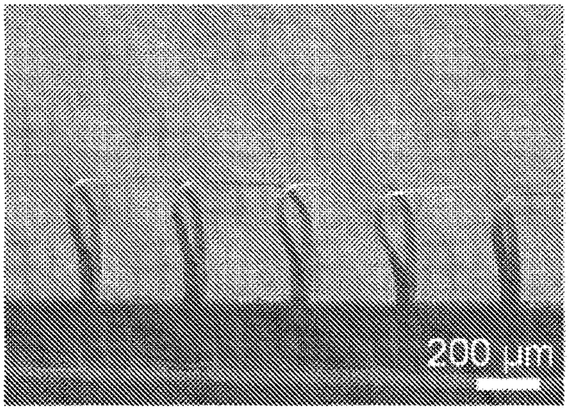
Figure 20:
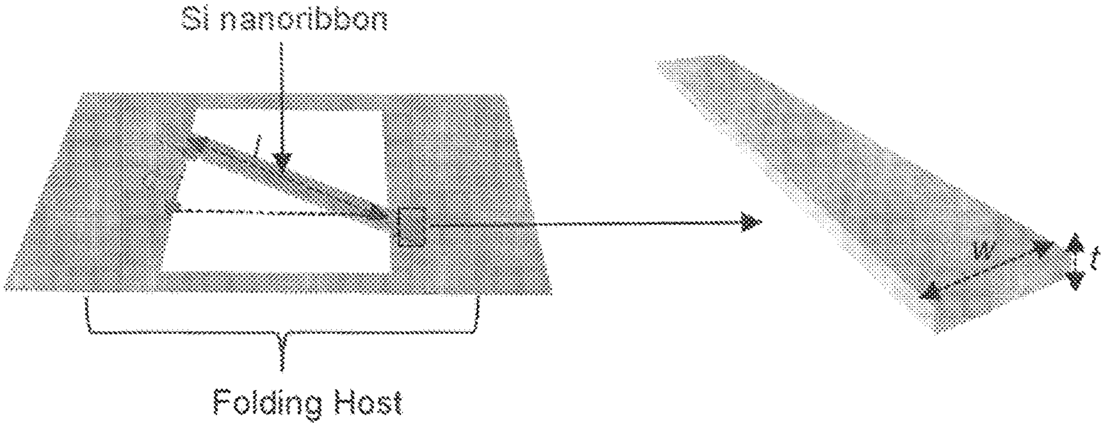
FIG. 20 provides an example schematic illustration indicating example definitions of fabrication parameters w, t, l, and d for fabricating an example three-dimensional mesostructure in accordance with some embodiments of the present disclosure.

In some embodiments, the dimensional parameter d dictates the orientation of the resultant three-dimensional Si hoops. For example, FIG. 16 illustrates an example where the dimensional parameter d is 200 μm. FIG. 18 illustrates an example where the dimensional parameter dis 500 μm. Additional representative examples include, but not limited to, inverted pyramids (such as the examples shown in FIG. 16, FIG. 17A, and FIG. 17B) and side-by-side archways (such as the examples shown in FIG. 18, FIG. 19A, and FIG. 19B) with corresponding parameter d values of 200 μm and 500 μm, respectively Example Optimizations of Fabrication Parameters As illustrated in the example above, the FEA simulation captures the magnitudes and distributions of the maximum principal strain (Emax) in the silicon mesostructures. In some embodiments, these observations suggest that for fully folded states (θ=90°), the Emax levels are largely determined by the dimensional parameters (l, w, t, and d) of the two-dimensional precursors relative to the folding host. As such, to guide design optimization for practical applications and ensure that the $\varepsilon_{max}$ of three-dimensional structure obtained by micro-folding registration strategy of ribbons is below the material failure threshold, a scaling law is developed (additional details are described herein) to estimate the $\varepsilon_{max}$ in the resultant three-dimensional mesostructures (fully folded) for different fabrication parameters (l, w, f) of the silicon ribbon, and the aforementioned dimensional parameter d (for example, as shown in FIG. 20).

Figure 21:
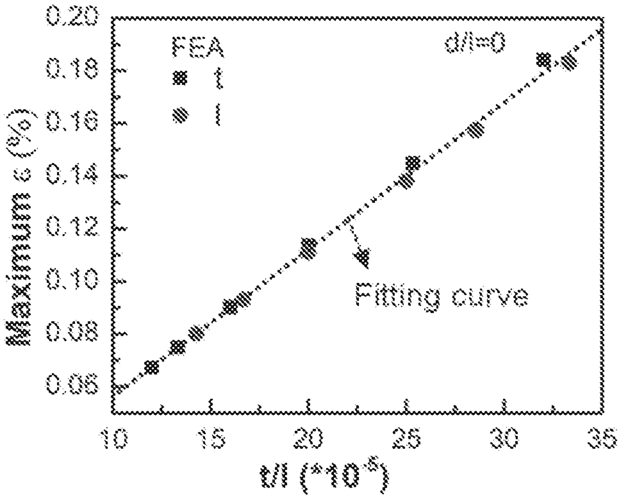
FIG. 21 provides an example diagram illustrating an example linear relationship between the maximum principal strain Emax and dimensionless parameter t/l through FEA simulation when d/l=0 in accordance with some embodiments of the present disclosure.
Figure 22:
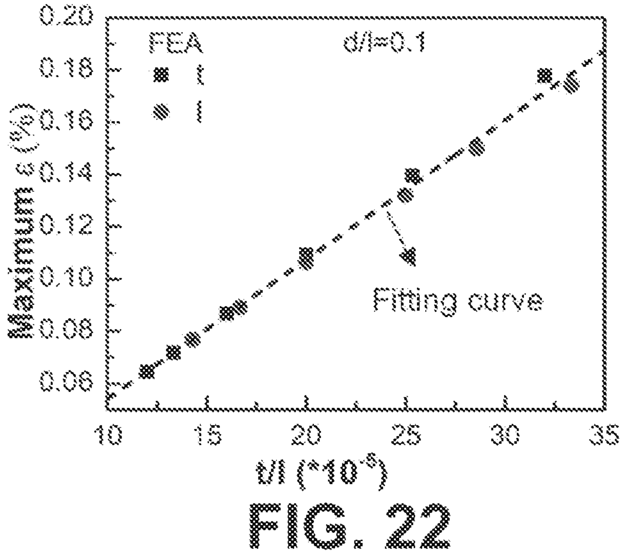
FIG. 22 provides an example diagram illustrating an example linear relationship between the maximum principal strain Emax and dimensionless parameter t/l through FEA simulation when d/l=0.1 in accordance with some embodiments of the present disclosure, FIG. 23 provides an example diagram illustrating an example linear relationship between the maximum principal strain Emax and dimensionless parameter t/l through FEA simulation when d/l=0.2 in accordance with some embodiments of the present disclosure.
Figure 23:
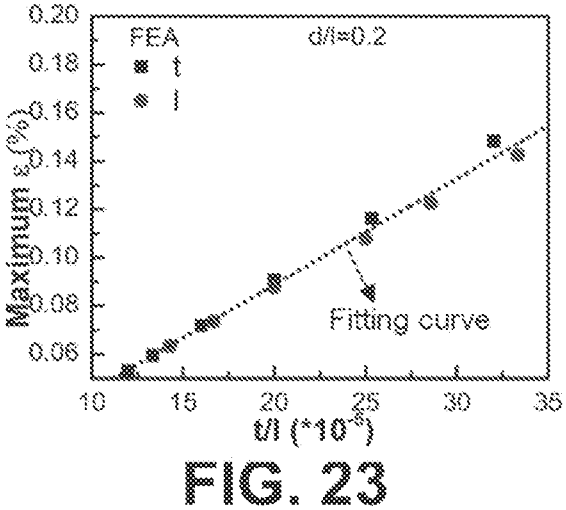

In some embodiments, the $\varepsilon_{max}$ in the filamentary silicon ribbon is proportional to t/l as shown in FIG. 21, FIG. 22, and FIG. 23.

Figure 24:
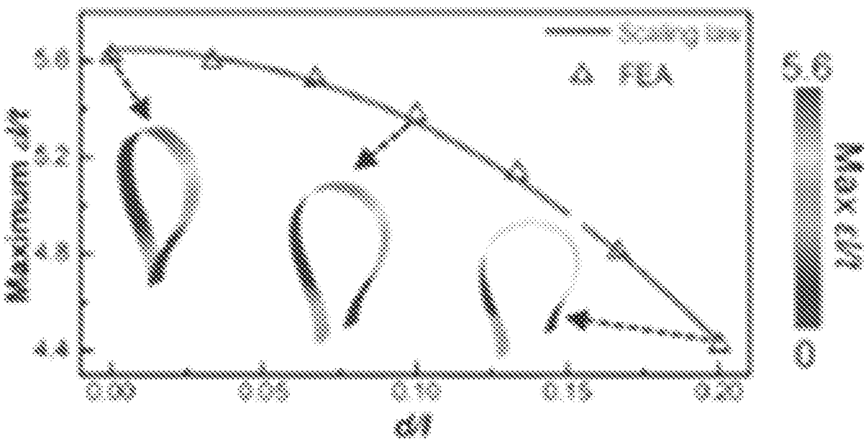
FIG. 24 illustrates example scaling law and example FEA results of the dimensionless parameter alt versus d/l for w/l=0.05 for an example three-dimensional mesostructure in the form of a three-dimensional silicon hoop in accordance with some embodiments of the present disclosure.
Figure 25:
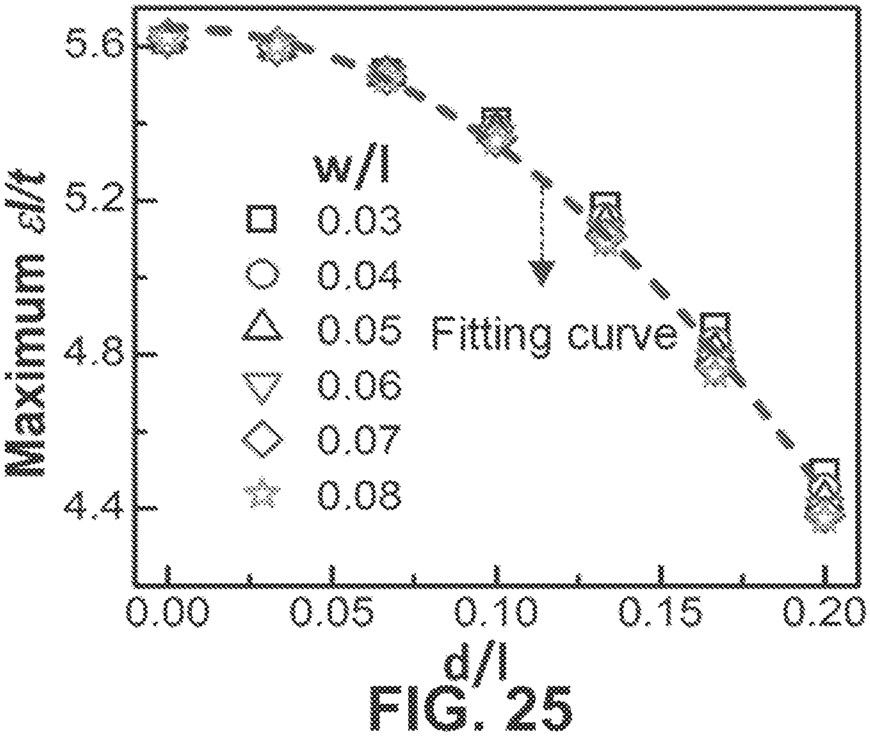
FIG. 25 illustrates an example diagram showing example fitting for dimensionless parameter εl/t and d/l with different w/l values ranging from 0.03 to 0.08 in accordance with some embodiments of the present disclosure.

For example, when the d/l and the w/l range from 0 to 0.2 and 0 to 0.1, respectively, the influence of w/l on $\varepsilon_{max}$ is negligible, and the $\varepsilon_{max}$ decreases monotonically with the decrease of d/l due to the increasing curvature radius of the ribbon (as shown in the examples from FIG. 24 and FIG. 25). This scaling law shows good agreement with experimental observations and provides an inverse-design guideline in the structural design to ensure the resultant $\varepsilon_{max}$ is below the material failure thresholds (for example, the silicon fracture thresholds) and avoid potential structural failure. In addition, because the scaling law is independent from the mechanical properties of material, it applies to any material that meets the above dimensional ranges.

For example, FIG. 24 illustrates the scaling law and FEA results of the dimensionless parameter εl/r versus d/l for w/l=0.05 for three-dimensional silicon hoops. Here, the w and l denote width and thickness of the individual ribbon, respectively.

Figure 26:
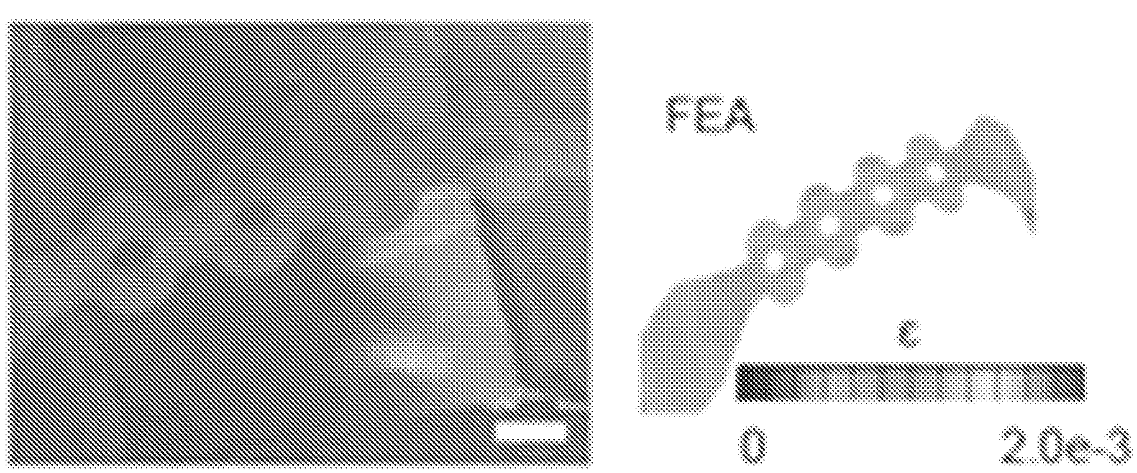
FIG. 26 provides an example SEM image and corresponding example FEA results of example three-dimensional mesostructures in accordance with some embodiments of the present disclosure.
Figure 27:
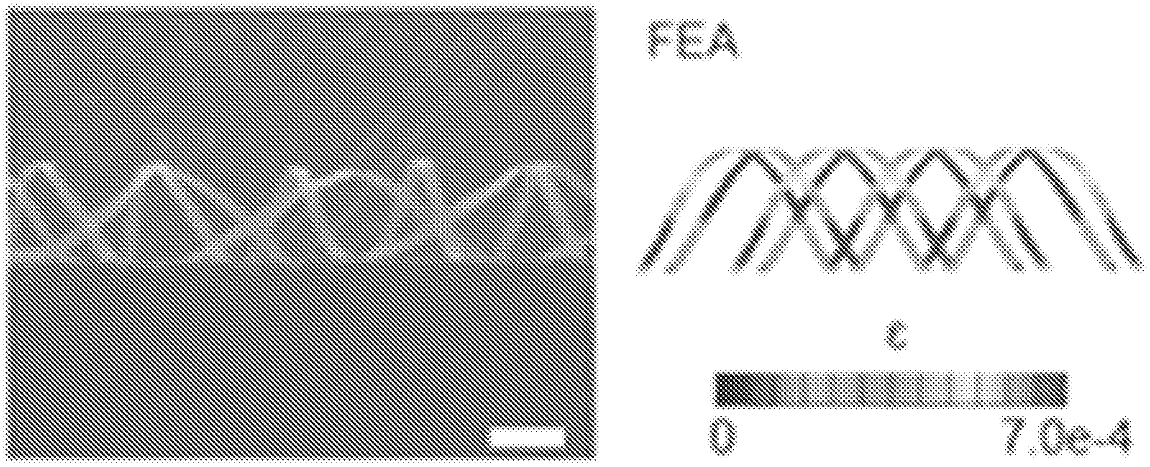
FIG. 27 provides an example SEM image and corresponding example FEA results of example three-dimensional mesostructures in accordance with some embodiments of the present disclosure.

FIG. 26 presents an example with an SEM image and corresponding FEA simulation that highlight the versatility of the deterministic microfolding in constructing three-dimensional silicon mesostructures. In the example shown in FIG. 26, the designed two-dimensional precursor composed of a line of silicon rings undergoes an out-of-plane folding process and then yields a three-dimensional mesostructure resembling a porous bracelet. Furthermore, this micro-folding strategy is compatible to build three-dimensional mesostructures with multilayer two-dimensional precursors via layer-by-layer transfer printing. FIG. 27 displays an example of a three-dimensional silicon double-helix structure.

FIG. 26 illustrates colorized SEM image and corresponding FEA result of a three-dimensional porous bracelet from a ribbon of monocrystalline Si, with folding angle θ being approximately 22.5 degrees.

Figure 28:
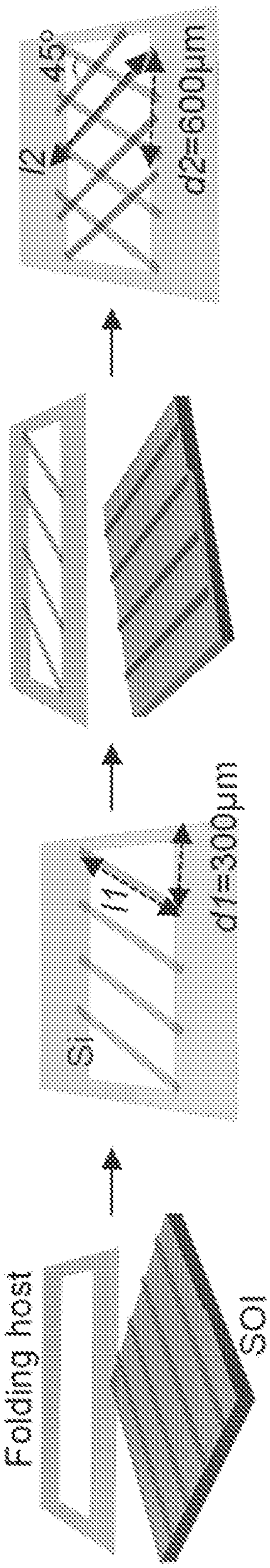
FIG. 28 provides an example schematic illustration highlighting an example process of fabricating an example three-dimensional mesostructure in accordance with some embodiments of the present disclosure.
Figure 29:
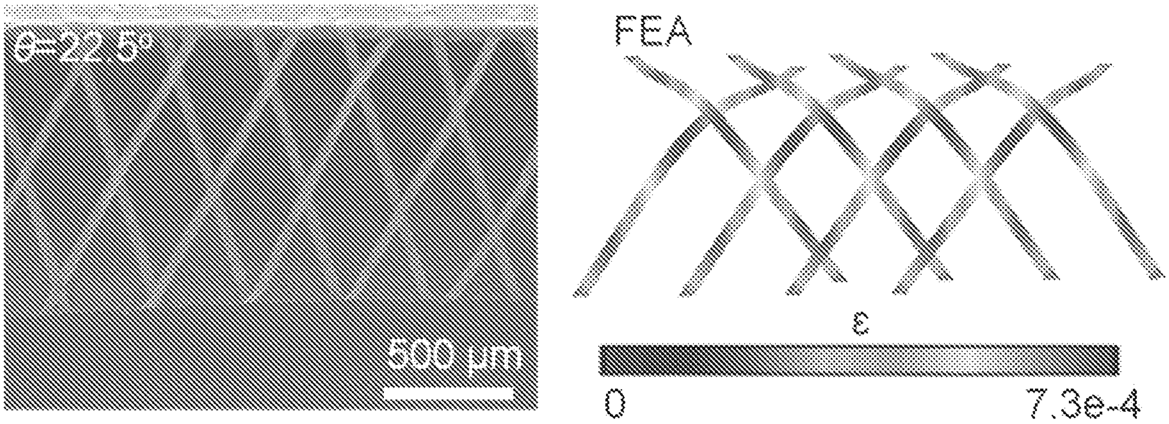
FIG. 29 provides an example SEM image and corresponding example FEA results of example three-dimensional mesostructures in accordance with some embodiments of the present disclosure.
Figure 30:
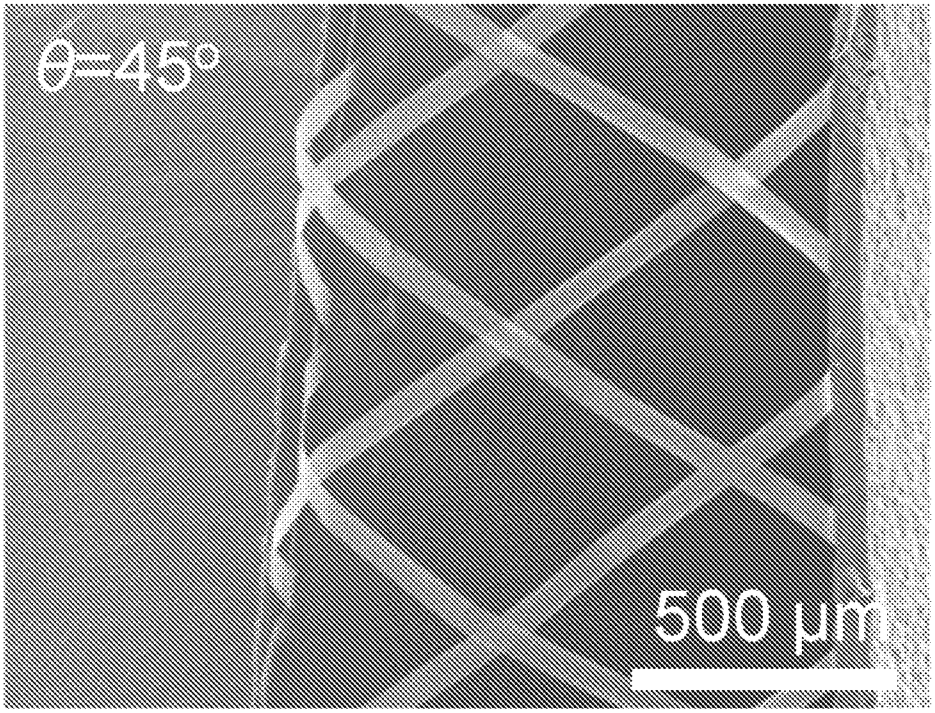
FIG. 30 provides an example SEM image of an example three-dimensional mesostructure in accordance with some embodiments of the present disclosure.
Figure 31:
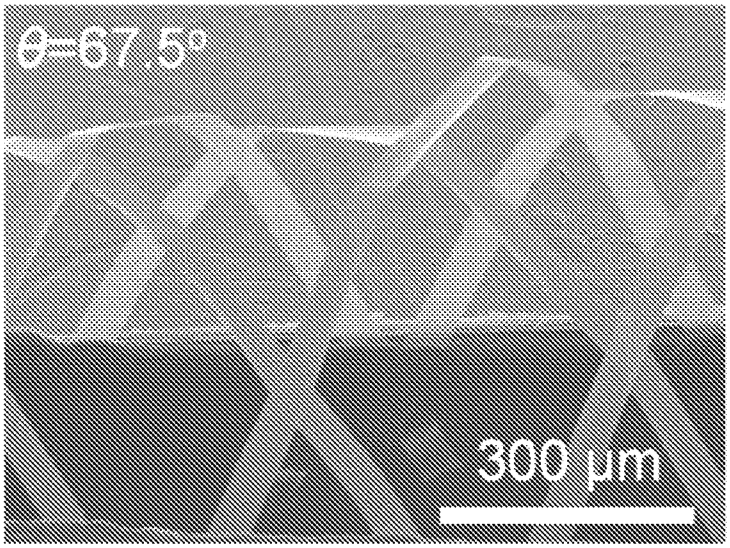
FIG. 31 provides an example SEM image of an example three-dimensional mesostructure in accordance with some embodiments of the present disclosure.
Figure 32:
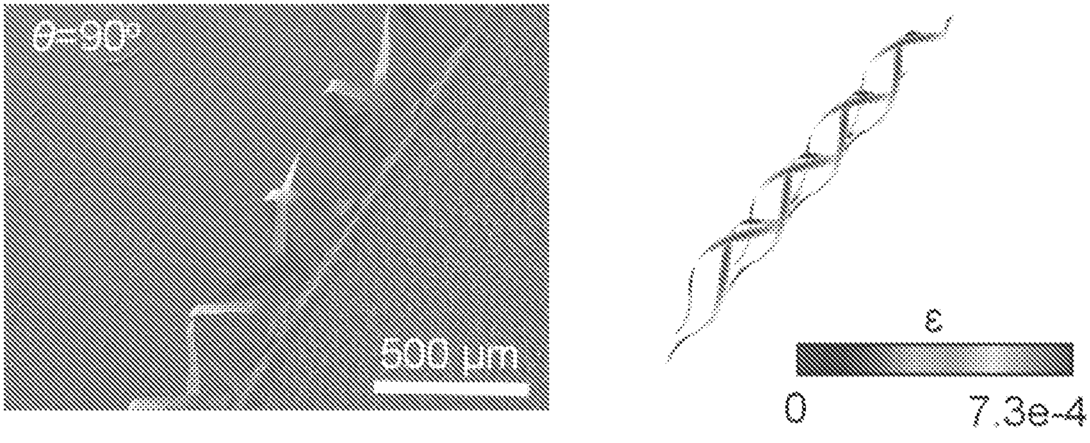
FIG. 32 provides an example SEM image and corresponding example FEA results of example three-dimensional mesostructures in accordance with some embodiments of the present disclosure.

FIG. 27 illustrates colorized SEM image and corresponding FEA result of a three-dimensional double helix from folding two layers of two-dimensional filamentary serpentine ribbons of silicon. The schematic illustrations in FIG. 28 show the corresponding fabrication process. By careful design of dimensional parameters (e.g., land d) for each layer, bilayer two-dimensional precursors consisting of intersected silicon ribbons pop up coherently without over deformation at the junction regions to form a double helix.

In some embodiments, the transitional states at various folding angles (for example, at 22.5°, 50°, 67.5°, and 90°, respectively) captured by both SEM images and the FEA simulations (for example, as shown in FIG. 29, FIG. 30, FIG. 31, and FIG. 32, respectively) indicate that the maximum principal strains ($\varepsilon_{max}$) remain well below the material failure threshold (for example, the fracture threshold, which is approximately 2%) for the constituent silicon.

In some embodiments, prior to bonding the precursor to the first bonding site portion and the second bonding site portion, an example method comprises determining a ratio between the precursor length l, the precursor thickness t, and/or the precursor thickness w associated with the precursor based at least in part on the material failure threshold associated with the precursor material. In particular, the example method may derive the scaling law of $\varepsilon_{max}$ based on the precursor length l, the precursor thickness t, and/or the precursor thickness w, and compare the scaling law of $\varepsilon_{max}$ with the material failure threshold.

Various embodiments of the present disclosure provide examples of deriving the scaling law of $\varepsilon_{max}$ in folding a slender ribbon.

Figure 35A:
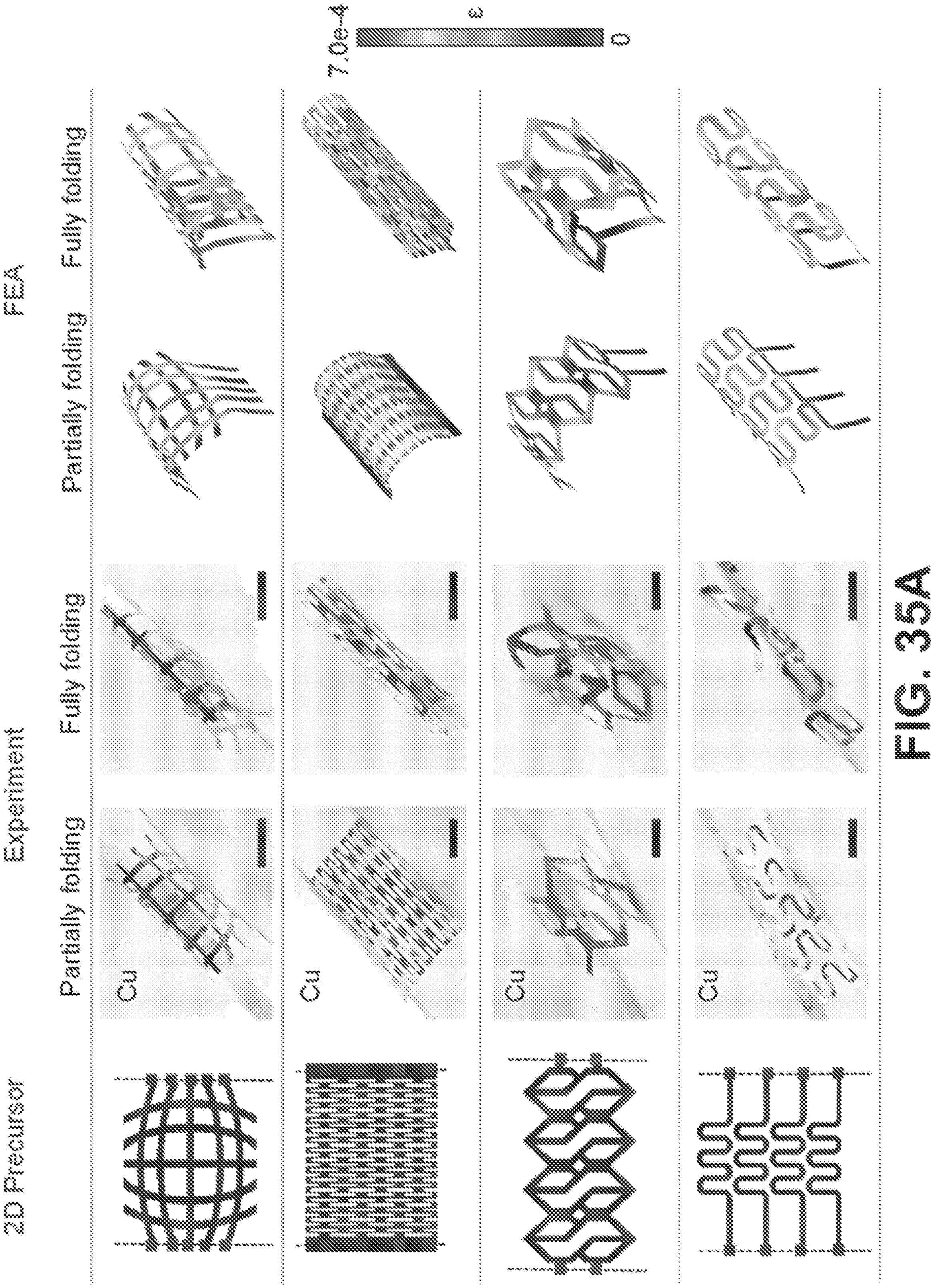
FIG. 35A provides illustrations of example two-dimensional precursors, example experimental images, and example FEA predictions of various example three-dimensional mesostructures via configuring folding registrations in accordance with some embodiments of the present disclosure, FIG. 35B provides illustrations of example two-dimensional precursors, example experimental images, and example FEA predictions of various example three-dimensional mesostructures via configuring folding registrations in accordance with some embodiments of the present disclosure, FIG. 36 provides illustrations of example two-dimensional precursors, example experimental images, and example FEA predictions of various example three-dimensional mesostructures via configuring folding registrations in accordance with some embodiments of the present disclosure.
Figure 35B:
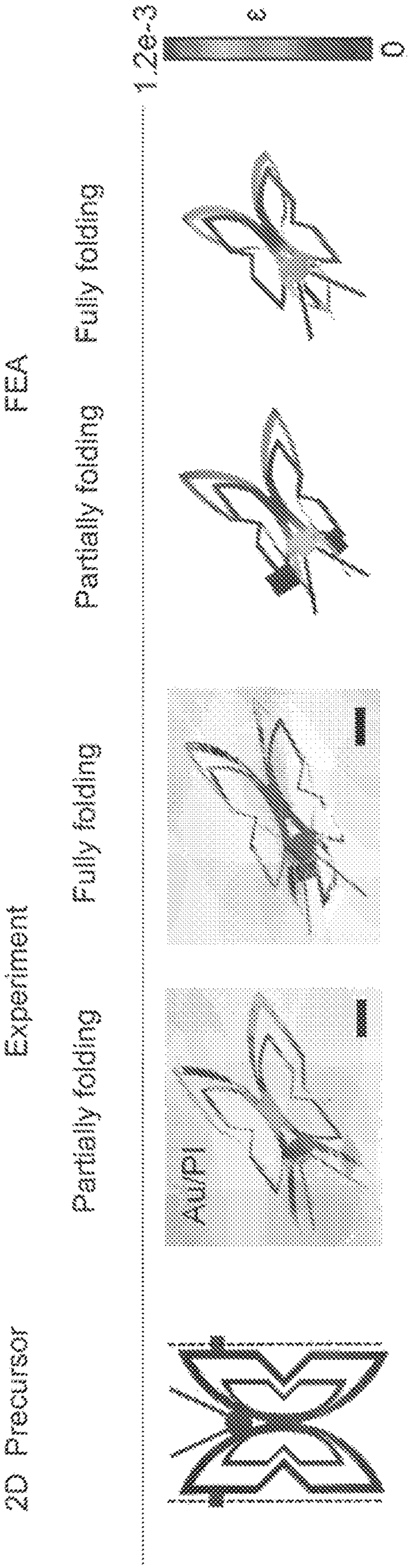

In some embodiments, the derivation of the scaling law can be based on the FEA of the microfolding process of a single slender ribbon, which can serve as a guiding principle for designing complex ribbon-based patterns (such as, but not limited to, the examples shown in FIG. 27, FIG. 35A, and FIG. 35B). In some embodiments, the scaling law focuses on four geometric parameters of a ribbon and its relationship with a folding host: length l, width w and thickness t of the ribbon, as well as the staggered distance d between two bonding sites (as illustrated in FIG. 1B). For a ribbon undergoing a bending process, the $\varepsilon_{max}$ is linearly proportional to κt, where the curvature κ is proportional to $l^{-1}$. In some embodiments, the FEA results verify that the influence of the non-dimensional ratio w/l on $\varepsilon_{max}$ can be ignored for w/l<0.1 (for example, as shown in FIG. 25). Then, the $\varepsilon_{max}$ can be expressed as $$\varepsilon_{max} = \frac{t}{l} \times \varphi\left(\frac{d}{l}\right) \quad \text{(Equation 1)}$$

In Equation 1 above, φ is a function of d/l. In some embodiments, the range of d/l from 0 to 0.2 can be considered in deriving the scaling law. In some embodiments, the straight lines in FIG. 21 to FIG. 23 clearly verify the above scaling law, and their slopes gave the value of the function φ under the corresponding variable d/l. In some embodiments, taking d/l as an independent variable and $\varepsilon_{max} \cdot l/t$ as function value (for example, as shown in FIG. 25), the function φ was determined by fitting the FEA results. Finally, the $\varepsilon_{max}$ was given by $$\varepsilon_{max} = \frac{t}{l} \times \left[-30.3\left(\frac{d}{l}\right)^2 + 5.65\right] \quad \text{(Equation 2)}$$

In some embodiments, the example method may adjust the length l, width w, thickness t of the ribbon, and/or the staggered distance d, so that the $\varepsilon_{max}$ does not exceed the material failure threshold.

Example Three-Dimensional Mesostructures

Various examples three-dimensional mesostructures in accordance with embodiments of the present disclosure illustrate significant outcomes that lead to multi-dimensional control of structural formation and unconventional architectures such as an inverted pyramid of monocrystalline silicon sitting on an edge, freestanding microscale cages of gold, and other examples of complex three-dimensional forms across various high-performance materials and length scales, that, collectively, present qualitative distinguishment beyond the scope of other strategies in achieving morphable three-dimensional mesostructures.

Fundamental studies of the strain distribution, structural stability, and folding behaviors exhibited in the microfolding process discussed here establish general rationales for designing three-dimensional morphable mesostructures with distinct, tunable topologies. Moreover, applications in morphable epicardial bioelectronics for cardiac mapping highlight the broad utility and scalability of transformable three-dimensional systems realized by the deterministic microfolding FIG. 33 to FIG. 40C illustrate various examples of constructed three-dimensional mesostructures. Through the example micro-folding scheme described above, diverse feature sizes and wide-ranging geometries can be achieved in a broad range of materials. For example, FIG. 33 to FIG. 40C present a collection of three-dimensional morphable mesostructures composed of various functional materials (including, but not limited to, metal, polymer, and inorganic semiconductor) with geometries ranging from simple to complex states at submillimeter-scale or millimeter-scale.

Figure 33:
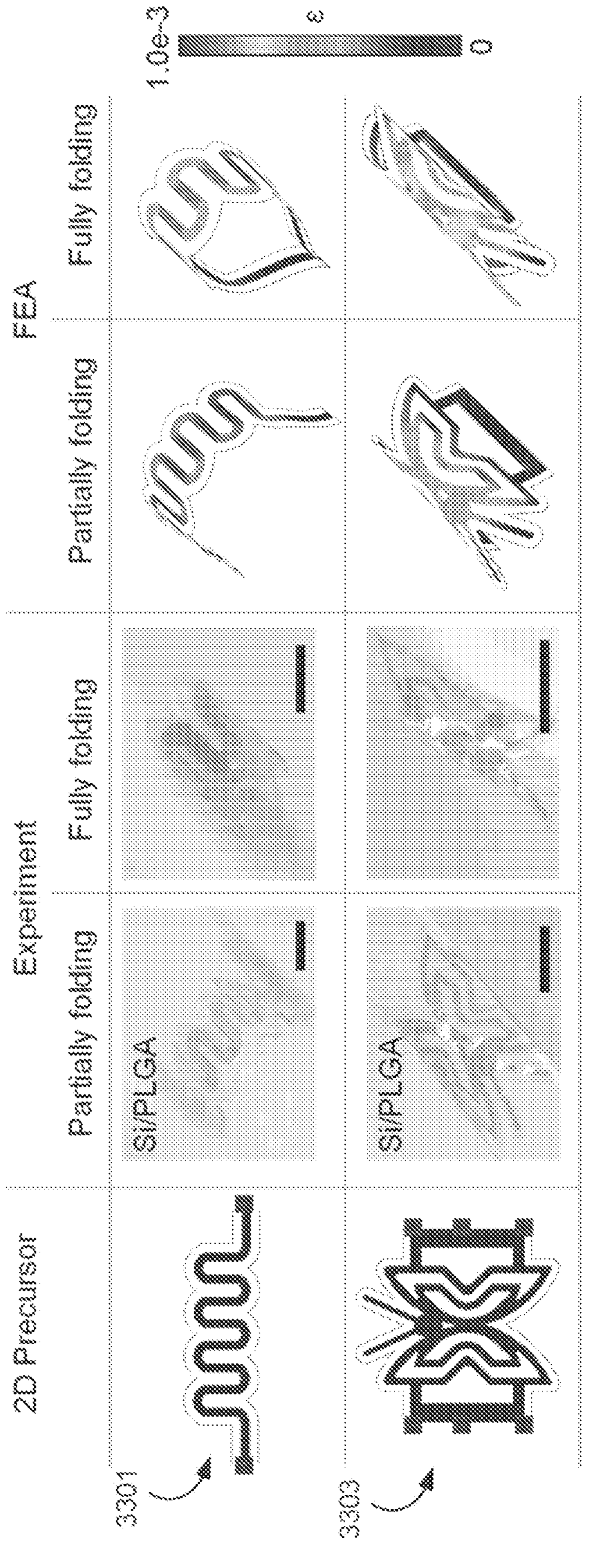
FIG. 33 provides illustrations of example two-dimensional precursors, example experimental images, and example FEA predictions of various example three-dimensional mesostructures via configuring folding registrations in accordance with some embodiments of the present disclosure.

FIG. 33 provides representative examples of three-dimensional mesostructures transformed from corresponding two-dimensional silicon/polymer bilayers (for example, based on the various example fabrication methods described above). In some embodiments, photolithography, etching, and laser cutting define the patterns of two-dimensional bilayers that comprises the silicon layer and the PLGA layer. In some examples, a layer width associated with the silicon layer is 200 nm. In some embodiments, a layer width associated with the PLGA layer is 2 μm. In some embodiments, example micro-folding processes in accordance with some embodiments of the present disclosure can deform the two-dimensional components into specific three-dimensional configurations resembling a hair hoop (as shown in the example portion 3301 of FIG. 33) or a butterfly (as shown in the example portion 3303 of FIG. 33).

For example, the three-dimensional hair hoop and butterfly structures shown in FIG. 33 are made of a bilayer of silicon (with a thickness of approximately 200 nm) and PLGA (with a thickness of approximately 2 μm). Such a combination of materials and their associated thicknesses can provide technical advantages and benefits such as, but not limited to, an optimized balance between rigidness and flexibility of the three-dimensional mesostructure. The scale bars of the example portion 3301 of FIG. 33 are 300 μm, and the scale bars of the example portion 3303 of FIG. 33 are 1.5 mm.

Figure 34:
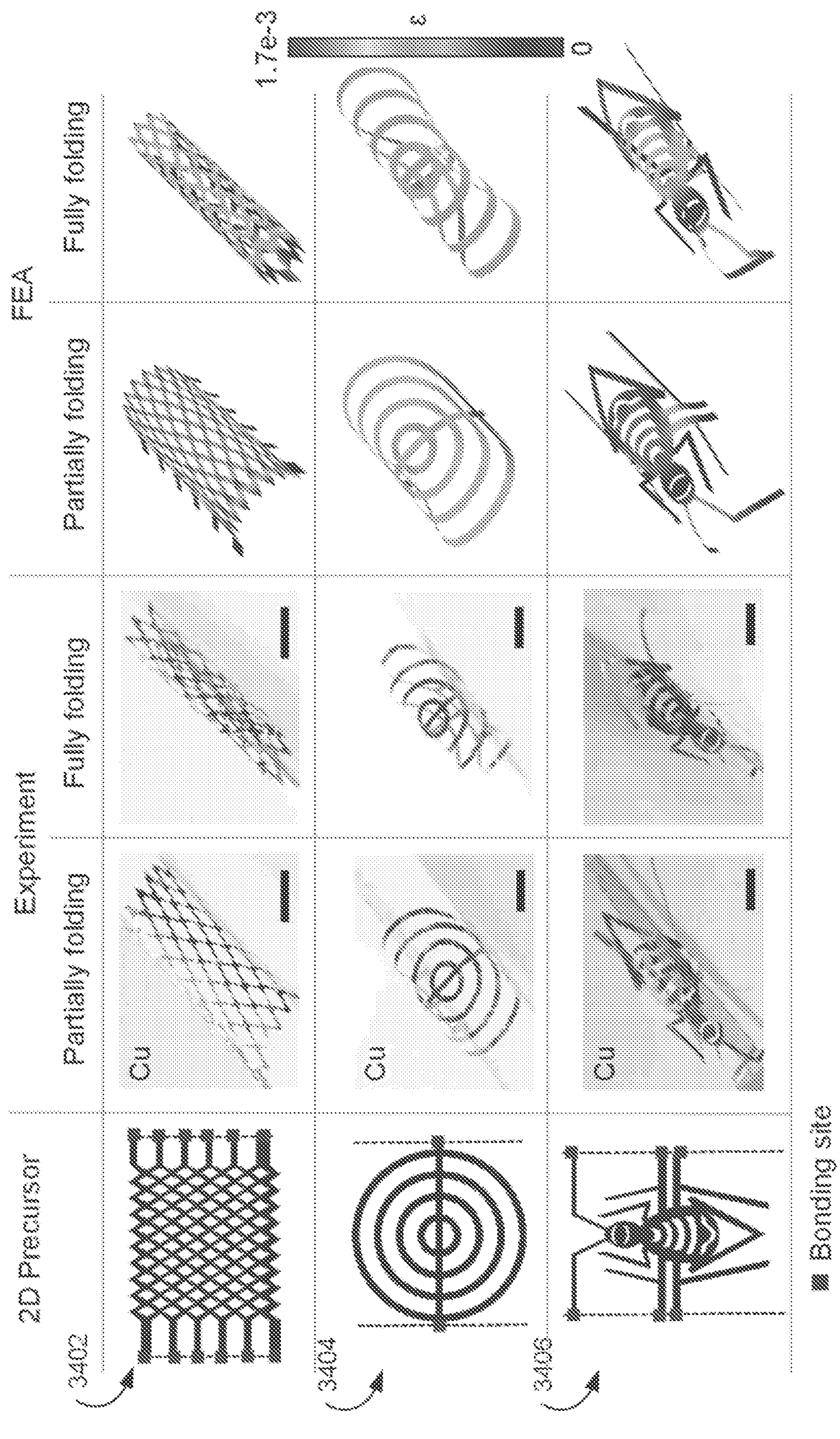
FIG. 34 provides illustrations of example two-dimensional precursors, example experimental images, and example FEA predictions of various example three-dimensional mesostructures via configuring folding registrations in accordance with some embodiments of the present disclosure.

FIG. 34 presents kirigami-inspired examples using a single layer of gold (Cu). In some embodiments, the thickness associated with the layer of Cu is approximately 1 μm. Such a combination of material and its associated thickness can provide technical advantages and benefits such as, but not limited to, an optimized balance between rigidness and flexibility of the three-dimensional mesostructure. The example portion 3402 of FIG. 34 shows a three-dimensional mesh tube that is transformed from a wire fence-patterned two-dimensional precursor. The example portion 3404 of FIG. 34 shows a three-dimensional saddle formed from a two-dimensional precursor of concentric circles. The three-dimensional mesostructure in the example portion 3406 of FIG. 34 resembles a spider, constructed from a patterned two-dimensional precursor that uses controlled folding to realize the three-dimensional transformations. The scale bar of the example portion 3402 of FIG. 34 is 500 μm. The scale bar of the example portion 3404 of FIG. 34 is 1.0 mm. The scale bar of the example portion 3406 of FIG. 34 is 2.0 mm.

FIG. 35A and FIG. 35B show additional three-dimensional folded mesostructures that resemble a fishing net, a sliding door, a hollow-out lampshade, and an array of hair hoops, respectively. Here, the optical images and FEA simulations (as shown in FIG. 35A and FIG. 35B) reveal both the intermediate states of assembly (partial folding) and final configurations (full folding), indicating high reversibility in the structural transformation.

Figure 36:
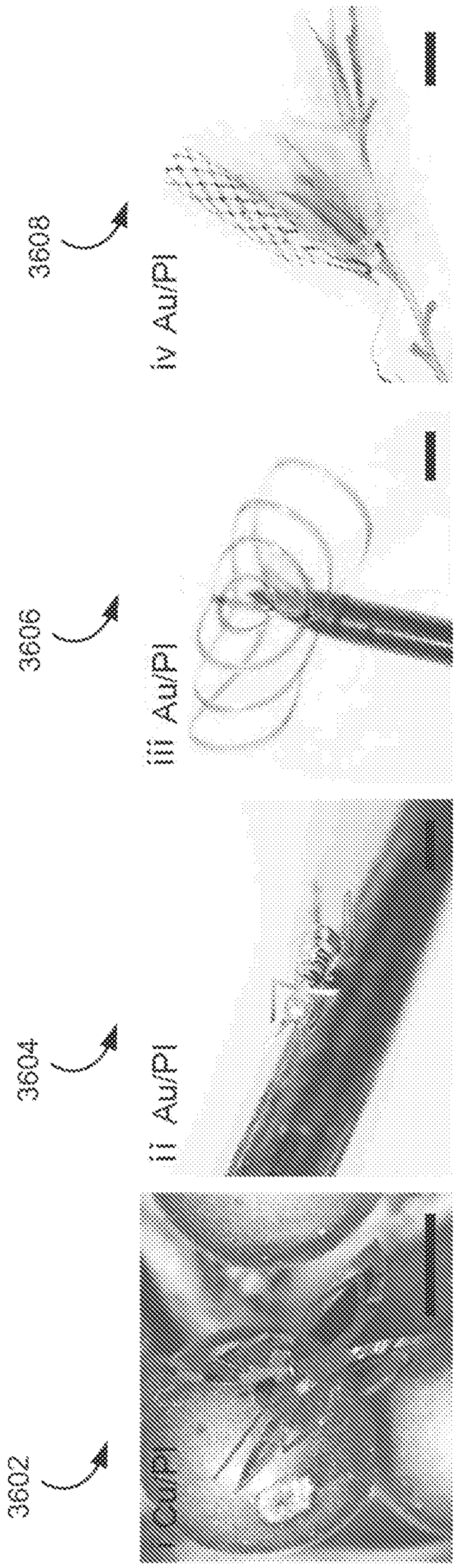

In all cases, the freestanding three-dimensional mesostructures can be naturally blended with various environments such as the plant seed, grass leaf, needle tip, twig, and even water (for example, as shown in FIG. 36), which paves the way for their broad applications.

In particular, FIG. 36 provides optical images of freestanding three-dimensional mesostructures that can stand on the seed, grass, needle tip and twig. In the example portion 3602 of FIG. 36, a butterfly structure is made of a bilayer of copper (having a thickness of approximately 150 nm) and polyimide (having a thickness of approximately 10 μm). Such a combination of materials and their associated thicknesses can provide technical advantages and benefits such as, but not limited to, an optimized balance between rigidness and flexibility of the three-dimensional mesostructure. In the example portion 3604 of FIG. 36, a spider structure is illustrated. In the example portion 3606 of FIG. 36, a saddle structure is illustrated. In the example portion 3608 shown in FIG. 36, a wire fence structure is illustrated.

The example portion 3604, the example portion 3606, and the example portion 3608 illustrate example three-dimensional mesostructures that are made of a bilayer of gold (having a thickness of approximately 150 nm) and polyimide (having a thickness of approximately 10 μm. Such a combination of materials and their associated thicknesses can provide technical advantages and benefits such as, but not limited to, an optimized balance between rigidness and flexibility of the three-dimensional mesostructure. The scale bar of the example portion 3602 is 1.5 mm. The scale bar of the example portion 3604 is 2.5 mm. The scale bar of the example portion 3606 is 1 mm. The scale bar of the example portion 3608 is 500 μm.

The aforementioned designs rely on a parallel folding registration, where the trench edges of the folding host are parallel to each other, to enable three-dimensional transformation. Here, configuring folding registration can further expand the design versatility.

Figure 37:
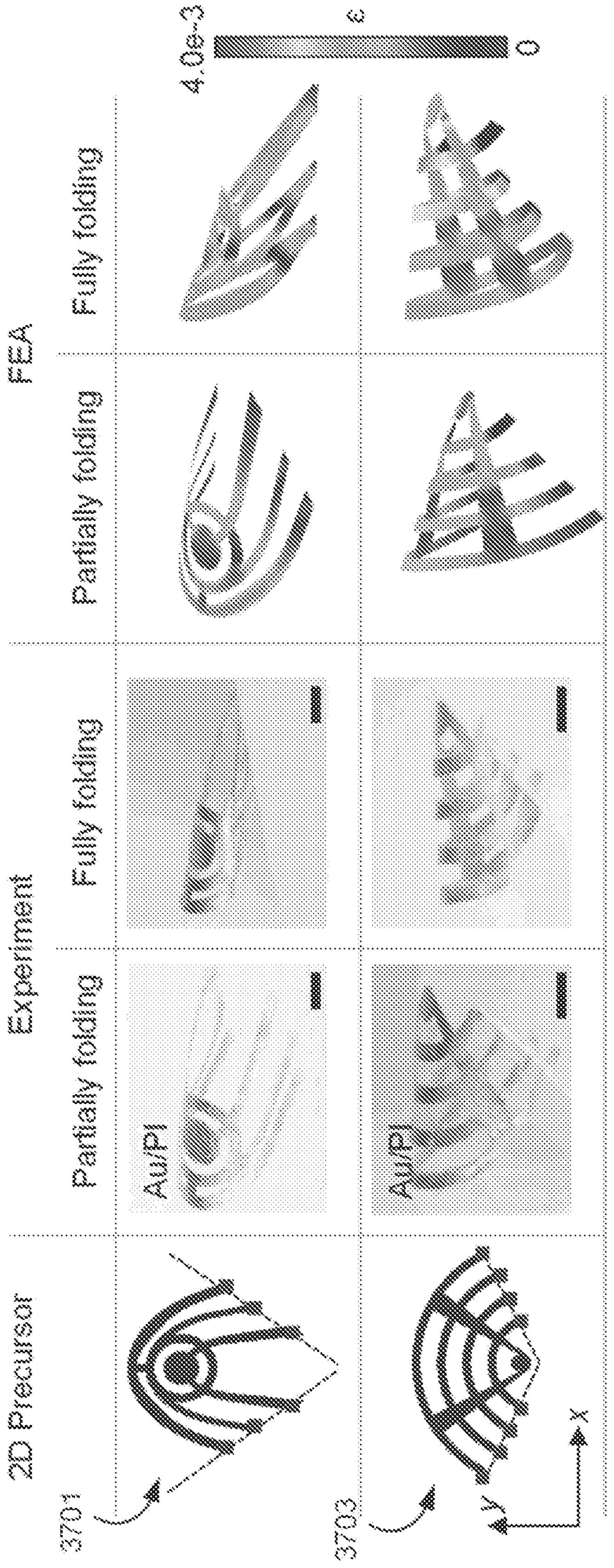
FIG. 37 provides illustrations of example two-dimensional precursors, example experimental images, and example FEA predictions of various example three-dimensional mesostructures via configuring folding registrations in accordance with some embodiments of the present disclosure.

FIG. 37 illustrates examples of three-dimensional cone-like structures relying on angled folding registration. As illustrated in the example portion 3701 of FIG. 37, a lithographically defined bilayer of gold (having a thickness of 150 nm) and polyimide (having a thickness of 10 μm) bonded onto a folding host, whose edges are arranged with a predefined angle 60°, forms a jellyfish-like three-dimensional structure. The optical images and FEA simulations capture the transitional and final states of the assembly process that resembles swimming movements of the jellyfish. Moreover, the compatible range of the angle between the trench edges of the folding host could span from acute to obtuse angles.

An example based on obtuse-angled folding registration appears in example portion 3703 of FIG. 37, highlighting the transformation from a two-dimensional bilayer of Au (having a thickness of 150 nm) and PI (having a thickness of 10 μm) to an ice-cream cone structure via arranging the pair of the trench edges at a predefined angle 120°. Such a combination of materials and their associated thicknesses can provide technical advantages and benefits such as, but not limited to, an optimized balance between rigidness and flexibility of the three-dimensional mesostructure.

In FIG. 37, the angled folding registration enables various cone-like structures made of a bilayer of gold (having a thickness of approximately 150 nm) and polyimide (having a thickness of approximately 10 μm) Such a combination of materials and their associated thicknesses can provide technical advantages and benefits such as, but not limited to, an optimized balance between rigidness and flexibility of the three-dimensional mesostructure.

Compared with the parallel folding registration, the angled folding registration highlighted in FIG. 37 relies on arranging the pair of trench edges of the host at a predefined angle, 60 degrees and 120 degrees, for the example portion 3701 and the example portion 3703, respectively.

Figure 38:
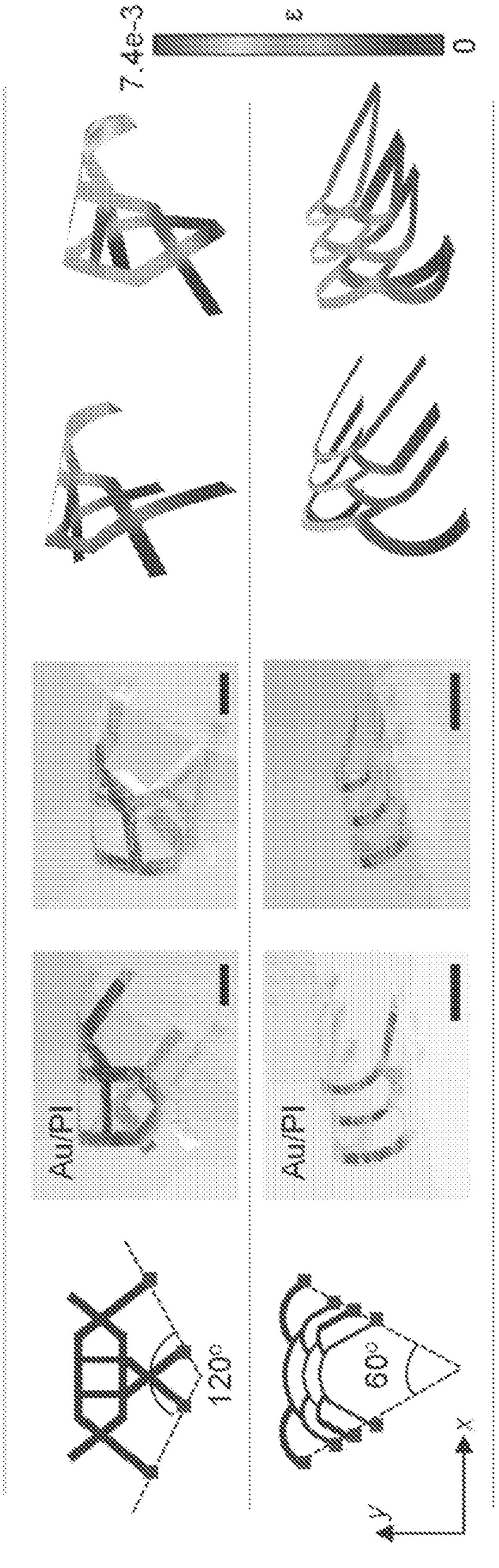
FIG. 38 provides illustrations of example two-dimensional precursors, example experimental images, and example FEA predictions of various example three-dimensional mesostructures via configuring folding registrations in accordance with some embodiments of the present disclosure.

In some embodiments, adopting the same folding registration, a flying eagle and a moving insect are demonstrated in FIG. 38, respectively.

Figure 39:
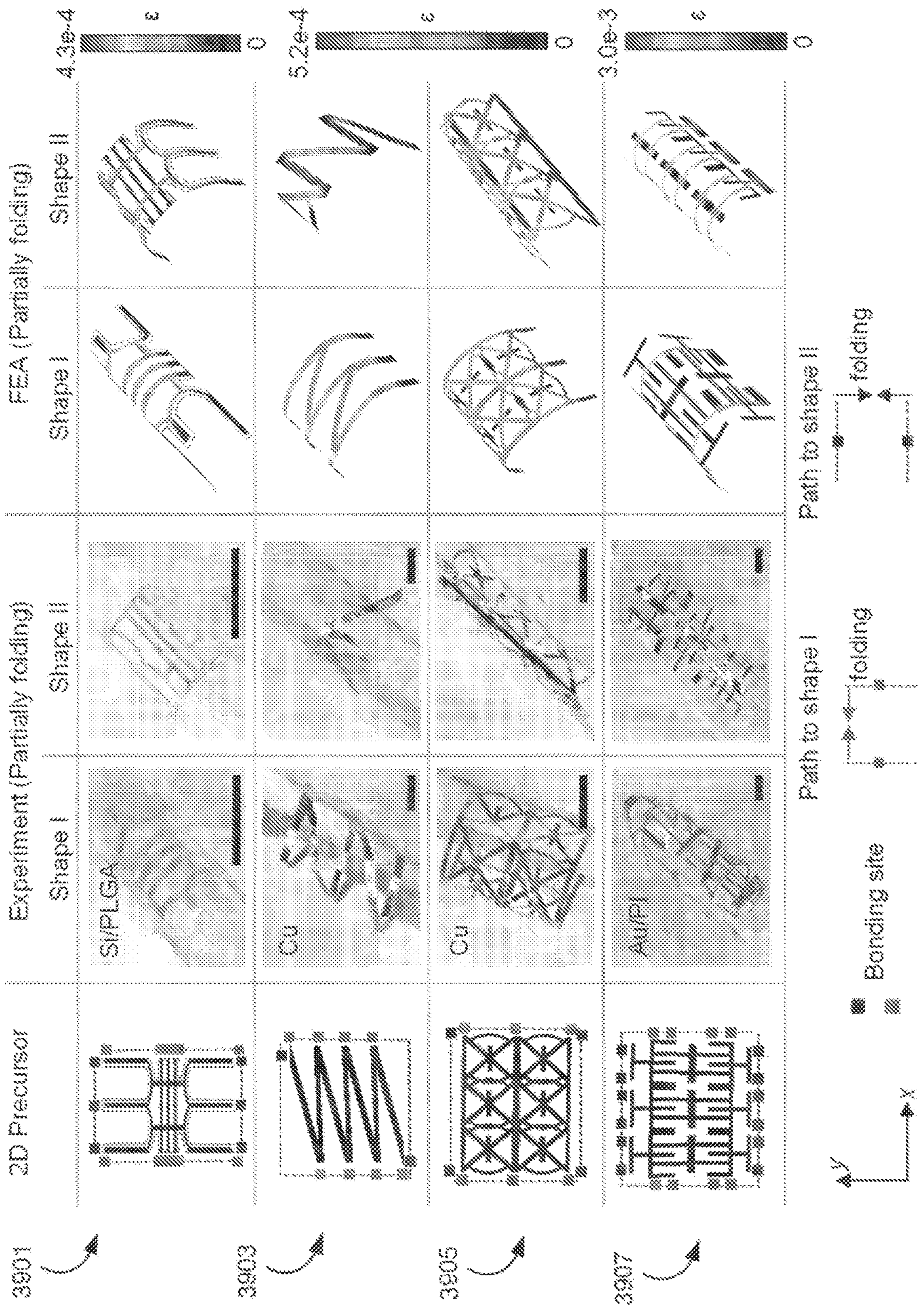
FIG. 39 provides illustrations of example two-dimensional precursors, example experimental images, and example FEA predictions of various example three-dimensional mesostructures via configuring folding registrations in accordance with some embodiments of the present disclosure.

Furthermore, this origami scheme enables three-dimensional reconfigurability by switching folding registrations between various folding axes, to generate dramatically distinct three-dimensional mesostructures from the same two-dimensional precursors. FIG. 39 and FIG. 40C present a class of two-dimensional precursors of various materials and/or patterns that can be reshaped between two distinct three-dimensional configurations.

Specifically, the example portion 3901 of FIG. 39 shows a Si/PLGA bilayer with a ribbon-shaped geometry folds along x-axis (folding registration path I) and y-axis (folding registration path II) leading to a turtle shell (shape I) and shield (shape II), respectively, from same two-dimensional precursors. This design strategy also enables a different set of ribbon-shaped mesostructures constructed with either metal or bilayers of metal and polymer.

In particular, the example portion 3901 of FIG. 39 illustrates example mesostructures made of a bilayer of Si (having a thickness of approximately 200 nm) and PLGA (having a thickness of approximately 2 μm). Such a combination of materials and their associated thicknesses can provide technical advantages and benefits such as, but not limited to, an optimized balance between rigidness and flexibility of the three-dimensional mesostructure. The example portion 3903 and example portion 3905 of FIG. 39 illustrate example three-dimensional mesostructures that are made of Cu (having a thickness of approximately 1 μm). The example portion 3901 of FIG. 39 illustrates three-dimensional mesostructures that are made of bilayer of Au (having a thickness of approximately 150 nm) and PI (having a thickness of approximately 10 μm). In FIG. 39, the scale bars are approximately 1 mm.

The example portion 3903 of FIG. 39 shows that a zigzag Cu ribbon can form a singular shoelace with y-axis folding, whereas the x-axis folding transformation yields a decorated ring. Even in cases of two-dimensional Cu precursors with bilateral symmetry, as illustrated in the example portion 4002 of FIG. 40A, the resulting three-dimensional mesostructures resemble either diamonds in a series or a fence depending on folding registration path, I or II, respectively.

Figure 40A:
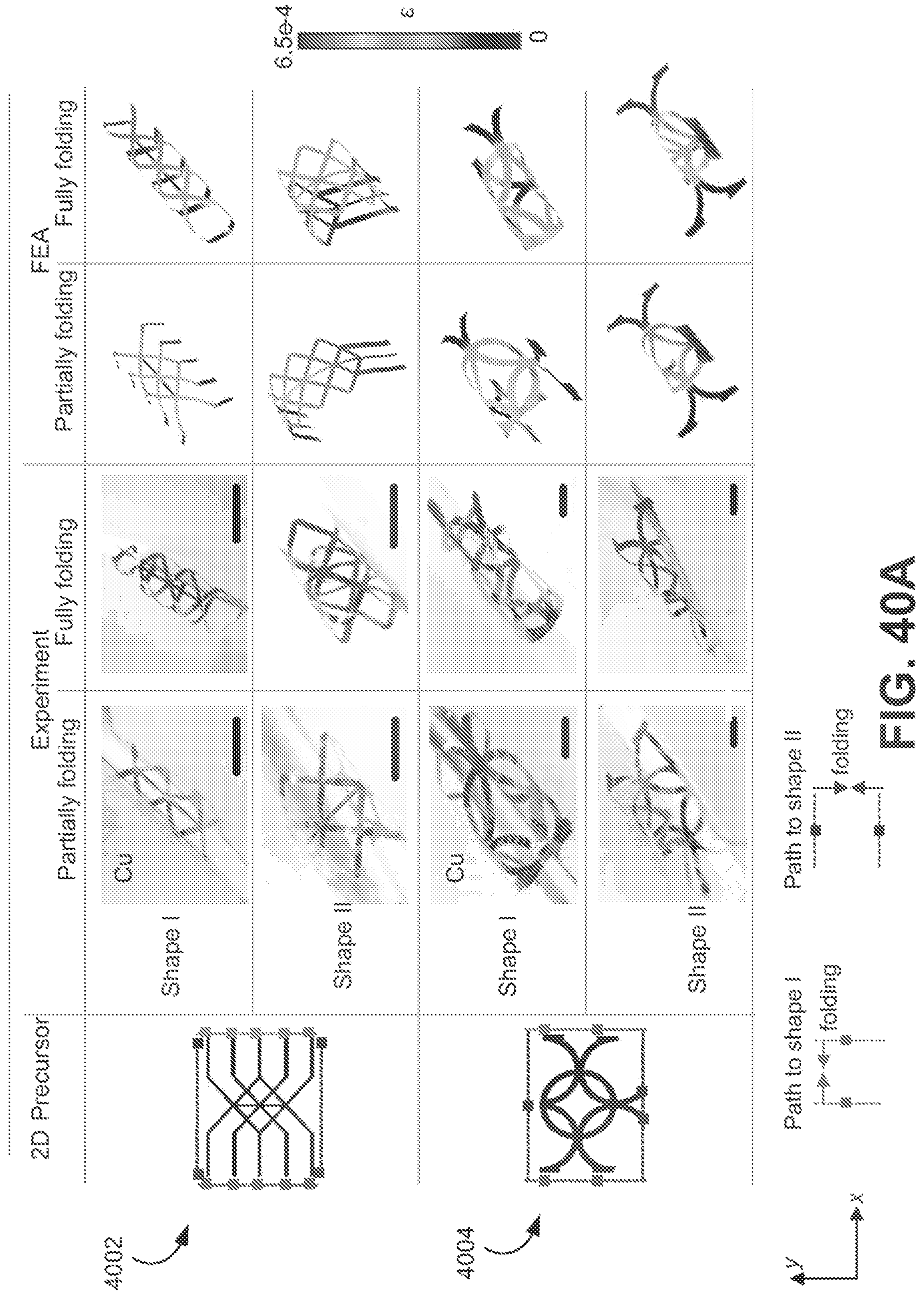
FIG. 40A, FIG. 40B, and FIG. 40C provide illustrations of example two-dimensional precursors, example experimental images, and example FEA predictions of various example three-dimensional mesostructures via configuring folding registrations in accordance with some embodiments of the present disclosure, FIG. 41 provides an example flow diagram illustrating an example method of fabricating an example three-dimensional epicardial bioelectronic probe in accordance with some embodiments of the present disclosure.
Figure 40B:
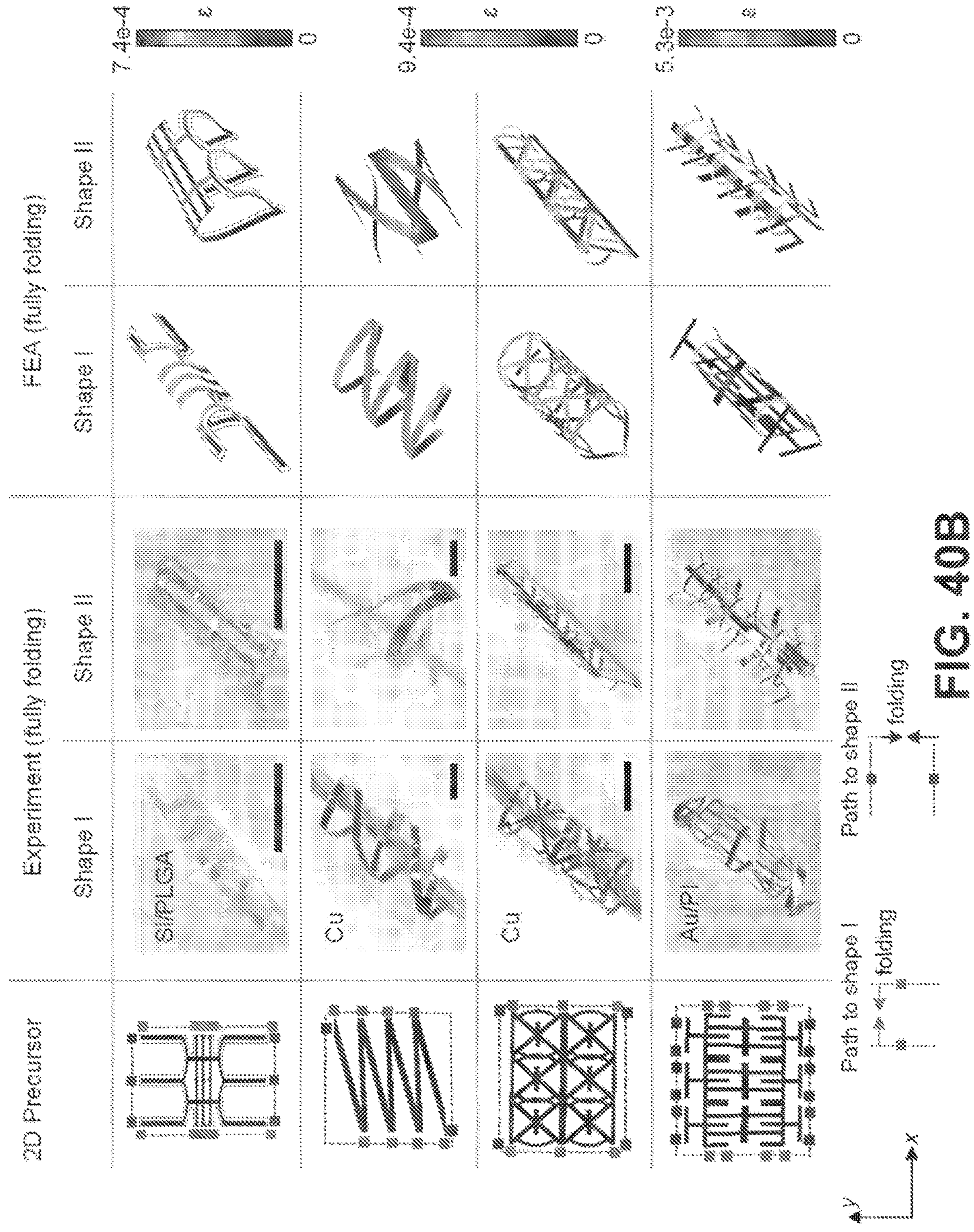
Figure 40C:
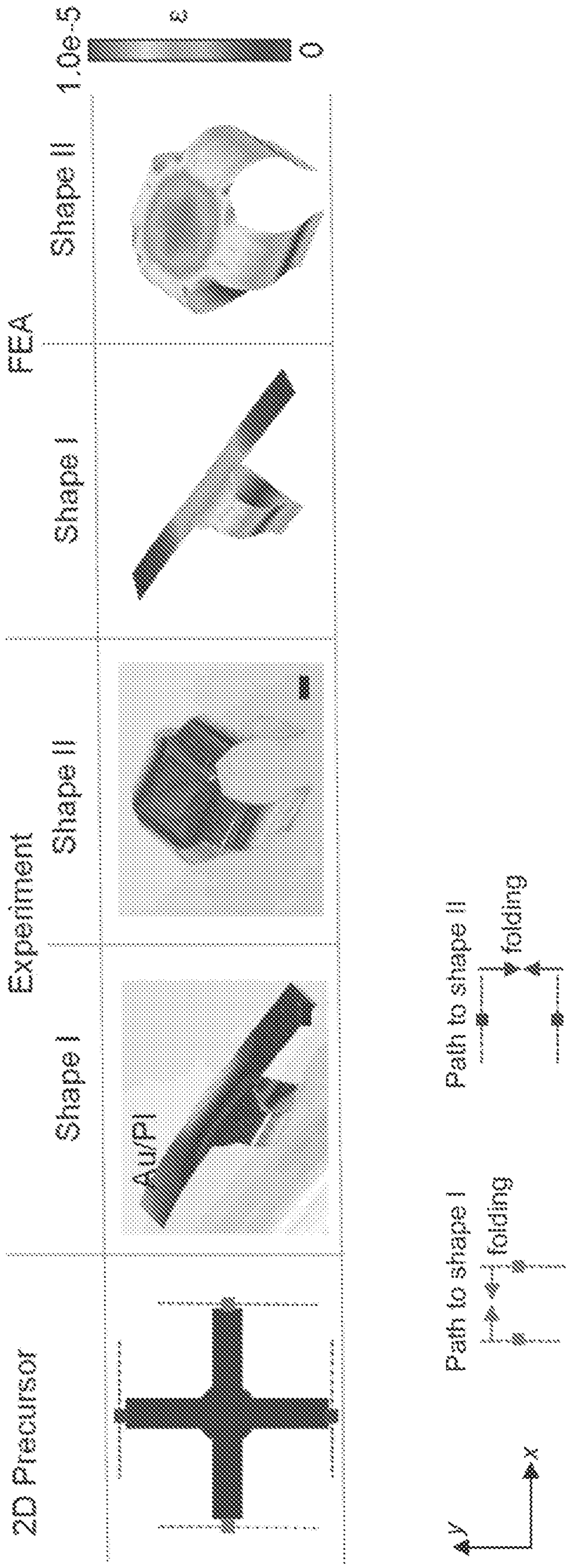

In addition, switching folding registration is also applicable to complex reconfigurable three-dimensional mesostructures with hybrid ribbon/circle geometries, as shown in example portion 3905 of FIG. 39 and the example portion 4004 of FIG. 40A.

The example portion 3907 of FIG. 39 provides three-dimensional mesostructures with geometric complexity constructed in Au/PI bilayer with periodic ribbon patterns, where a birdcage and spiked sticks are assembled through folding along x-axis and y-axis, respectively. The strain distributions of both partially and fully folded configurations of all these cases, shown by FEA simulation, indicate that $\varepsilon_{max}$ of these three-dimensional mesostructures are well below the fracture thresholds of corresponding materials and excellent agreements with the corresponding experimental observations.

Example Transformable Epicardial Bioelectronic Probe

In the present disclosure, the term "epicardial bioelectronic probe" refers to a surgical instrument that can be placed on an epicardial region of a heart (e.g. the inner layer of pericardium that closely envelops the heart) to measure, monitor, and/or detect various cardiovascular parameters associated with the heart such as, but not limited to, contractility of local cardiac tissues, cardiac output, and stroke volume, and/or the like.

Various embodiments of the present disclosure provide example apparatus, methods, and systems for fabricating example three-dimensional epicardial bioelectronic probes that are morphable/transformable. In particular, an example three-dimensional epicardial bioelectronic probe in accordance with some embodiments of the present disclosure can be enclosed in a catheter structure with a minimally invasive modality of intrapericardial insertion. In some embodiments, probing epicardial surfaces via minimally invasive approaches can enable real-time, continuous monitoring of contractility of local cardiac tissues, cardiac output, and stroke volume, which are essential in discovering and treating heart diseases with enhanced precision and timeliness. As such, example three-dimensional morphable epicardial bioelectronic probes fabricated in accordance with various embodiments of the present disclosure can provide technical advantages and benefits.

Referring now to FIG. 41, an example method 4100 of fabricating an example three-dimensional morphable epicardial bioelectronic probe in accordance with some embodiments of the present disclosure is illustrated.

In the example shown in FIG. 41, the example method 4100 starts at step/operation 4101. In some embodiments, subsequent to step/operation 4101, the example 4100 proceeds to step/operation 4103. At step/operation 4103, the example method 4100 forms an epicardial bioelectronic precursor.

In the present disclosure, the term "epicardial bioelectronic precursor" refers to a structure based on which a three-dimensional morphable epicardial bioelectronic probe can be formed. Referring now to FIG. 42, FIG. 43A, FIG. 43B, and FIG. 43C, example illustrations associated with example epicardial bioelectronic precursors in accordance with some embodiments of the present disclosure are provided. FIG. 42, FIG. 43A, FIG. 43B, and FIG. 43C present the planar form of an epicardial bioelectronic system including a substrate layer of polyimide (PI) (for example, having 10 μm in thickness) in a flower-shaped geometry with four petals (also referred to as cantilever portions), four resistive strain sensors comprising gold (Au) serpentine resistors (for example, having 50 nm in thickness) laying on the petals/cantilever portions separately, and an encapsulation top layer of parylene (for example, having 2 μm in thickness).

Figure 42:
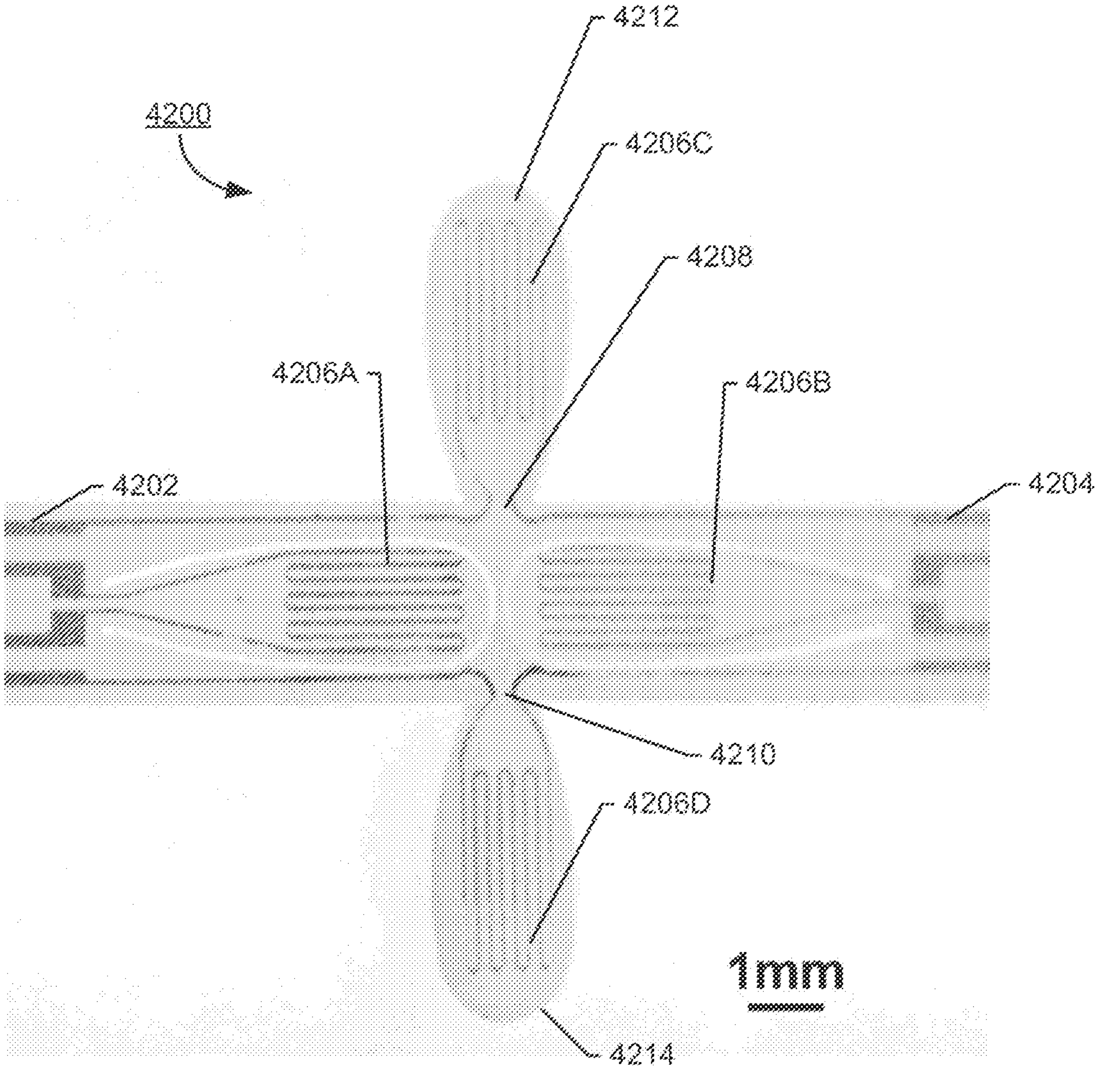
FIG. 42 illustrates an example optical image of an example epicardial bioelectronic precursor in accordance with some embodiments of the present disclosure.

Referring now to FIG. 42, an example optical image of an example epicardial bioelectronic precursor 4200 in accordance with some embodiments of the present disclosure is provided.

In some embodiments, the epicardial bioelectronic precursor 4200 comprises a first precursor end portion 4202 and a second precursor end portion 4204. In some embodiments, the first precursor end portion 4202 is opposite to the second precursor end portion 4204.

In some embodiments, the example epicardial bioelectronic precursor 4200 comprises one or more strain sensors. In the present disclosure, the terms "strain sensor" or "strain gauge" refer to a type of sensor that generates measurement signals indicating the amount of strain that it receives. For example, an example strain sensor in accordance with some embodiments of the present disclosure may comprise metal wires forming a strain sensitive pattern. In such an example, when strain is applied on the strain sensitive pattern, the strain sensitive pattern deforms, resulting in a change in the electrical resistance of the strain sensitive pattern. As such, the example strain sensor may generate measurement signals based on the changes in the electrical resistance to indicate the amount of strain that it receives.

In some embodiments, the example epicardial bioelectronic precursor 4200 comprises at least one strain sensor that is positioned between the first precursor end portion 4202 and the second precursor end portion 4204. For example, the example epicardial bioelectronic precursor 4200 comprises a strain sensor 4206A that is positioned between the first precursor end portion 4202 and the second precursor end portion 4204. Additionally, or alternatively, the example epicardial bioelectronic precursor 4200 comprises a strain sensor 4206B that is positioned between the first precursor end portion 4202 and the second precursor end portion 4204. Additionally, or alternatively, the example epicardial bioelectronic precursor 4200 comprises a strain sensor 4206C that is positioned between the first precursor end portion 4202 and the second precursor end portion 4204. Additionally, or alternatively, the example epicardial bioelectronic precursor 4200 comprises a strain sensor 4206D that is positioned between the first precursor end portion 4202 and the second precursor end portion 4204.

In some embodiments, the epicardial bioelectronic precursor 4200 comprises a strain sensor 4206A that is positioned on the first precursor end portion 4202 and a strain sensor 4206B that is positioned on the second precursor end portion 4204.

In the example shown in FIG. 42, at least a portion of the periphery of the strain sensor 4206A is cut off from the first precursor end portion 4202, such that the strain sensor 4206A can pop up when the epicardial bioelectronic precursor 4200 is transformed into a three-dimensional epicardial bioelectronic probe, details of which are described herein Similarly, at least a portion of the periphery of the strain sensor 4206B is cut off from the second precursor end portion 4204, such that the strain sensor 4206B can pop up when the epicardial bioelectronic precursor 4200 is transformed into a three-dimensional epicardial bioelectronic probe, details of which are described herein.

In some embodiments, the epicardial bioelectronic precursor comprises a strain sensor 4206C that is positioned on a first side 4208 of the epicardial bioelectronic precursor 4200 and between the first precursor end portion 4202 and the second precursor end portion 4204. For example, the strain sensor 4206C is disposed on a cantilever portion 4212. In such an example, the cantilever portion 4212 is positioned between the first precursor end portion 4202 and the second precursor end portion 4204 and extends from the first side 4208 of the epicardial bioelectronic precursor 4200.

In some embodiments, the epicardial bioelectronic precursor comprises a strain sensor 4206D that is positioned on a second side 4210 of the epicardial bioelectronic precursor 4200 and between the first precursor end portion 4202 and the second precursor end portion 4204. For example, the strain sensor 4206D is disposed on a cantilever portion 4214. In such an example, the cantilever portion 4214 is positioned between the first precursor end portion 4202 and the second precursor end portion 4204 and extends from the second side 4210 of the epicardial bioelectronic precursor 4200.

In some embodiments, the first side 4208 of the epicardial bioelectronic precursor 4200 is opposite to the second side 4210 of the epicardial bioelectronic precursor 4200. In other words, the cantilever portion 4212 extends in an opposite direction from the cantilever portion 4214.

While the description above provides an example epicardial bioelectronic precursor that comprises four strain sensors, it is noted that the scope of the present disclosure is not limited to the description above. In some examples, an example epicardial bioelectronic precursor may comprise less than four or more than four strain sensors.

Figure 43A:
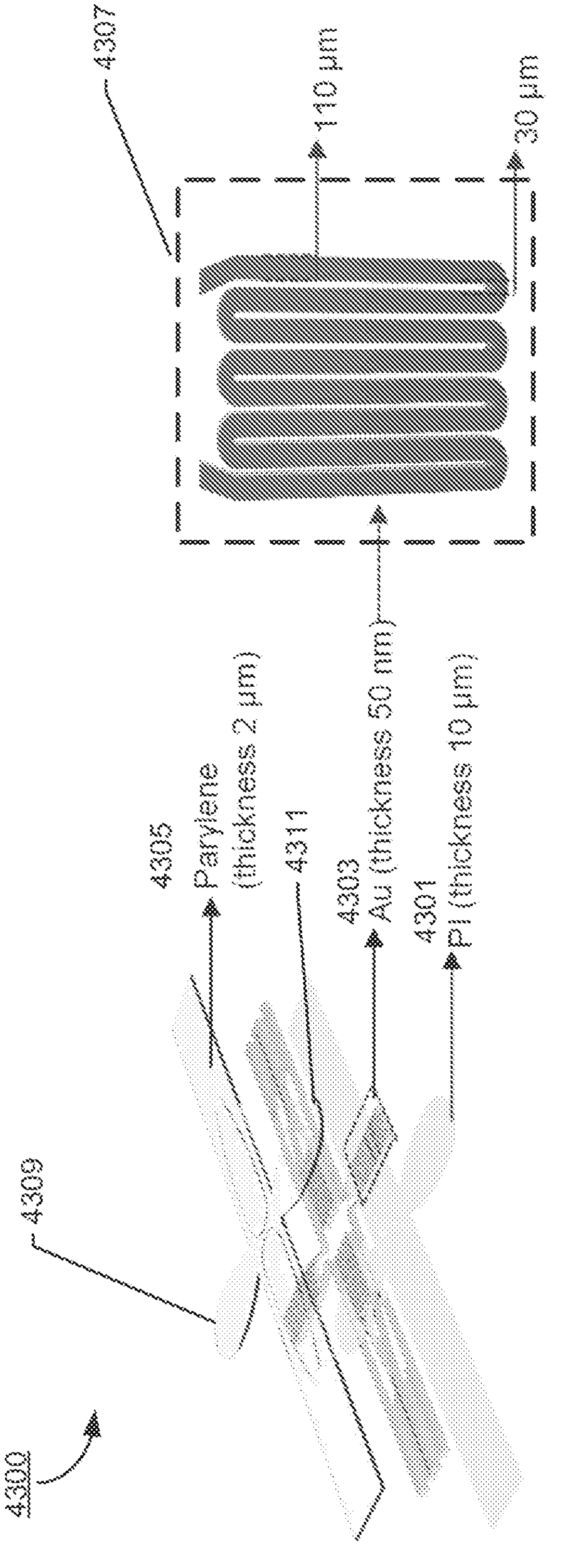
FIG. 43A illustrates an example exploded schematic view of an example epicardial bioelectronic precursor in accordance with some embodiments of the present disclosure.

Referring now to FIG. 43A, an example exploded schematic view of an example epicardial bioelectronic precursor 4300 in accordance with some embodiments of the present disclosure is provided.

Figure 43B:
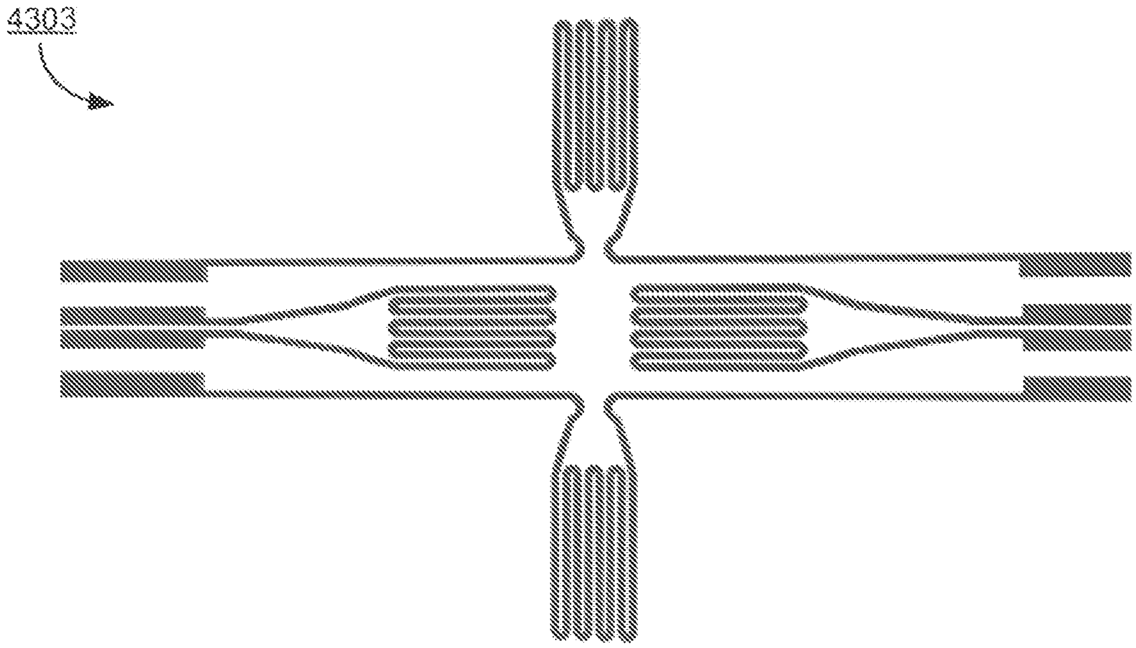
FIG. 43B illustrates an example gold layer of an example epicardial bioelectronic precursor in accordance with some embodiments of the present disclosure.
Figure 43C:
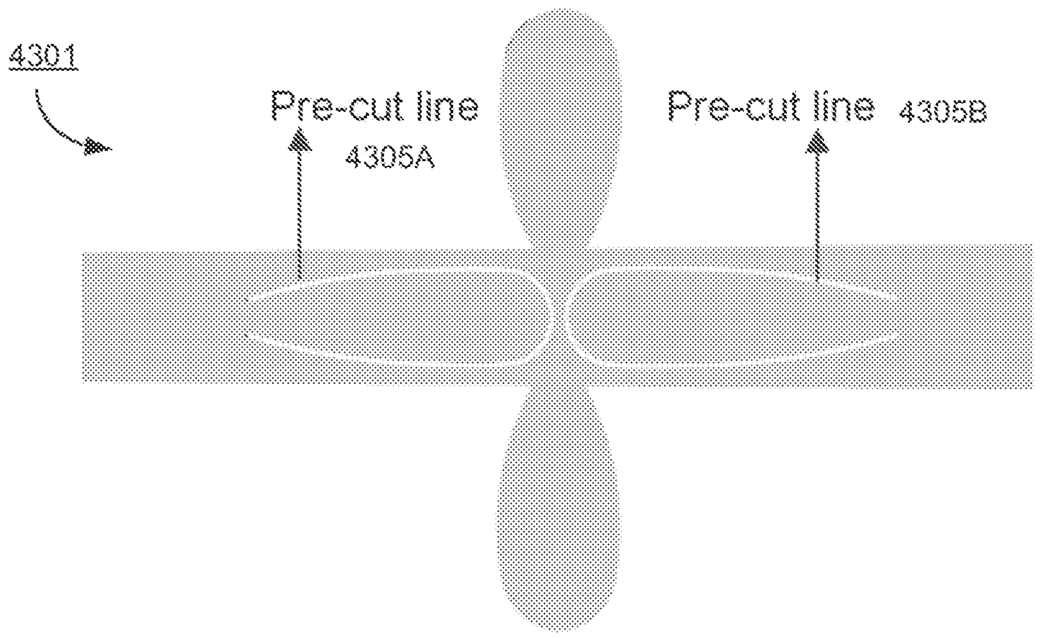
FIG. 43C illustrates an example polyester layer of an example epicardial bioelectronic precursor in accordance with some embodiments of the present disclosure.

In the example shown in FIG. 43A, the epicardial bioelectronic precursor 4300 comprises a polyester layer 4301. In some embodiments, a polyester layer thickness associated with the polyester layer 4301 is 10 μm. FIG. 43C further illustrates the polyester layer 4301 with the pre-cut line 4305A and the pre-cut line 4305B for forming the cantilever portions as described herein.

In some embodiments, the epicardial bioelectronic precursor 4300 comprises a gold layer 4303 disposed on top of the polyester layer. In some embodiments, a gold layer thickness associated with the gold layer 4303 is 50 nm. FIG. 43B further illustrates the gold layer 4303.

In some embodiments, the epicardial bioelectronic precursor 4300 comprises a parylene layer 4305 disposed on top of the gold layer. In some embodiments, a parylene layer thickness associated with the parylene layer 4305 is 2 μm.

The example combinations of materials and their associated thicknesses can provide technical advantages and benefits such as, but not limited to, an optimized balance between rigidness and flexibility of the epicardial bioelectronic probe.

In some embodiments, the epicardial bioelectronic precursor 4300 comprises a cantilever portion 4309 and a cantilever portion 4311, similar to those described above in connection with at least FIG. 42. In some embodiments, each of the cantilever portion 4309 and the cantilever portion 4311 comprises the polyester layer 4301, the gold layer 4303, and the parylene layer 4305 as described above.

As described above, an example epicardial bioelectronic precursor in accordance with some embodiments of the present disclosure comprises one or more strain sensors. In some embodiments, each of the strain sensor(s) comprises metal wires forming a strain sensitive pattern. In the example shown in FIG. 43A, the at least one strain sensor comprises at least one gold wire forming a strain sensitive pattern 4307 on the gold layer 4303.

In the example shown in FIG. 43A, a wire width associated with the at least one gold wire that forms the strain sensitive pattern is 110 μm. In the present disclosure, a "gap width" associated with the strain sensitive pattern refers to a width between two neighboring gold wires that form the strain sensitive pattern. In the example shown in FIG. 43A, the gap width associated with the strain sensitive pattern 4307 is 30 μm.

Figure 46:
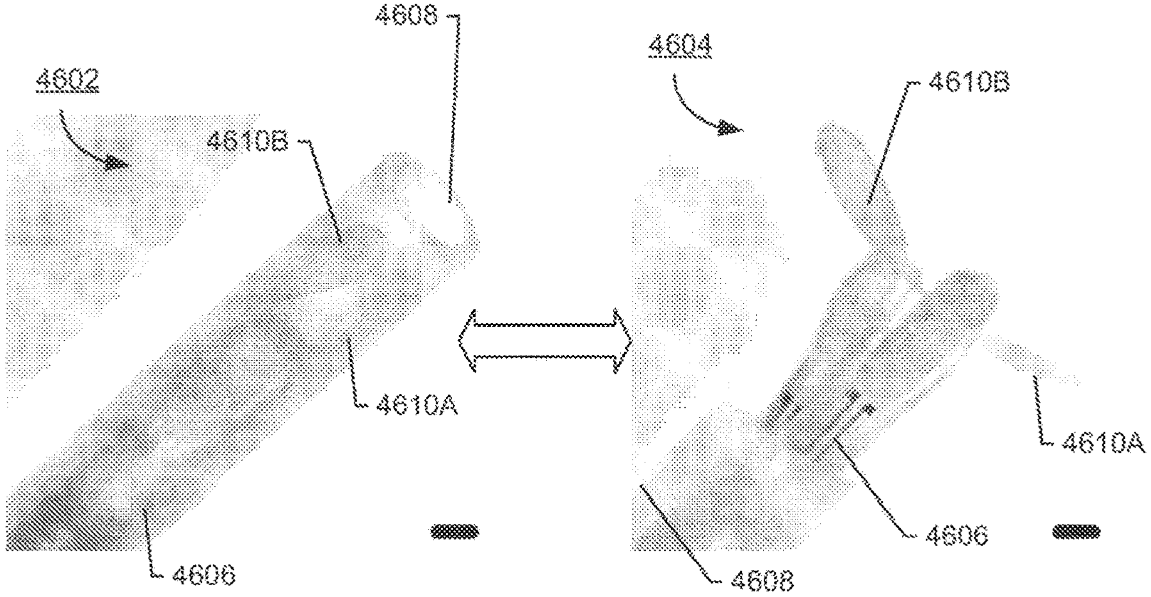
FIG. 46 illustrates example optical images showing an example blooming process of an example three-dimensional epicardial bioelectronic probe from an example catheter in accordance with some embodiments of the present disclosure.

In some embodiments, an example method of fabricating an example epicardial bioelectronic precursor comprises depositing a thin gold film layer (for example, having a thickness of approximately 50 nm) on the polyimide (PI) film (for example, having a thickness of approximately 10 μm) through magnetron sputtering. In some embodiments, the example method comprises forming a planar epicardial bioelectronic patch with the parameterization using the laser cutting machine. In some embodiments, the planar epicardial bioelectronic patch is the epicardial bioelectronic precursor. In some embodiments, the three-dimensional epicardial bioelectronic probe with strain sensors were achieved by folding the epicardial bioelectronic precursor on a predefined folding host. In some embodiments, the as-prepared three-dimensional probe can be attached to a catheter as shown in FIG. 46.

Referring back to FIG. 41, subsequent to step/operation 4103, the example 4100 proceeds to step/operation 4105. At step/operation 4105, the example method 4100 binds or bonds the epicardial bioelectronic precursor to a folding host in an unfolded state.

Similar to those described above in connection with at least FIG. 1A and FIG. 1B, the folding host comprises a first bonding site portion and a second bonding site portion, and defines a trench portion between the first bonding site portion and the second bonding site portion.

In some embodiments, when bonding the epicardial bioelectronic precursor to a folding host, the example method 4100 comprises bonding the first precursor end portion of the epicardial bioelectronic precursor to the first bonding site portion, and bonding the second precursor end portion of the epicardial bioelectronic precursor to the second bonding site portion.

For example, referring now to FIG. 42, as described above, the example epicardial bioelectronic precursor 4200 comprises a first precursor end portion 4202 and a second precursor end portion 4204. In some embodiments, the first precursor end portion 4202 of the epicardial bioelectronic precursor 4200 is bonded to the first bonding site portion of the folding host, and the second precursor end portion 4204 of the epicardial bioelectronic precursor 4200 is bonded to the second bonding site portion of the folding host.

Referring back to FIG. 41, subsequent to step/operation 4105, the example 4100 proceeds to step/operation 4107. At step/operation 4107, the example method 4100 shapes the epicardial bioelectronic precursor to the three-dimensional epicardial bioelectronic probe by transforming the folding host from the unfolded state to a folded state.

Similar to those described above in connection with at least FIG. 1A and FIG. 1B, the example method 4100 comprises exerting folding motions on the first bonding site portion and the second bonding site portion along a trench axis of the trench portion to transform the folding host from the unfolded state to a folded state.

Figure 44:
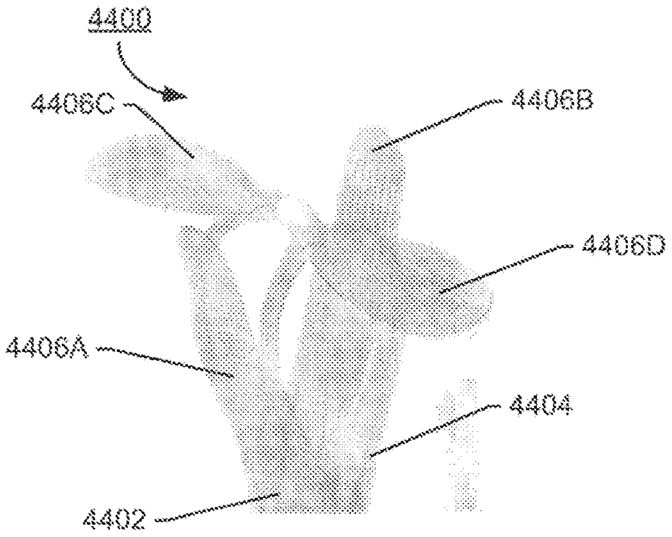
FIG. 44 illustrates an example optical image of an example fully bloomed three-dimensional epicardial bioelectronic probe in accordance with some embodiments of the present disclosure.
Figure 45:
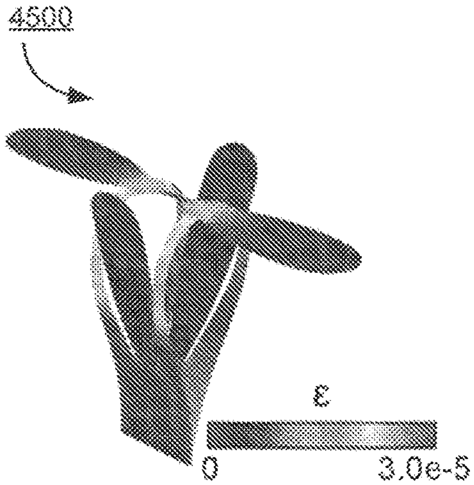
FIG. 45 illustrates example FEA results of an example fully bloomed three-dimensional epicardial bioelectronic probe in accordance with some embodiments of the present disclosure.

For example, referring now to FIG. 44 and FIG. 45, an example three-dimensional epicardial bioelectronic probe 4400 and its corresponding FEA results 4500 are illustrated. For example, FIG. 44 and FIG. 45 show the optical image and corresponding FEA result of a fully bloomed three-dimensional epicardial bioelectronic probe obtained from the two-dimensional integrated electronics via the micro-folding assembly.

In particular, to shape the epicardial bioelectronic precursor to the three-dimensional epicardial bioelectronic probe, the first precursor end portion 4402 and the second precursor end portion 4404 are attached to one another.

Similar to those described above in connection with FIG. 42, the epicardial bioelectronic precursor comprises a strain sensor 4406A that is positioned on the first precursor end portion 4402 and a strain sensor 4406B that is positioned on the second precursor end portion 4404. In some embodiments, portions of peripheries of the strain sensor 4406A and the strain sensor 4406B are cut off from the first precursor end portion 4402 and the second precursor end portion 4404, respectively. As such, when the first precursor end portion 4402 and the second precursor end portion 4404 are attached to one another, the strain sensor 4406A and the strain sensor 4406B pop up from the first precursor end portion 4402 and the second precursor end portion 4404, respectively.

Similar to those described above in connection with FIG. 42, the epicardial bioelectronic precursor comprises a strain sensor 4406C and a strain sensor 4406D that are positioned on opposite sides of the example three-dimensional epicardial bioelectronic probe 4400 and between the first precursor end portion 4402 and the second precursor end portion 4404. In some embodiments, when the first precursor end portion 4402 and the second precursor end portion 4404 are attached to one another, the strain sensor 4406C and the strain sensor 4406D remains coplanar and become orthogonal to the first precursor end portion 4402 and the second precursor end portion 4404.

Referring back to FIG. 41, subsequent to step/operation 4109, the example 4100 proceeds to step/operation 4109. At step/operation 4109, the example method 4100 encapsulates the three-dimensional epicardial bioelectronic probe in a catheter.

In some embodiments, when encapsulating the three-dimensional epicardial bioelectronic probe in a catheter, the example method 4100 comprises causing the at least one strain sensor to retract within the catheter.

As described herein, the epicardial bioelectronic probe can be encapsulated into a catheter due to its mechanical softness and deformability. FIG. 46 provides an example illustration 4602 where the three-dimensional epicardial bioelectronic probe 4606 is encapsulated in the catheter 4608, and an example illustration 4604 where the three-dimensional epicardial bioelectronic probe 4606 is released from the catheter 4608. As such, the example illustration 4602 to the example illustration 4604 provides an example blooming process of the three-dimensional epicardial bioelectronic probe 4606 from the catheter 4608.

In the example shown in FIG. 46, when encapsulating the three-dimensional epicardial bioelectronic probe 4606 in the catheter 4608, the strain sensor 4610A and the strain sensor 4610B are retracted within the catheter 4608. In particular, the strain sensor 4610A and the strain sensor 4610B are positioned on opposite sides of the epicardial bioelectronic precursor and between the first precursor end portion and the second precursor end portion of the epicardial bioelectronic precursor as described above.

Referring back to FIG. 41, subsequent to step/operation 4109, the example 4100 proceeds to step/operation 4111 and ends.

In accordance with some embodiments of the present disclosure, an example three-dimensional epicardial bioelectronic probe provides flower-like architecture that can undergo shape transformation from closure to opening spatially and reversibly as shown in FIG. 47A to FIG. 47F. For example, the three-dimensional epicardial bioelectronic probe in a closed state can safely travel in the thoracic cavity or through the vein to the heart via the catheter. Once it reaches the desired location, the catheter is retracted, and the flower structure of the three-dimensional epicardial bioelectronic probe emerges immediately to engage closely with targeted tissues.

In particular, FIG. 47A to FIG. 47F illustrate various example states associated with an example three-dimensional epicardial bioelectronic probe system 4700.

In some embodiments, the example three-dimensional epicardial bioelectronic probe system 4700 comprises a catheter 4701 and a three-dimensional epicardial bioelectronic probe 4705.

In some embodiments, the three-dimensional epicardial bioelectronic probe 4705 comprises at least one cantilever portion 4707. In some embodiments, the at least one cantilever portion 4707 comprises a polyester layer, a gold layer disposed on top of the polyester layer, and a parylene layer disposed on top of the gold layer, similar to those described above in connection with at least FIG. 43A.

In some embodiments, a polyester layer thickness associated with the polyester layer is 10 μm, similar to that of the polyester layer 4301 described above in connection with at least FIG. 43A. In some embodiments, a gold layer thickness associated with the gold layer is 50 nm, similar to that of the gold layer 4303 described above in connection with at least FIG. 43A. In some embodiments, a parylene layer thickness associated with the parylene layer is 2 μm, similar to that of the parylene layer 4305 described above in connection with at least FIG. 43A.

Similar to those described above in connection with at least FIG. 43A, at least one strain sensor is on the gold layer and comprises at least one gold wire forming a strain sensitive pattern. In some embodiments, a wire width associated with the at least one gold wire is 110 μm. In some embodiments, a gap width associated with the strain sensitive pattern is 30 μm.

In some embodiments, the catheter 4701 defines a distal opening 4703. In particular, the distal opening 4703 refers to the opening of the catheter 4701 through which the three-dimensional epicardial bioelectronic probe 4705 can extend out of the catheter 4701 or retract into the catheter 4701.

In some embodiments, the three-dimensional epicardial bioelectronic probe 4705 comprises a probe end portion 4709 positioned in the catheter 4701. As described above, the three-dimensional epicardial bioelectronic probe 4705 can be formed by bonding the first precursor end portion with the second precursor end portion. In some embodiments, the probe end portion 4709 refers to the portion of the three-dimensional epicardial bioelectronic probe 4705 where the first precursor end portion and the second precursor end portion are bonded together.

In some embodiments, the probe end portion 4709 of the three-dimensional epicardial bioelectronic probe 4705 is moveable between a proximal end of the catheter 4701 and a distal end of the catheter 4701. In some embodiments, the distal end of the catheter 4701 is the end of the catheter 4701 where the distal opening 4703 is located. In some embodiments, the proximal end of the catheter 4701 is opposite to the distal end of the catheter 4701.

Figure 47A:
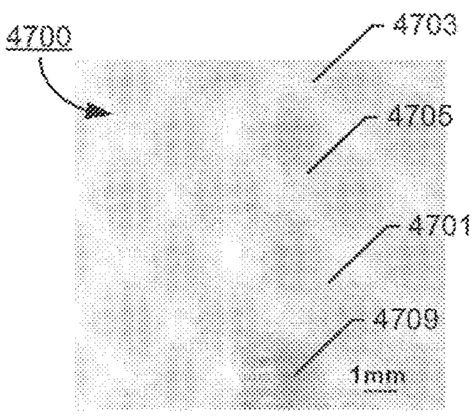
FIG. 47A, FIG. 47B, FIG. 47C, FIG. 47D, FIG. 47E, and FIG. 47F provide example optical images showing an example blooming process of an example three-dimensional epicardial bioelectronic probe in accordance with some embodiments of the present disclosure.

In some embodiments, a movement of the probe end portion 4709 from the proximal end of the catheter 4701 to the distal end of the catheter 4701 causes the three-dimensional epicardial bioelectronic probe 4705 to transform from the closed state to the open state. For example, FIG. 47A illustrates the three-dimensional epicardial bioelectronic probe 4705 in a fully closed state, and FIG. 47F illustrates the three-dimensional epicardial bioelectronic probe 4705 in a fully open state. FIG. 47A to FIG. 47F illustrate a transformation of the three-dimensional epicardial bioelectronic probe 4705 from a fully closed state to a fully open state.

Figure 47B:
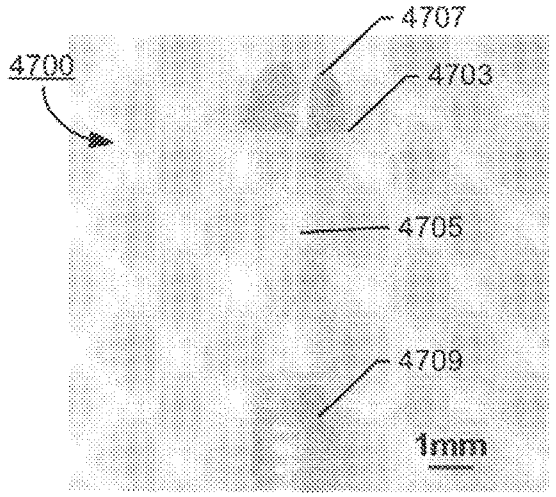
Figure 47C:
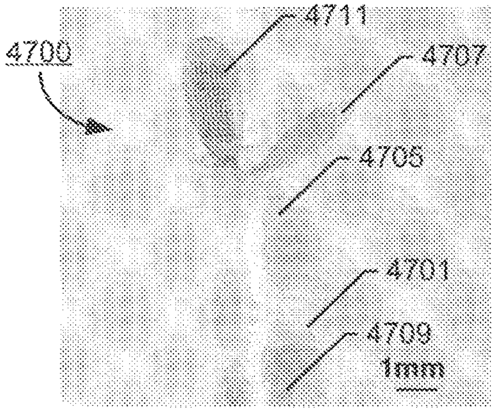
Figure 47D:
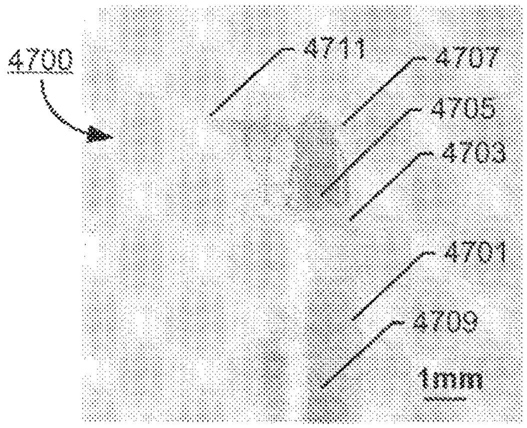

As shown in FIG. 47A and FIG. 47B, when the three-dimensional epicardial bioelectronic probe 4705 is in a fully closed state or a partially closed state, the three-dimensional epicardial bioelectronic probe 4705 is encapsulated in the catheter 4701. In particular, when the three-dimensional epicardial bioelectronic probe 4705 is in a fully closed state, the catheter 4701 covers the three-dimensional epicardial bioelectronic probe 4705 entirely as shown in FIG. 47A. When the three-dimensional epicardial bioelectronic probe 4705 is in a partially closed state, the catheter 4701 covers at least some or most of the three-dimensional epicardial bioelectronic probe 4705 as shown in FIG. 47B.

In some embodiments, when the three-dimensional epicardial bioelectronic probe 4705 is in the closed state, the at least one cantilever portion 4707 is positioned in the catheter 4701 and oriented towards the distal opening 4703 of the catheter 4701. For example, during encapsulation, the probe end portion 4709 of the three-dimensional epicardial bioelectronic probe 4705 moves from the distal end of the catheter 4701 to the proximal end of the catheter 4701, pulling the at least one cantilever portion 4707 along the catheter 4701. As such, when encapsulated, the at least one cantilever portion 4707 is oriented towards the distal opening 4703 of the catheter 4701.

In some embodiments, when the three-dimensional epicardial bioelectronic probe 4705 is in the closed state, the at least one cantilever portion 4707 is in a parallel arrangement with the catheter 4701, as shown in FIG. 47B. For example, a longitudinal axis of the at least one cantilever portion 4707 is parallel to or approximately parallel to a longitudinal axis of the catheter 4701.

Figure 47E:
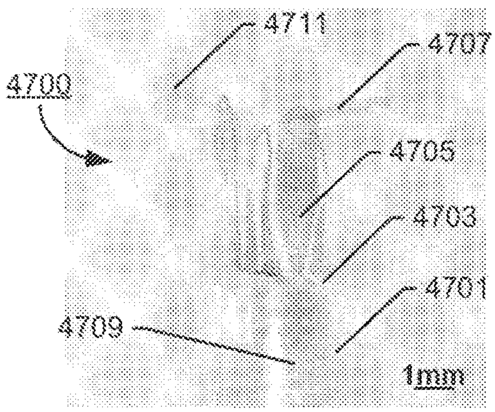
Figure 47F:
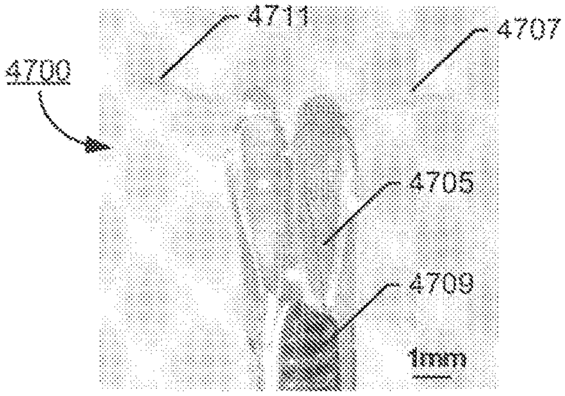

As shown in FIG. 47E and FIG. 47F, when the three-dimensional epicardial bioelectronic probe 4705 is in a fully open state or a partially open state, the at least one cantilever portion 4707 is in a non-parallel arrangement with the catheter 4701, as shown in FIG. 47E.

For example, the at least one cantilever portion 4707 may be disposed between the first precursor end portion and the second precursor end portion as described above. Because the first precursor end portion and the second precursor end portion are bonded together to form the probe end portion 4709 that moves within the catheter 4701, the at least one cantilever portion 4707 is in a non-parallel arrangement with the catheter 4701. In some embodiments, the at least one cantilever portion 4707 is in an orthogonal arrangement with the catheter 4701.

In some embodiments, when the three-dimensional epicardial bioelectronic probe 4705 is in the open state, the at least one cantilever portion 4707 and the at least one cantilever portion 4711 are positioned out of the catheter 4701 and arranged radially around the distal opening 4703 of the catheter 4701, as shown in FIG. 47D, FIG. 47E, and FIG. 47F.

Referring now to FIG. 48 to FIG. 55, example images and diagrams associated with example in vivo animal experiment based at least in part on implementing an example transformable epicardial bioelectronic probe in accordance with some embodiments of the present disclosure are provided.

In the example in vivo animal experiment, testing animals in the form of female mice having weights between 20 to 30 g and ages of 10 weeks were purchased. The testing animals were kept on a 12-hour light-dark cycle in a temperature-controlled room. The testing animals were initially placed under anesthesia in a chamber with isoflurane gas (including 5% isoflurane and 100% oxygen). Once consciousness was lost, the testing animals were intubated with a 16-gauge flexible catheter, and endotracheal tube was connected to a mechanical ventilator that provided positive-pressure ventilation with oxygen/isoflurane. The ventilator was set based on animal weight: tidal volume (Vt, milliliters)=6.2×M1.01 and RR (min-1)=53.5χM–0.26, where M is the animal weight in kilograms.

In the above in vivo animal experiment, each testing animal was connected to a vaporizer that delivers approximately 2.0% isoflurane driven by 100% oxygen. Testing animals were placed in the dorsal decubitus position on a warming platform. Intradermal bupivicaine was infiltrated at the incision sites approximately 10 min before incisions. Testing animals were maintained at approximately 37° C. on a heating pad, with body temperature monitored throughout the experiment using a rectal temperature probe.

In the above in vivo animal experiment, the testing animal's hair was removed from the surgical site with hair removal cream after shaving. The surgical areas were scrubbed and disinfected with a povidone iodine prep pad, and the area was then wiped with an alcohol prep pad. Peripheral blood oxygen saturation of testing animals was monitored throughout the experiment using a commercial pulse oximetry system. Thoracotomy on the testing animal opened a small window for the probe to be placed on the cardiac surface, which is followed by data collection. The electrocardiography (ECG) and heart rate were monitored simultaneously using commercial equipment. The hypoxia and ischemia condition tests were conducted by adjusting the tidal volume on the ventilator and temporarily occluding the left coronary artery (LCA), respectively.

Figure 48:
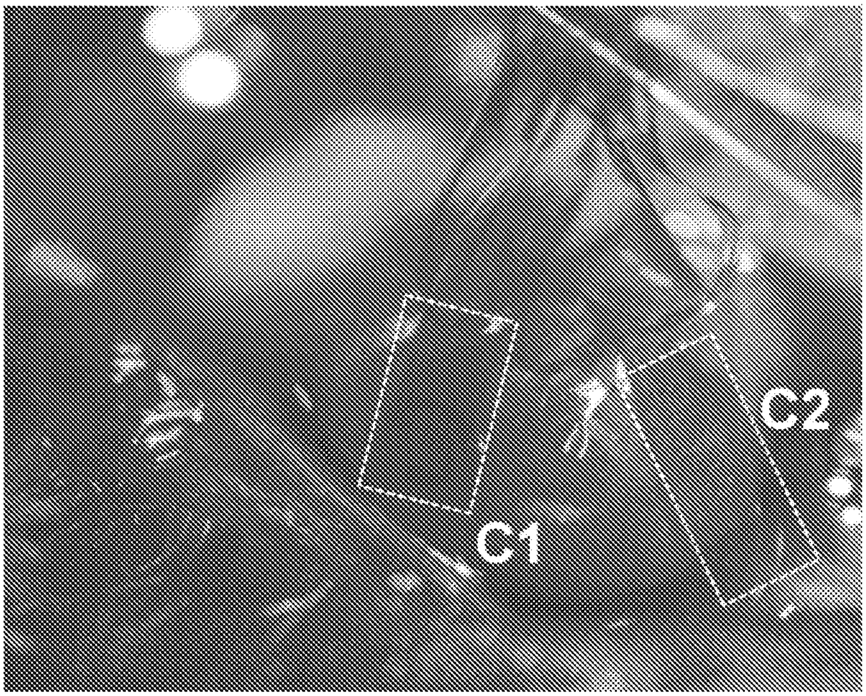
FIG. 48 illustrates an example image of an example three-dimensional epicardial bioelectronic probe deployed on an example epicardial surface of an example living mouse heart in accordance with some embodiments of the present disclosure.
Figure 49:
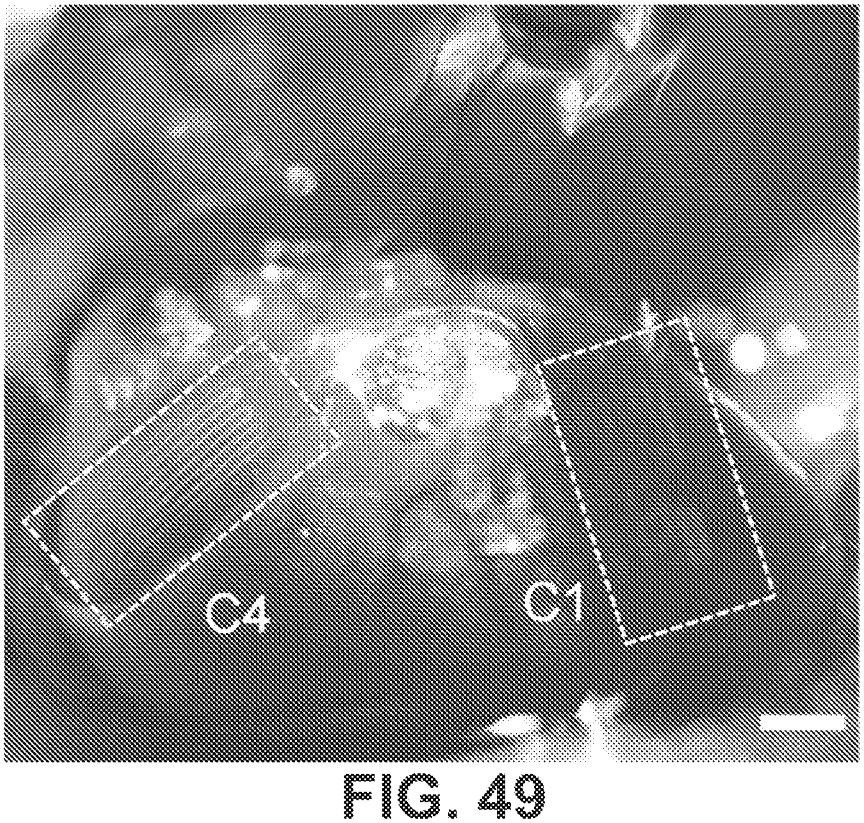
FIG. 49 illustrates an example three-dimensional epicardial bioelectronic probe with a three-dimensional flower-like architecture that is attached to an end of a catheter and positioned on an example mouse heart in accordance with some embodiments of the present disclosure.
Figure 50:
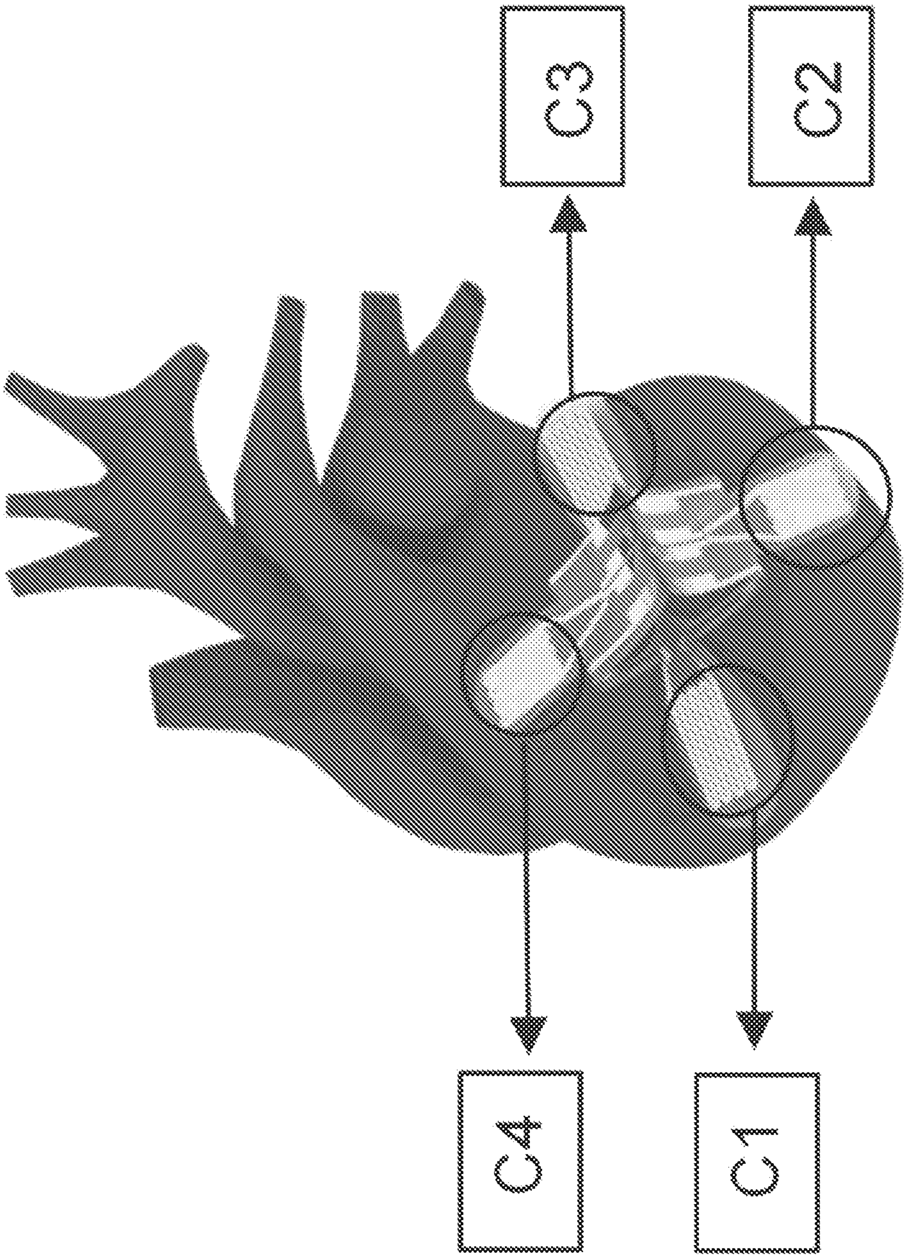
FIG. 50 provides an example schematic illustration showing an example device position of an example three-dimensional epicardial bioelectronic probe on an example mouse heart in accordance with some embodiments of the present disclosure.

FIG. 48 and FIG. 49 demonstrate a three-dimensional bioelectronic probe with an enhanced interface to geometrically irregular cardiac tissue conformally deployed on the epicardial surface of a living mouse heart. FIG. 50 demonstrates multiple strain sensors (which are labeled as C1, C2, C3, and C4) are well aligned on the petals/cantilever portions of the three-dimensional epicardial bioelectronic probe and simultaneously distributed in different areas of atrium/ventricle, gathering spatially resolved information that enables holistic monitoring of cardiac contractility, which significantly contributes to diagnosis and treatment of heart conditions.

Figure 51:
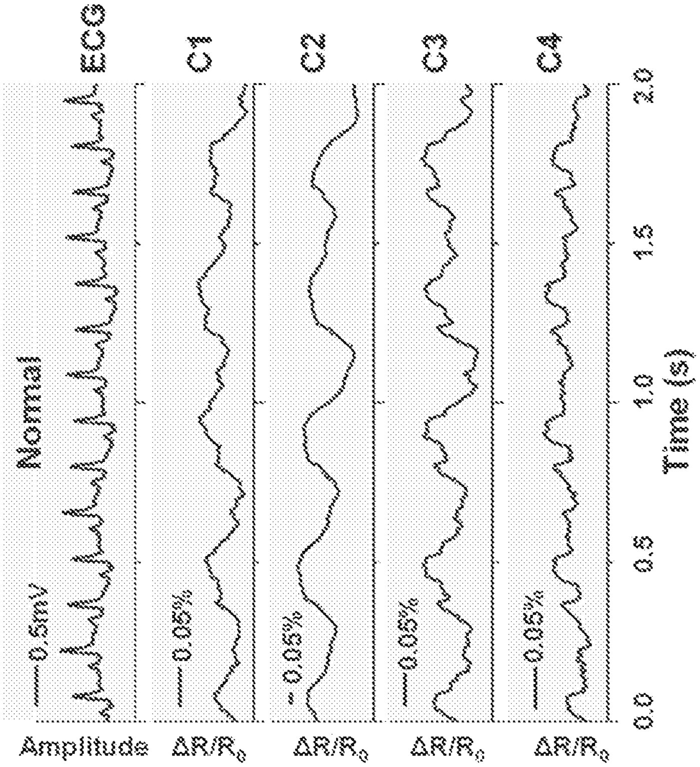
FIG. 51 provides an example diagram illustrating example representative measurements of an example epicardial bioelectronic probe placed onto an example living mouse heart under normal conditions in accordance with some embodiments of the present disclosure.
Figure 52:
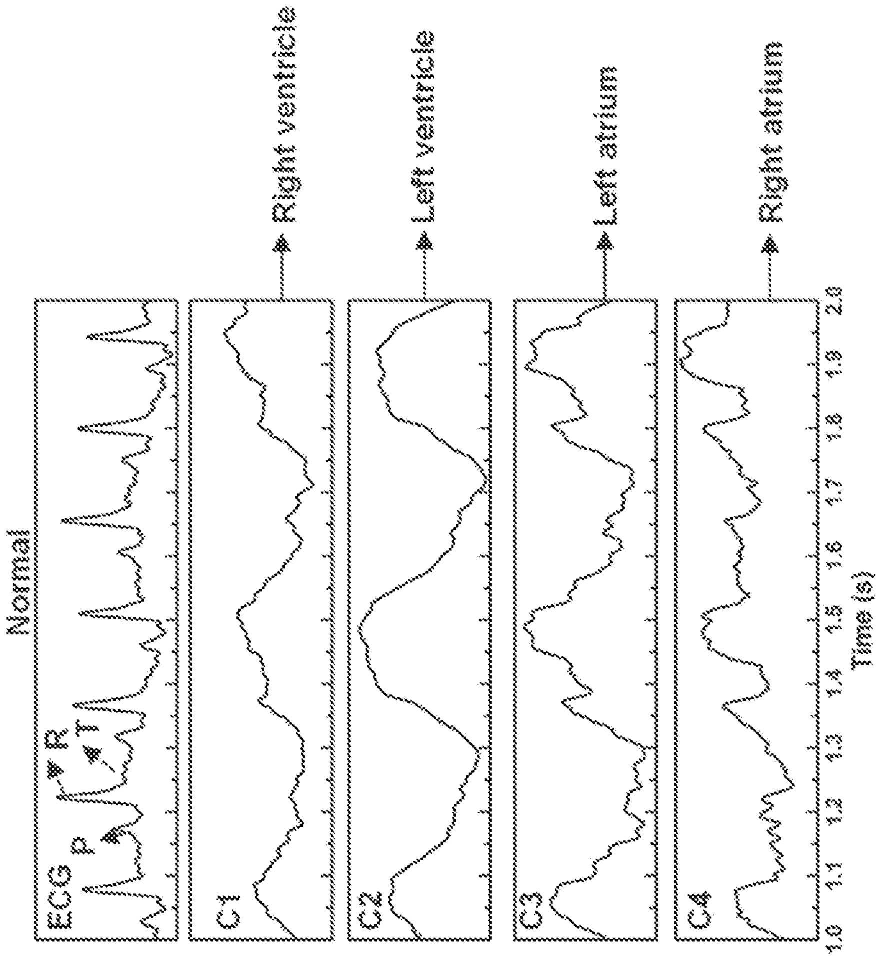
FIG. 52 provides an example diagram illustrating example representative measurements of an example epicardial bioelectronic probe placed onto an example living mouse heart under normal conditions (for example, partial pressure of oxygen was 150 mmHg) in accordance with some embodiments of the present disclosure.
Figure 53:
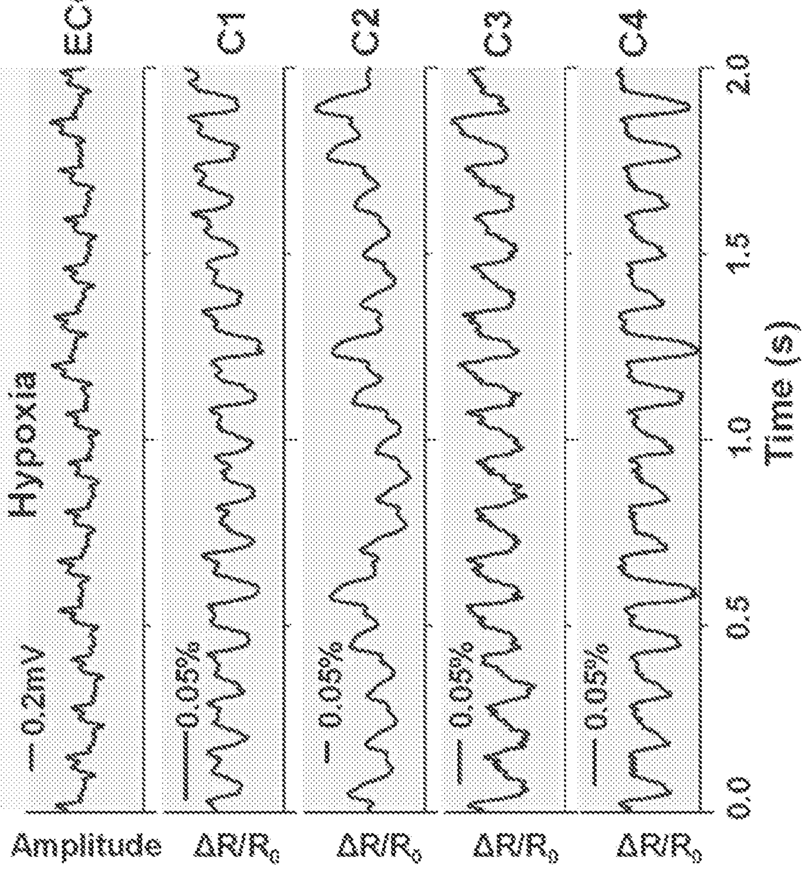
FIG. 53 provides an example diagram illustrating example representative measurements of an example epicardial bioelectronic probe placed onto an example living mouse heart under hypoxia condition in accordance with some embodiments of the present disclosure.
Figure 54:
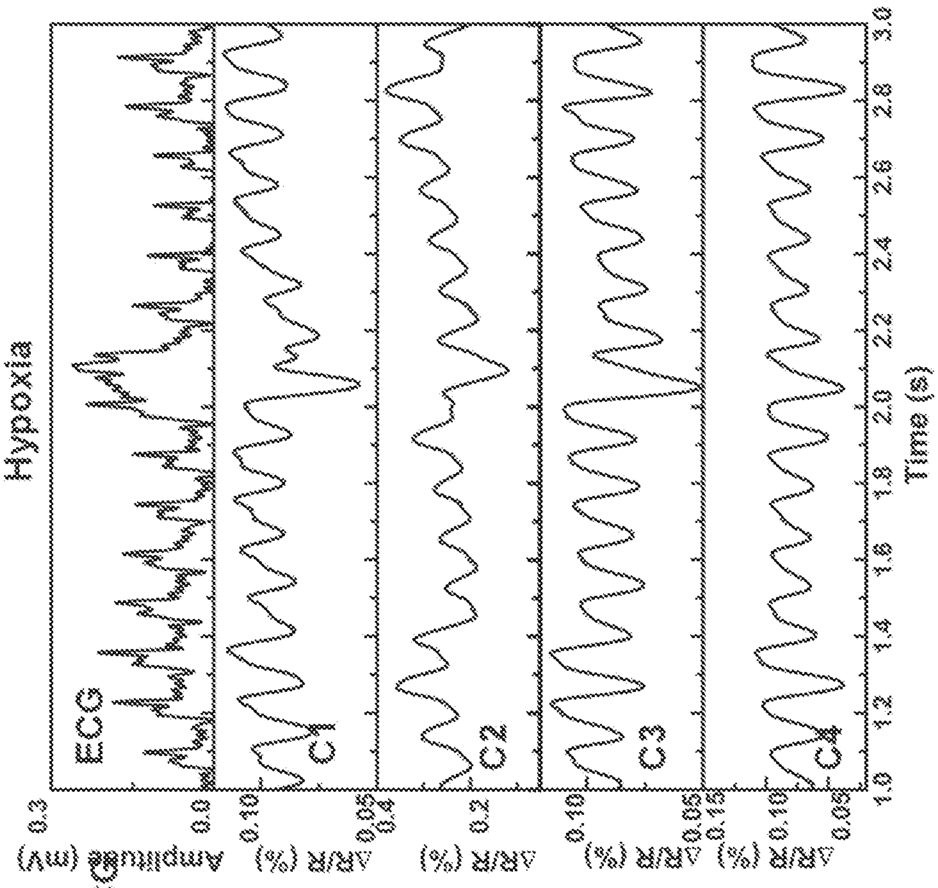
FIG. 54 provides an example diagram illustrating example representative measurements of an example epicardial bioelectronic probe placed onto an example living mouse heart under hypoxia conditions (for example, partial pressure of oxygen was 50 mmHg) in accordance with some embodiments of the present disclosure.

FIG. 51 to FIG. 55 provide representative measurements involving signals acquired from a living mouse heart for a variety of conditions including normal condition (for example, as shown in FIG. 51 and FIG. 52), hypoxia condition (for example, as shown in FIG. 53 and FIG. 54), and ST-elevation myocardial ischemia attack (as described above).

In some embodiments, the strain sensors stretch and conform in accordance with the relaxation and contraction of myocardium, which resembles the cardiac electrophysiological signals. Moreover, the electrocardiogram (ECG) recordings verify the electrical capture. FIG. 51 and FIG. 52 present that the as-prepared device enables simultaneous measurement of the specific activity of the right and left atria (RA and LA), and the right and left ventricles (RV and LV) under normal beating conditions, where the output features of the sensors will depend on their experienced strain that significantly correlates to their positions on the epicardial surface.

As shown in FIG. 52, in each healthy cardiac cycle, C3 (LA) and C4 (RA) have suppressed activity during the QRS complex while the ventricles are stimulated and increased activity during the P wave when the atria are stimulated. Similarly, C1 (RV) and C2 (LV) have the inverse activity with a suppressed P wave and increased activity during the QRS complex. In addition, the relative activation delay displayed in C1 (RV) and C4 (RA) compared with that in C2 (LV) and C3 (LA) is because the right side of the heart is usually stimulated before the left side, well corresponding to the myocardial locations at which sensors are placed.

Moreover, a hypoxemia condition is simulated, and results in FIG. 53 and FIG. 54 demonstrate that the three-dimensional epicardial bioelectronic probe is able to detect irregularities in cardiac activity, where the heart is beating faster in an attempt to receive more oxygen-rich blood, and this requires more force in order to contract at a faster rate. Therefore, all sensors experience a faster cycle with a larger amplitude due to a greater level of experienced strain. Furthermore, a simulation of an ST-elevation myocardial ischemia attack through the temporary ligation of left coronary artery (LCA) results in a lack of blood supply to the heart muscle, and further causes abnormalities in myocardial contractility especially on the left-sided heart.

Figure 55:
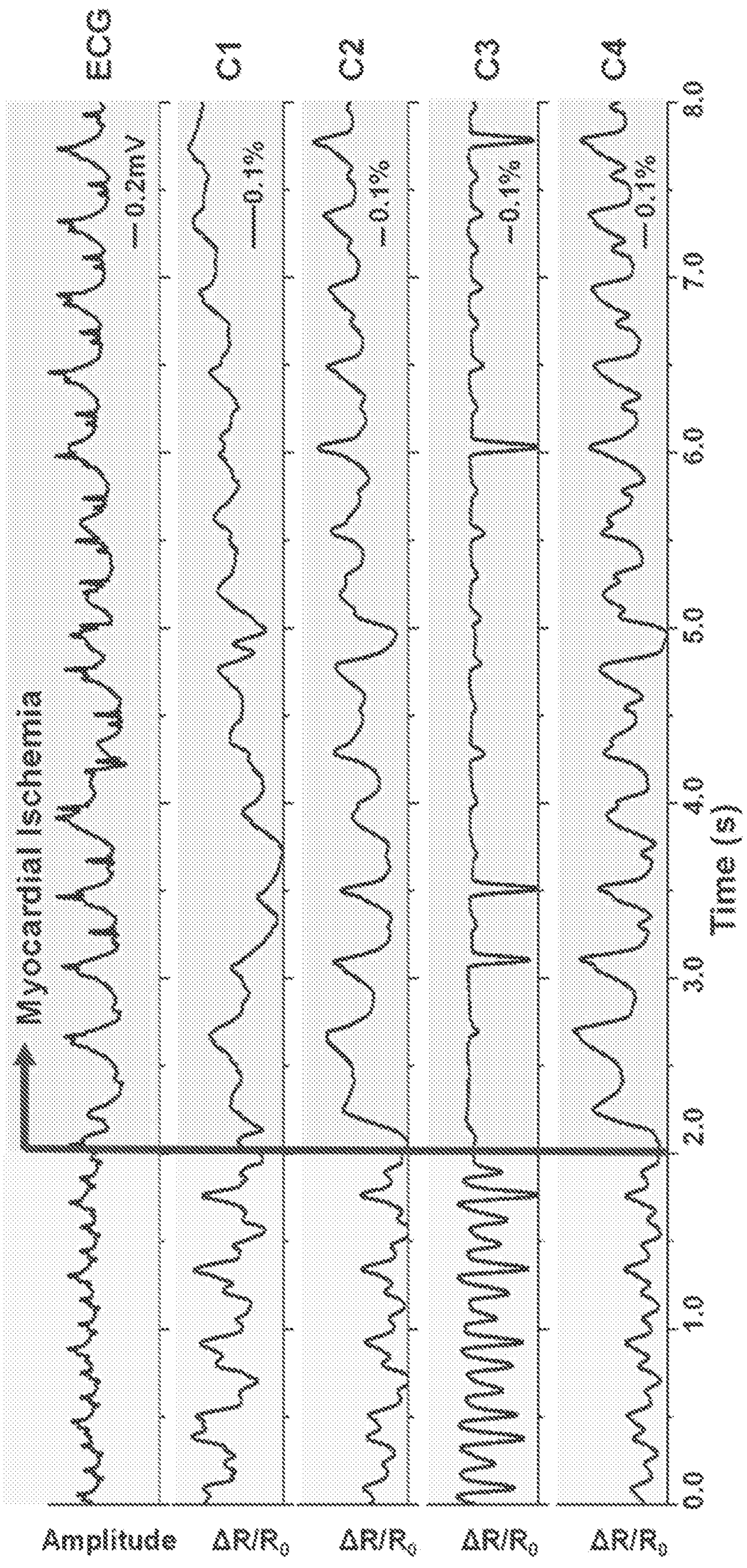
FIG. 55 provides an example diagram illustrating example representative measurements of an example epicardial bioelectronic probe placed onto an example living mouse heart conditions before and after a ST-elevation myocardial ischemia in accordance with some embodiments of the present disclosure.

Correspondingly, FIG. 55 shows the sensors C2 (LV) and C3 (LA) experience a higher increase in stimulation compared with sensors C1 (RV) and C4 (RA) when myocardial ischemia occurs, indicating the device offers sufficient sensitivity and precision in localizing the specific site of the arterial disease and other heart-related issues. Therefore, the three-dimensional bioelectronic epicardial probe provides a potential clinical utility in locating dysfunctional tissue and real-time monitoring the recovery of myocardial contractility through multiple output channels after cardiac surgery.

CONCLUSION

The present application presents a controlled, deterministic microfolding strategy for the design and fabrication of a broad set of three-dimensional mesostructures spanning from simple to complex configurations with length scales ranging from micrometers to centimeters, across material classes from soft polymers to plastic metals, and to brittle inorganic semiconductors. A scaling law is developed to guide the folding strategy and avoid material failure for a single folding ribbon, which can serve as building blocks for constructing a broad range of ribbon-based complex structures. Over a dozen examples of freestanding three-dimensional morphable mesostructures illustrate the key ideas of microfolding and validate the utility of computational modeling to enable inverse design. Moreover, various embodiments of the present disclosure provide example fabrications of three-dimensional folded-mesostructure-templated microelectronics with deterministic control of geometry. For example, various embodiments of the present disclosure provide an example morphable epicardial bioelectronic probe based on the deterministic microfolding strategy that can be enclosed in a catheter structure and travel to the heart with a minimally invasive modality of intrapericardial insertion. The example morphable epicardial bioelectronic probe is capable of strain sensing at precise three-dimensional locations to enable holistic monitoring of cardiac contractility, and its capabilities have been validated using a mice model with cardiac injury. As such, example three-dimensional mesostructures that are fabricated via example microfolding methods in accordance with some embodiments of the present disclosure demonstrate high tunability and controllability, therefore providing various technical advantages and improvements over mesostructures that are fabricated through other methods.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. A method for fabricating a three-dimensional mesostructure comprising:

providing a folding host in an unfolded state, wherein the folding host defines a trench portion between a first bonding site portion and a second bonding site portion of the folding host;

bonding a precursor to the first bonding site portion and the second bonding site portion so that the precursor is suspended across the trench portion of the folding host;

shaping the precursor to the three-dimensional mesostructure by transforming the folding host from the unfolded state to a folded state; and disengaging the three-dimensional mesostructure from the folding host.

2. The method of claim 1, wherein providing the folding host further comprises:

fabricating a glass substrate with a bilayer comprising polydimethylsiloxane (PDMS) and poly lactic-co-glycolic acid (PLGA);

laser cutting a hollow portion on the bilayer to form the trench portion; and removing the bilayer from the glass substrate to form the folding host;

wherein fabricating the glass substrate with the bilayer comprises:

spin casting a PDMS layer on the glass substrate; and spin casting a PLGA layer on the PDMS layer.

3. The method of claim 1, wherein the precursor comprises monocrystalline silicon, wherein bonding the precursor further comprises:

forming the precursor on a device layer of a silicon-on-insulator (SOI) substrate;

retrieving the precursor from the SOI substrate by a polydimethylsiloxane (PDMS) stamp; and transferring the precursor onto the folding host.

4. The method of claim 1, wherein the precursor comprises precursor material, wherein the precursor material comprises at least one of copper or gold, wherein bonding the precursor further comprises:

forming a precursor layer by depositing the precursor material on a sacrificial layer of a silicon wafer substrate;

forming the precursor on the precursor layer;

retrieving the precursor by a polydimethylsiloxane (PDMS) stamp; and transferring the precursor onto the folding host.

5. The method of claim 1, wherein the precursor comprises a first precursor end and a second precursor end that is opposite to the first precursor end, wherein the first precursor end is bound to the first bonding site portion of the folding host, wherein the second precursor end is bound to the second bonding site portion of the folding host.

6. The method of claim 1, wherein the precursor comprises precursor material, wherein, prior to bonding the precursor to the first bonding site portion and the second bonding site portion, the method further comprises:

determining a ratio between a precursor length and a precursor thickness associated with the precursor based at least in part on a material failure threshold associated with the precursor material.

7. The method of claim 1, wherein transforming the folding host from the unfolded state to the folded state comprises:

exerting folding motions on the first bonding site portion and the second bonding site portion along a trench axis of the trench portion.

8. A method for fabricating a three-dimensional epicardial bioelectronic probe comprising:

forming an epicardial bioelectronic precursor, wherein the epicardial bioelectronic precursor comprises a first precursor end portion and a second precursor end portion, wherein at least one strain sensor is positioned between the first precursor end portion and the second precursor end portion;

bonding the epicardial bioelectronic precursor to a folding host in an unfolded state, wherein the folding host defines a trench portion between a first bonding site portion and a second bonding site portion of the folding host;

shaping the epicardial bioelectronic precursor to a three-dimensional epicardial bioelectronic precursor by transforming the folding host from the unfolded state to a folded state;

attaching the three-dimensional epicardial bioelectronic precursor to a distal end of a probe; and inserting the three-dimensional epicardial bioelectronic probe in a catheter.

9. The method of claim 8, wherein the epicardial bioelectronic precursor comprises a polyester layer, a gold layer disposed on top of the polyester layer, and a parylene layer disposed on top of the gold layer, wherein a polyester layer thickness associated with the polyester layer is 10 μm, wherein a gold layer thickness associated with the gold layer is 50 nm, wherein a parylene layer thickness associated with the parylene layer is 2 μm, wherein the at least one strain sensor comprises at least one gold wire forming a strain sensitive pattern on the gold layer, wherein a wire width associated with the at least one gold wire is 110 μm, wherein a gap width associated with the strain sensitive pattern is 30 μm.

10. The method of claim 8, wherein the epicardial bioelectronic precursor comprises a first strain sensor that is positioned on the first precursor end portion and a second strain sensor that is positioned on the second precursor end portion, wherein shaping the epicardial bioelectronic precursor to the three-dimensional epicardial bioelectronic probe further comprises:

exerting folding motions on the first bonding site portion and the second bonding site portion along a trench axis of the trench portion.

11. The method of claim 8, wherein the epicardial bioelectronic precursor comprises:

a first strain sensor that is positioned on a first side of the epicardial bioelectronic precursor and between the first precursor end portion and the second precursor end portion; and a second strain sensor that is positioned on a second side of the epicardial bioelectronic precursor and between the first precursor end portion and the second precursor end portion.

12. The method of claim 8, wherein bonding the epicardial bioelectronic precursor to the folding host further comprises:

bonding the first precursor end portion of the epicardial bioelectronic precursor to the first bonding site portion; and bonding the second precursor end portion of the epicardial bioelectronic precursor to the second bonding site portion.

13. The method of claim 8, wherein encapsulating the three-dimensional epicardial bioelectronic probe in the catheter comprises:

causing the at least one strain sensor to retract within the catheter.

14. A three-dimensional epicardial bioelectronic probe system comprising:

a catheter defining a distal opening; and a three-dimensional epicardial bioelectronic probe formed from the method steps of claim 8, wherein the three-dimensional epicardial bioelectronic precursor comprises at least one cantilever portion, wherein the three-dimensional epicardial bioelectronic probe is transformable between a closed state and an open state, wherein:

when the three-dimensional epicardial bioelectronic probe is in the closed state, the at least one cantilever portion is positioned in the catheter and oriented towards the distal opening of the catheter, and when the three-dimensional epicardial bioelectronic probe is in the open state, the at least one cantilever portion is positioned out of the catheter and arranged radially around the distal opening of the catheter.

15. The three-dimensional epicardial bioelectronic probe system of claim 14, wherein, when the three-dimensional epicardial bioelectronic probe is in the closed state, the three-dimensional epicardial bioelectronic probe is encapsulated in the catheter, wherein the three-dimensional epicardial bioelectronic probe comprises a probe end portion positioned in the catheter and moveable between a proximal end of the catheter and a distal end of the catheter, wherein a movement of the probe end portion from the proximal end of the catheter to the distal end of the catheter causes the three-dimensional epicardial bioelectronic probe to transform from the closed state to the open state.

16. The three-dimensional epicardial bioelectronic probe system of claim 14, wherein, when the three-dimensional epicardial bioelectronic probe is in the closed state, the at least one cantilever portion is in a parallel arrangement with the catheter.

17. The three-dimensional epicardial bioelectronic probe system of claim 14, wherein, when the three-dimensional epicardial bioelectronic probe is in the open state, the at least one cantilever portion is in a non-parallel arrangement with the catheter.

18. The three-dimensional epicardial bioelectronic probe system of claim 14, wherein the at least one cantilever portion comprises a polyester layer, a gold layer disposed on top of the polyester layer, and a parylene layer disposed on top of the gold layer.

19. The three-dimensional epicardial bioelectronic probe system of claim 18, wherein a polyester layer thickness associated with the polyester layer is 10 μm, wherein a gold layer thickness associated with the gold layer is 50 nm, wherein a parylene layer thickness associated with the parylene layer is 2 μm.

20. The three-dimensional epicardial bioelectronic probe system of claim 18, wherein at least one strain sensor is on the gold layer and comprises at least one gold wire forming a strain sensitive pattern, wherein a wire width associated with the at least one gold wire is 110 μm, wherein a gap width associated with the strain sensitive pattern is 30 μm.

* * * * *